United States Patent
Haskell-Luevano et al.

(10) Patent No.: US 11,124,541 B2
(45) Date of Patent: Sep. 21, 2021

(54) CHIMERIC MELANOCORTIN LIGANDS AND METHODS OF USE THEREOF

(71) Applicant: REGENTS OF THE UNIVERSITY OF MINNESOTA, Minneapolis, MN (US)

(72) Inventors: Carrie Haskell-Luevano, Minneapolis, MN (US); Mark David Ericson, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 284 days.

(21) Appl. No.: 15/786,005

(22) Filed: Oct. 17, 2017

(65) Prior Publication Data

US 2018/0118789 A1     May 3, 2018

Related U.S. Application Data

(60) Provisional application No. 62/409,620, filed on Oct. 18, 2016.

(51) Int. Cl.
    *C07K 7/64*     (2006.01)
    *A61K 38/12*     (2006.01)
    *A61P 3/04*     (2006.01)

(52) U.S. Cl.
    CPC ............... *C07K 7/64* (2013.01); *A61K 38/12* (2013.01); *A61P 3/04* (2018.01)

(58) Field of Classification Search
    CPC .............. A61K 38/12; A61P 3/04; C07K 7/64
    See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,612,302 A | 9/1986 | Szabo et al. |
| 4,684,620 A | 8/1987 | Hruby et al. |
| 4,820,508 A | 4/1989 | Wortzman |
| 4,853,371 A | 8/1989 | Coy et al. |
| 4,938,949 A | 7/1990 | Borch et al. |
| 4,992,478 A | 2/1991 | Geria |
| 6,500,934 B1 | 12/2002 | Lerner et al. |
| 8,946,265 B2 | 2/2015 | Zhang et al. |
| 9,040,663 B2 | 5/2015 | Dodd et al. |
| 10,899,793 B2 | 1/2021 | Haskell-Luevano et al. |
| 2004/0224901 A1 | 11/2004 | Chaturvedula et al. |
| 2011/0009341 A1 | 1/2011 | Sharma et al. |
| 2017/0342107 A1 | 11/2017 | Haskell-Luevano et al. |
| 2018/0360972 A1 | 12/2018 | Haskell-Luevano et al. |
| 2019/0255142 A1 | 8/2019 | Hruby et al. |
| 2020/0115416 A1 | 4/2020 | Haskell-Luevano et al. |
| 2021/0179666 A1 | 6/2021 | Haskell-Luevano et al. |

FOREIGN PATENT DOCUMENTS

| | | | |
|---|---|---|---|
| WO | 2002018437 A2 | 3/2002 | |
| WO | 2003006604 A2 | 1/2003 | |
| WO | WO-2007123839 A2 * | 11/2007 | ............. C07K 14/47 |
| WO | WO-2009061411 A2 * | 5/2009 | ............. A61K 38/12 |
| WO | 2011153817 A1 | 12/2011 | |

OTHER PUBLICATIONS

Peteris Prusis, Design of newsmall cyclic melanocortin receptor-binding peptides using molecular modelling: Role of the His residue in the melanocortin peptide core, Eur. J. Med. Chem. 36 (2001) 137-146.*
U.S. Appl. No. 15/605,213, 2017-0342107.
U.S. Appl. No. 15/969,670, 2018-0360972.
Dehigaspitiya, et al., "Linear scaffolds for multivalent targeting of melanocortin receptors.", Org Biomol Chem 13, 11507-11517 (2015).
Dehigaspitiya, et al., "Synthesis and bioactivity of MSH4 oligomers prepared by an A2+B2 strategy.", Tetrahedron Lett 56(23), 3060-3065 (2015).
Doering, et al., "Discovery of Mixed Pharmacology Melanocortin-3 Agonists and Melanocortin-4 Receptor Tetrapeptide Antagonist Compounds (TACOs) Based on the Sequence Ac-Xaa1-Arg-(pI)DPhe-Xaa4-NH2", J Med Chem 60(10), 4342-4357 (2017).
Doering, "Discovery of Peptide and Peptidomimetic Based Ligands Targeting the Melanocortin Receptors: A campaign in mixture-based positional scanning, chemical topology, and structure-activity relationships", Dissertation Submitted to the Faculty of the University of Minnesota, in Partial Fulfillment of the Requirements for the Degree of Doctor of Philosophy, 181 pages (Jul. 2016).
Doering, et al., "Melanocortin Antagonist Tetrapeptides with Minimal Agonist Activity at the Mouse Melanocortin-3 Receptor.", ACS Med Chem Lett 6(2), 123-127 (2015).
Dooley, et al., "Selective Ligands for the μ, δ, and κ Opioid Receptors Identified from a Single Mixture Based Tetrapeptide Positional Scanning Combinatorial Library", J. Biol. Chem. 273(30), 18848-18856 (1998).
Dooley, et al., "The use of positional scanning synthetic peptide combinatorial libraries for the rapid determination of opioid receptor ligands", Life Sci. 52(18), 1509-1517 (1993).
Durroux, "Principles: A model for the allosteric interactions between ligand binding sites within a dimeric GPCR.", Trends Pharmacol Sci 26, 376-384 (2005).

(Continued)

*Primary Examiner* — Julie Ha
*Assistant Examiner* — Erinne R Dabkowski
(74) *Attorney, Agent, or Firm* — Viksnins Harris Padys Malen LLP

(57) ABSTRACT

The invention provides compounds having the general formula I:

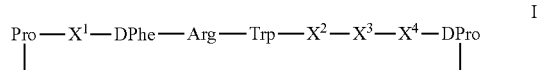

and salts thereof, wherein the variables Pro, DPro, DPhe, Arg, Trp, $X^1$, $X^2$, $X^3$ and $X^4$ have the meaning as described herein, and compositions containing such compounds and methods for using such compounds and compositions.

22 Claims, 6 Drawing Sheets

Specification includes a Sequence Listing.

(56) References Cited

OTHER PUBLICATIONS

Ebihara, et al., "Involvement of Agouti-Related Protein, an Endogenous Antagonist of Hypothalamic Melanocortin Receptor, in Leptin Action.", Diabetes 48, 2028-2033 (1999).
Echalier, et al., "Heating and microwave assisted SPPS of C-terminal acid peptides on trityl resin: the truth behind the yield.", Amino Acids 45, 1395-1403 (2013).
Ellacott, et al., "Assessment of feeding behavior in laboratory mice.", Cell Metab 12(1), 10-17 (2010).
Elshan, et al., "Trigonal scaffolds for multivalent targeting of melanocortin receptors.", Org Biomol Chem 13(6), 1778-1791 (2015).
Elster et al., "Bioluminescence Resonance Energy Transfer as a Screening Assay: Focus on Partial and Inverse Agonism.", J Biomol Screen 12, 41-49 (2007).
Emmerson, "Melanocortin-4 receptor agonists for the treatment of obesity", Current Topics in Medicinal Chemistry 7(11), 1121-1130 (2007).
Erez et al. "Narcotic Antagonistic Potency of Bivalent Ligands Which Contain β-Naltrexamine. Evidence for Bridging between Proximal Recognition Sites.", J Med Chem 25, 847-849 (1982).
Ericson, et al., "A fragment of the *Escherichia coli* ClpB heat-shock protein is a micromolar melanocortin 1 receptor agonist.", Bioorg Med Chem Lett 25(22), 5306-5308 (2015).
Ericson, et al., "A Macrocyclic Agouti-Related Protein/[Nle4, DPhe7]α-Melanocyte Stimulating Hormone Chimeric Scaffold Produces Subnanomolar Melanocortin Receptor Ligands", J Med Chem 60(2), 805-813 (2017).
Ericson, et al., "Bench-top to clinical therapies: A review of melanocortin ligands from 1954 to 2016.", Biochim Biophys Acta Mol Basis Dis 1863, 2414-2435 (2017).
Ericson, et al., "Discovery of a β-Hairpin Octapeptide, c[Pro-Arg-Phe-Phe-Dap-Ala-Phe-DPro], Mimetic of Agouti-Related Protein(87-132)[AGRP(87-132)] with Equipotent Mouse Melanocortin-4 Receptor (mMC4R) Antagonist Pharmacology.", J Med Chem 58(11), 4638-4647 (2015).
Fan, et al., "Role of melanocortinergic neurons in feeding and the agouti obesity syndrome.", Nature 385(6612), 165-168 (1997).
Farooqi, et al., "Clinical Spectrum of Obesity and Mutations in the Melanocortin 4 Receptor Gene.", N Engl J Med 348(12), 1085-1095 (2003).
Fernandes, et al., "Synthesis and evaluation of bivalent ligands for binding to the human melanocortin-4 receptor.", Bioorg Med Chem 22, 6360-6365 (2014).
Ferre, "G Protein-Coupled Receptor Oligomerization Revisited: Functional and Pharmacological Perspectives.", Pharmacol Rev 66, 413-434 (2014).
Ferre, et al., "The GPCR Heterotetramer: Challenging Classical Pharmacology.", Trends Pharmacol Sci 36(3), 145-152 (2015).
Fields, et al., "Solid phase peptide synthesis utilizing 9-fluorenylmethoxycarbonyl amino acids", Int. J. Pept. Protein Res. 35(3), 161-214 (1990).
Filpula, et al., "Releasable PEGylation of proteins with customized linkers.", Advanced Drug Delivery 60, 29-49 (2008).
Finan, et al., "A rationally designed monomeric peptide triagonist corrects obesity and diabetes in rodents", Nat. Med. 21(1), 27-36 (2015).
Finan, et al., "Unimolecular Dual Incretins Maximize Metabolic Benefits in Rodents, Monkeys, and Humans", Science Translational Medicine 5(209), 209ra151-209ra151 (2013).
Gantz, et al., "Molecular cloning of a novel melanocortin receptor.", J Biol Chem 268(11), 8246-8250 (1993).
Gantz, et al., "Molecular cloning, expression, and characterization of a fifth melanocortin receptor.", Biochem Biophys Res Commun 200(3), 1214-1220 (1994).
Gantz, et al., "Molecular cloning, expression, and gene localization of a fourth melanocortin receptor.", J Biol Chem 268(20), 15174-15179 (1993).
Gao, et al., "Agonist-Dependent Internalization of the Human Melanocortin-4 Receptors in Human Embryonic Kidney 293 Cells.", J Pharmacol Exp Ther 307, 870-877 (2003).
Ghamari-Langroudi, et al., "G-protein-independent coupling of MC4R to Kir7.1 in hypothalamic neurons", Nature 520(7545), 94-98 (2015).
Giuliani, et al., "Melanocortins protect against progression of Alzheimer's disease in tripletransgenic mice by targeting multiple pathophysiological pathways.", Neurobiol Aging 35, 537-547 (2014).
Giuliani, et al., "NDP-α-MSH induces intense neurogenesis and cognitive recovery in Alzheimer transgenic mice through activation of melanocortin MC4 receptors.", Mol Cell Neurosci 67, 13-21 (2015).
Goodman, et al., "On the concept of linear modified retro-peptide structures", Acc. Chem. Res. 12(1), 1-7 (1979).
Gracia, et al., "Homodimerization of adenosine A1 receptors in brain cortex explains the biphasic effects of caffeine.", Neuropharmacology 71, 56-69 (2013).
Grant, et al., "Agonist-dependent Dissociation of Human Somatostatin Receptor 2 Dimers.", J Biol Chem 279(35), 36179-36183 (2004).
Greenfield, et al., "Modulation of Blood Pressure by Central Melanocortinergic Pathways.", New Engl J Med 360, 44-52 (2009).
Grieco, et al., "D-Amino acid scan of gamma-melanocyte-stimulating hormone: importance of Trp(8) on human MC3 receptor selectivity", J. Med. Chem. 43(26), 4998-5002 (2000).
Grieco, et al., "Further structure-activity studies of lactam derivatives of MT-II and SHU-9119: Their activity and selectivity at human melanocortin receptors 3, 4 and 5", Peptides 28(6), 1191-1196 (2007).
Grieco, et al., "Structure-Activity Studies of the Melanocortin Peptides: Discovery of Potent and Selective Affinity Antagonists for the hMC3 and hMC4 Receptors", J. Med. Chem. 45(24), 5287-5294 (2002).
Griffon, et al., "Molecular cloning and characterization of the rat fifth melanocortin receptor.", Biochem Biophys Res Commun 200(2), 1007-1014 (1994).
Hadley, "Discovery that a melanocortin regulates sexual functions in male and female humans", Peptides 26(10), 1687-1689 (2005).
Hahn, et al., "Coexpression of Agrp and NPY in fasting-activated hypothalamic neurons.", Nat Neurosci 1, 271-272 (1998).
Han, et al., "Allosteric communication between protomers of dopamine Class A GPCR dimers modulates activation.", Nat Chem Biol 5, 688-695 (2009).
Handl, et al., "Synthesis and Evaluation of Bivalent NDP-α-MSI-1(7) Peptide Ligands for Binding to the Human Melanocortin Receptor 4 (hMC4R).", Bioconjug Chem 18(4), 1101-1109 (2007).
Hano, et al., "Evaluation of the physiological properties of d-histidyl-d-phenylalanyl-d-arginyl-d-tryptophyl-glycine in frog melanocyte", Biochimica et Biophysica Acta 9BBA)—General Subjects 90(1), 201-204 (1964).
Haskell-Luevano, et al., "Characterization of Melanocortin NDP-MSH Agonist Peptide Fragments at the Mouse Central and Peripheral Melanocortin Receptors.", J Med Chem 44(13), 2247-2252 (2001).
Haskell-Luevano, et al., "Characterization of the Neuroanatomical Distribution of Agouti-Related Protein Immunoreactivity in the Rhesus Monkey and the Rat.", Endocrinology 140, 1408-1415 (1999).
Masman, "Synthesis and conformational analysis of his-phe-arg-trp-nh2 and analogues with antifungal properties", Bioorganic and Medicinal Chemistry 14, 7604-7614 (2006).
Roselli-Rehfuss, et al., "Identification of a receptor for gamma melanotropin and other proopiomelanocortin peptides in the hypothalamus and limbic system.", Proc Natl Acad Sci USA 90(19), 8856-8860 (1993).
Russo, et al., "Synthesis of specific bivalent probes that functionally interact with 5-HT(4) receptor dimers.", J Med Chem 50(18), 4482-4492 (2007).
Santos, et al., "A comprehensive map of molecular drug targets.", Nat Rev Drug Discov 16, 19-34 (2017).
Santos, et al., "Use and Implications of the Harmonic Mean Model on Mixtures for Basic Research and Drug Discovery", ACS Comb. Sci. 13(3), 337-344 (2011).

(56) References Cited

OTHER PUBLICATIONS

Sartania, et al., "Agonist occupancy of a single monomeric element is sufficient to cause internalization of the dimeric β2-adrenoceptor.", Cell Signal 19, 1928-1938 (2007).
Sawyer, et al., "4-Norleucine, 7-D-phenylalanine-α-melanocyte-stimulating Hormone: A Highly Potent α-melanotropin with Ultralong Biological Activity.", Proc Natl Acad Sci USA 77(10), 5754-5758 (1980).
Schild, "pA, A New Scale for the Measurement of Drug Antagonism", British Journal of Pharmacology 2(3), 189-206 (1947).
Schiöth, et al., "Major pharmacological distinction of the ACTH receptor from other melanocortin receptors", Life Sci. 59(10), 797-801 (1996).
Shinyama, et al., "Regulation of Melanocortin-4 Receptor Signaling: Agonist-Mediated Desensitization and Internalization.", Endocrinology 144, 1301-1314 (2003).
Singh, et al., "Incorporation of a Bioactive Reverse-Turn Heterocycle into a Peptide Template Using Solid-Phase Synthesis to Probe Melanocortin Receptor Selectivity and Ligand Conformations by 2D 1H NMR.", J Med Chem 54, 1379-1390 (2011).
Singh, et al., "Synthesis and pharmacology of α/β3-peptides based on the melanocortin agonist Ac-His-d Phe-Arg-Trp-NH2 sequence.", ACS Med Chem Lett 6(5), 568-572 (2015).
Smeester, et al., "Targeting putative mu opioid/metabotropic glutamate receptor-5 heteromers produces potent antinociception in a chronic murine bone cancer model.", Eur J Pharmacol. 743, 48-52 (2014).
Smith, et al., "Allostery at G Protein-Coupled Receptor Homo- and Heteromers: Uncharted Pharmacological Landscapes.", Pharmacol Rev 62, 701-725 (2010).
Smith, et al., "Comparison of biosequences.", Adv Appl Math 2(4), 482-489 (1981).
Smith, "Experimental Ablation of the Hypophysis in the Frog Embryo", Science 44(1130), 280-282 (1916).
Stephenson, "A Modification of Receptor Theory", Br J Pharmacol Chemother 11, 379-393 (1956).
Szalai, "Allosteric interactions within the AT1 angiotensin receptor homodimer: Role of the conserved DRY motif.", Biochem Pharmacol 84, 477-485 (2012).
Tabor, et al., "Visualization and ligand-induced modulation of dopamine receptor dimerization at the single molecule level.", Sci Rep 6, 33233 (2016).
Takeyasu, et al., "Experimental evidence and dynamic aspects of spare receptor.", Life Sci 25(20), 1761-1771 (1979).
Tala et al. "Microwave-assisted solid-phase synthesis of side-chain to side-chain lactam-bridge cyclic peptides.", Bioorg Med Chem Lett 25(24), 5708-5711 (2015).
Tam, et al., "SN2 deprotection of synthetic peptides with a low concentration of HF in dimethyl sulfide: evidence and application in peptide synthesis", J. Am. Chem. Soc. 105(21), 6442-6455 (1983).
Tanner, et al., "Fasting-induced reductions in cardiovascular and metabolic variables occur sooner in obese vs. lean mice.", Exp Biol Med (Maywood) 235(12), 1489-1497 (2010).
Teitler, et al., "A new approach for studying GPCR dimers: drug-induced inactivation and reactivation to reveal GPCR dimer function in vitro, in primary culture, and in vivo.", Pharmacol Ther 133, 205-217 (2012).
Todorovic, et al., "N-Terminal Fatty Acylated His-dPhe-Arg-Trp-NH2 Tetrapeptides: Influence of Fatty Acid Chain Length on Potency and Selectivity at the Mouse Melanocortin Receptors and Human Melanocytes", J. Med. Chem. 48 (9), 3328-3336 (2005).
Todorovic, et al., "Synthesis and activity of the melanocortin Xaa-d-Phe-Arg-Trp-NH tetrapeptides with amide bond modifications", J Peptide Res 63, 270-278 (2004).
Tota, et al., "Molecular Interaction of Agouti Protein and Agouti-Related Protein with Human Melanocortin Receptors.", Biochemistry 38(3), 897-904 (1999).
Uckert, et al., "Melanocortin receptor agonists in the treatment of male and female sexual dysfunctions: results from basic research and clinical studies.", Expert Opin Invest Drugs 23(11), 1477-1483 (2014).
Vagner, et al., "Novel targeting strategy based on multimeric ligands for drug delivery and molecular imaging: homooligomers of α-MSH.", Bioorg Med Chem Lett 14, 211-215 (2004).
Van Der Ploeg, et al., "A role for the melanocortin 4 receptor in sexual function.", Proc Natl Acad Sci USA 99(17), 11381-11386 (2002).
Violin, et al., "Biased ligands at G-protein-coupled receptors: promise and progress", Trends Pharmacol Sci 35, 308-316 (2014).
Weeden, et al., "A retro-inverso α-melanocyte stimulating hormone analog with MC1R-binding selectivity", J. Pept. Sci. 17(1), 47-55 (2011).
Wessells, et al., "Synthetic melanotropic peptide initiates erections in men with psychogenic erectile dysfunction: double-blind, placebo controlled crossover study", J. Urol. 160(2), 389-393 (1998).
Wilczynski, et al., "Identification of Putative Agouti-Related Protein(87-132)-Melanocortin-4 Receptor Interactions by Homology Molecular Modeling and Validation Using Chimeric Peptide Ligands.", J Med Chem 47(9), 2194-2207 (2004).
Wilczynski, et al., "Structure-Activity Relationships of the Unique and Potent Agouti-Related Protein (AGRP)-Melanocortin Chimeric Tyr-c[â-Asp-His-DPhe-Arg-Trp-Asn-Ala-Phe-Dpr]-Tyr-NH2 Peptide Template.", J Med Chem 48, 3060-3075 (2005).
Xiang, et al., "Peptide and Small Molecules Rescue the Functional Activity and Agonist Potency of Dysfunctional Human Melanocortin-4 Receptor Polymorphisms.", Biochemistry 46, 8273-8287 (2007).
Xiang, et al., "Pharmacological Characterization of 30 Human Melanocortin-4 Receptor Polymorphisms with the Endogenous Proopiomelanocortin Derived Agonists, Synthetic Agonists, and the Endogenous Agouti-Related Protein (AGRP) Antagonist.", Biochemistry 49(22), 4583-4600 (2010).
Xiang, et al., "Pharmacological Characterization of 40 Human Melanocortin-4 Receptor Polymorphisms with the Endogenous Proopiomelanocortin-Derived Agonists and the Agouti-Related Protein (AGRP) Antagonist.", Biochemistry 45, 7277-7288 (2006).
Xu, et al., "Heterobivalent ligands target cell-surface receptor combinations in vivo.", Proc Natl Acad Sci USA 109, 21295-21300 (2012).
Yang, et al., "Biased signaling initiated by agouti-related peptide through human melanocortin-3 and -4 receptors", Biochim Biophys Acta 1862, 1485-1494 (2016).
Yang, et al., "Characterization of Agouti-Related Protein Binding to Melanocortin Receptors.", Mol Endocrinol 13, 148-155 (1999).
Ye, et al., "Structure-activity relationship of linear tetrapeptides Tic-DPhe-Arg-Trp-NH2 at the human melanocortin-4 receptor and effects on feeding behaviors in rat", Peptides 26(10), 2017-2025 (2005).
Zhao, et al., "Drug Conjugates with Poly(Ethylene Glycol).", Drug Delivery in Oncology, 627-656 (2012).
Zheng, et al., "Induced association of mu opioid (MOP) and type 2 cholecystokinin (CCK2) receptors by novel bivalent ligands.", J Am Chem 52(2), 247-258 (2009).
Zylbergold, et al., "A division of labor: asymmetric roles for GPCR subunits in receptor dimers.", Nat Chem Biol 5(9), 608-609 (2009).
Kroeze, et al., "PRESTO-TANGO: an open-source resource for interrogation of the druggable human GPCR-ome.", Nat Struct Mol Biol 22, 362-369 (2015).
Kuhhorn, et al., "Development of a Bivalent Dopamine D2 Receptor Agonist.", J Med Chem 54, 7911-7919 (2011).
Langendonk, et al., "Afamelanotide for Erythropoietic Protoporphyria.", N Engl J Med 373, 48-59 (2015).
Le Naour, et al., "Bivalent Ligands That Target μ Opioid (MOP) and Cannabinoid1 (CB1) Receptors Are Potent Analgesics Devoid of Tolerance.", J Med Chem 56(13), 5505-5513 (2013).
Le Naour, et al., "Putative Kappa Opioid Heteromers As Targets for Developing Analgesics Free of Adverse Effects.", J Med Chem 57, 6383-6392 (2014).
Lensing, et al., "A Direct In Vivo Comparison of the Melanocortin Monovalent Agonist Ac-His-DPhe-Arg-Trp-NH2 versus the Biva-

(56) References Cited

OTHER PUBLICATIONS lent Agonist Ac-His-DPhe-Arg-Trp-PEDG20-His-DPhe-Arg-Trp-NH2: A Bivalent Advantage.", ACS Chem Neurosci 8(6), 1262-1278 (2017).
Lensing, et al., "Ac-Trp-DPhe(p-l)-Arg-Trp-NH2, a 250-Fold Selective Melanocortin-4 Receptor (MC4R) Antagonist over the Melanocortin-3 Receptor (MC3R), Affects Energy Homeostasis in Male and Female Mice Differently", ACS Chem Neurosci 8, 1283-1291 (2016).
Lensing, et al., "An in vitro and in vivo investigation of bivalent ligands that display preferential binding and functional activity for different melanocortin receptor homodimers.", J Med Chem 59, 3112-3128 (2016).
Lensing, et al., "Bivalent Ligands as Pharmacological Probes for the Melanocortin Receptors: The Bivalent Advantage", Dissertation submitted to the Faculty of University of Minnesota in Partial Fulfillment of the Requirements for the Degree of Doctor of Philosophy, 327 pages, May 2017.
Lensing, et al., "Developing a Biased Unmatched Bivalent Ligand (BUmBL) Design Strategy to Target the GPCR Homodimer Allosteric Signaling (cAMP over β-Arrestin 2 Recruitment) Within the Melanocortin Receptors.", J Med Chem, Just Accepted (2018).
Lensing, et al., "The Ac-Trp-DPhe(p-l)-Arg-Trp-NH2 250-Fold Selective Melanocortin-4 Receptor (MC4R) Antagonist over the Melanocortin-3 Receptor (MC3R) Affects Energy Homeostasis in Male and Female Mice Differently.", ACS Chem Neurosci 7(9), 1283-1291 (2016).
Lu, et al., "Agouti protein is an antagonist of the melanocyte-stimulating-hormone receptor.", Nature 371(6500), 799-802 (1994).
Mandrika, et al., "Melanocortin receptors form constitutive homo- and heterodimers.", Biochem Biophys Res Commun 326, 349-354 (2005).
Marsh, et al., "Effects of neuropeptide Y deficiency on hypothalamic agouti-related protein expression and responsiveness to melanocortin analogues.", Brain Research 848, 66-77 (1999).
Marsh, et al., "Response of melanocortin-4 receptor-deficient mice to anorectic and orexigenic peptides.", Nat Genet 21, 119-122 (1999).
Marti-Solano, et al., "Drugging specific conformational states of GPCRs: challenges and opportunities for computational chemistry", Drug Discovery Today 21, 625-631 (2016).
Marvyn, et al., "Data onoxygenconsumptionrate,respiratory exchangeratio,andmovementinC57BL/6J female miceonthethirdayofconsuming a high-fatdiet.", Data in Brief 7, 472-475 (2016).
Mayorov, et al., "Solid-phase peptide head-to-side chain cyclodimerization: Discovery of C2-symmetric cyclic lactam hybrid α-melanocyte-stimulating hormone (MSH)/agouti-signaling protein (ASIP) analogues with potent activities at the human melanocortin receptors", Peptides 31(10), 1894-1905 (2010).
McNulty, et al., "High-Resolution NMR Structure of the Chemically-Synthesized Melanocortin Receptor Binding Domain AGRP(87-132) of the Agouti-Related Protein", Biochemistry 40, 15520-15527 (2001).
Merrifield, et al., "Solid Phase Peptide Synthesis. I. The Synthesis of a Tetrapeptide", JACS 85, 2149-2154 (1963).
Miller, et al., "Cloning of the mouse agouti gene predicts a secreted protein ubiquitously expressed in mice carrying the lethal yellow mutation", Genes. Dev. 7(3), 454-467 (1993).
Mo, et al., "Activation of MAPK by inverse agonists in six naturally occurring constitutively active mutant human melanocortin-4 receptors", Biochim. Biophys. Acta. 1832(12) 1939-1948 (2013).
Mountjoy, et al., "Localization of the melanocortin-4 receptor (MC4-R) in neuroendocrine and autonomic control circuits in the brain", Mol. Endocrinol. 8(10), 1298-1308 (1994).
Mountjoy, et al., "The cloning of a family of genes that encode the melanocortin receptors.", Science 257(5074), 1248-1251 (1992).
Mutulis, et al., "Reductive amination products containing naphthalene and indole moieties bind to melanocortin receptors", Bioorg. Med. Chem. Lett. 12(7), 1035-1038 (2002).
Myers, et al., "Optimal alignments in linear space.", CABIOS 4(1), 11-17 (1988).
Nakanishi, et al., "Nucleotide sequence of cloned cDNA for bovine corticotropin-beta-lipotropin precursor.", Nature 278(5703), 423-427 (1979).
Needleman, et al., "A General Method Applicable to the Search for Similarities in the Amino Acid Sequence of Two Proteins.", J Mol Biol 48, 443-453 (1970).
Ni, et al., "Central receptors mediating the cardiovascular actions of melanocyte stimulating hormones", J. Hypertens. 24(11), 2239-2246 (2006).
Nickolls, et al., "Dimerization of the melanocortin 4 receptor: A study using bioluminescence resonance energy transfer.", Peptides 27, 380-387 (2006).
Nickolls, et al., "Functional Selectivity of Melanocortin 4 Receptor Peptide and Nonpeptide Agonists: Evidence for Ligand-Specific Conformational States", J Pharmacol Exp Ther 313, 1281-1288 (2005).
Odagami, "Design of cyclic peptides with agonist activity at melanocortin receptor-4", Bioorg Med Chem Lett 16(14), 3723-3726 (2006).
Ollmann, et al., "Antagonism of Central Melanocortin Receptors in Vitro and in Vivo by Agouti-Related Protein.", Science 278(5335), 135-138 (1997).
Orcel, et al., "Differential Coupling of the Vasopressin V1b Receptor through Compartmentalization within the Plasma Membrane.", Mol Pharmacol 75, 637-647 (2009).
Ostresh, et al., "Peptide libraries: Determination of relative reaction rates of protected amino acids in competitive couplings", Biopolymers 34(12), 1681-1689 (1994).
Otsuka, et al., "Synthesis of peptides related to the N-terminal structure of corticotropin. III. The synthesis of L-histidyl-L-phenylalanyl-L-tryptophan, the smallest peptideexhibiting the melanocyte-stimulating and the lipolytic activities", Bull. Chem. Soc. Jpn. 37(10), 1465-1471 (1964).
Pearson, et al., "Improved tools for biological sequence comparison.", Proc Natl Acad Sci 85, 2444-2448 (1988).
Pearson, et al., "Using the FASTA program to search protein and DNA sequence databases.", Meth Mol Biol 24, 307-331 (1994).
Pellissier, et al., "G Protein Activation by Serotonin Type 4 Receptor Dimers.", J Biol Chem 286, 9985-9997 (2011).
Penagarikano, et al., "Exogenous and evoked oxytocin restores social behavior in the Cntnap2 mouse model of autism.", Sci Transl Med 7(271), 271ra8 (2015).
Pfleger, et al., "Bioluminescence resonance energy transfer (BRET) for the real-time detection of protein-protein interactions.", Nat Protoc 1(1), 337-345 (2006).
Piechowski, et al., "Inhibition of melanocortin-4 receptor dimerization by substitutions in intracellular loop 2.", J Mol Endocrinol 51, 109-118 (2013).
Pin, et al., "Allosteric functioning of dimeric class C G-protein-coupled receptors.", FEBS J 272, 2947-2955 (2005).
Pinilla, et al., "Advances in the use of synthetic combinatorial chemistry: mixture-based libraries", Nat. Med. 9(1), 118-122 (2003).
Pinilla, et al., "Rapid identification of high affinity peptide ligands using positional scanning synthetic peptide combinatorial libraries", BioTechniques 13(6), 901-905 (1992).
Poggioli, et al., "ACTH-(1-24) and alpha-MSH antagonize feeding behavior stimulated by kappa opiate agonists.", Peptides 7, 843-848 (1986).
Portoghese, et al., "Heteromer Induction: An Approach to Unique Pharmacology?", ACS Chem Neurosci 8, 426-428 (2017).
Portoghese, et al., "Opioid Agonist and Antagonist Bivalent Ligands as Receptor Probes.", Life Sciences, 31(12 & 13), 1283-1286 (1982).
Proneth, et al., "Melanocortin Tetrapeptide Ac-His-DPhe-Arg-Trp-NH2 Modified at the Para Position of the Benzyl Bide Chain (DPhe): Importance for Mouse Melanocortin-3 Receptor Agonist versus Antagonist Activity", J. Med. Chem. 51(18), 5585-5593 (2008).
Rask-Andersen, et al., "Trends in the exploitation of novel drug targets.", Nat Rev Drug Discov 10, 579-590 (2011).

(56) References Cited

OTHER PUBLICATIONS

Akgun, et al., "Inhibition of Inflammatory and Neuropathic Pain by Targeting a Mu Opioid Receptor/Chemokine Receptor5 Heteromer (MOR-CCR5).", J Med Chem 58(21), 8647-8657 (2015).
Albizu, et al., "Time-resolved FRET between GPCR ligands reveals oligomers in native tissues.", Nat Chem Biol 6(8), 587-594 (2010).
Allen, "The Results of Extirpation of the Anterior Lobe of the Hypophysis and of the Thyroid of Rana Pipiens Larvae", Science 44, 755-758 (1916).
Altschul, et al., "Basic local alignment search tool.", J Mol Biol 215, 403-410 (1990).
Altschul, et al., "Gapped BLAST and PSI-BLAST: a new generation of protein database search programs.", Nucleic Acids Res 25(17), 3389-3402 (1997).
Atalayer, et al., "Food demand and meal size in mice with single or combined disruption of melanocortin type 3 and 4 receptors", Am. J. Physiol. Intergr. Comp. Physiol. 298(6), R1667-R1674 (2010).
Ballet, et al., "Novel selective human melanocortin-3 receptor ligands: Use of the 4-amino-1,2,4,5-tetrahydro-2-benzazepin-3-one (Aba) scaffold", Bioorg. Med. Chem. Lett. 17(9), 2492-2498 (2007).
Barkey, et al., "Development of melanoma-targeted polymer micelles by conjugation of a Melanocortin 1 Receptor (MC1R) specific ligand.", J Med Chem 54, 8078-8084 (2011).
Barnea, et al., "The genetic design of signaling cascades to record receptor activation.", PNAS 105(1), 64-69 (2008).
Barrett, et al., "Neonatal melanocortin receptor agonist treatment reduces play fighting and promotes adult attachment in prairie voles in a sex-dependent manner.", Neuropharmacology 85, 357-366 (2014).
Boeglin, et al., "Aza-scanning of the Potent Melanocortin Receptor Agonist Ac-His-d-Phe-Arg-Trp-NH2", Chem Biol Drug Des 67(4), 275-283 (2006).
Bolin, et al., "NMR structure of a minimized human agouti related protein prepared by total chemical synthesis.", FEBS Lett 451, 125-131 (1999).
Bowen, et al., "Design, Synthesis, and Validation of a Branched Flexible Linker for Bioactive Peptides.", J Org Chem 72(5), 1675-1680 (2007).
Brabez, et al., "Design, synthesis and biological studies of efficient multivalent melanotropin ligands: tools towards melanoma diagnosis and treatment.", J Med Chem 54(20), 7375-7384 (2011).
Brabez, et al., "Multivalent Interactions: Synthesis and Evaluation of Melanotropin Multimers—Tools for Melanoma Targeting.", ACS Med Chem Lett 4, 98-102 (2013).
Breit, et al., "Alternative G protein-coupling and biased agonism: new insights into melanocortin-4 receptor signalling", Mol Cell Endocrinol 331, 232-240 (2010).
Brock, et al., "Activation of a Dimeric Metabotropic Glutamate Receptor by Intersubunit Rearrangement.", J Biol Chem 282, 33000-33008 (2007).
Broussard, et al., "Fluorescence resonance energy transfer microscopy as demonstrated by measuring the activation of the serine/threonine kinase Akt.", Nat Protoc 8(2), 265-281 (2013).
Brown, et al., "Central injection in rats of a-melanocyte-stimulating hormone analog: effects on food intake and brain Fos.", Regul Peptides 78, 89-94 (1998).
Büch, et al., "Pertussis Toxin-sensitive Signaling of Melanocortin-4 Receptors in Hypothalamic GT1-7 Cells Defines Agouti-related Protein as a Biased Agonist", J. Biol. Chem. 284(39), 26411-26420 (2009).
Bultman, et al., "Molecular characterization of the mouse agouti locus", Cell 71(7), 1195-1204 (1992).
Butler, et al., "A unique metabolic syndrome causes obesity in the melanocortin-3 receptor-deficient mouse.", Endocrinol 141(9), 3518-3521 (2000).
Cai, et al., "Cell Signaling and Trafficking of Human Melanocortin Receptors in Real Time Using Two-photon Fluorescence and Confocal Laser Microscopy: Differentiation of Agonists and Antagonists.", Chem Biol Drug Des 68(4), 183-193 (2006).
Carotenuto, et al., "Discovery of Novel Potent and Selective Agonists at the Melanocortin-3 Receptor", J. Med. Chem. 58(24), 9773-9778 (2015).
Carpino, et al., "The 9-Fluorenylmethoxycarbonyl Amino-Protecting Group.", J Org Chem 37(22), 3404-3409 (1972).
Carpino, et al., "The 9-Fluorenylmethoxycarbonyl Function, a New Base-Sensitive Amino-Protecting Group.", J Am Chem Soc 92, 5748-5749 (1970).
Carrithers, et al., "Synthesis and characterization of bivalent peptide ligands targeted to G-protein-coupled receptors.", Chemistry & Biology 3(7), 537-542 (1996).
Casado, et al., "Old and new ways to calculate the affinity of agonists and antagonists interacting with G-protein-coupled monomeric and dimeric receptors: The receptor-dimer cooperativity index.", Pharmacol Ther 116, 343-354 (2007).
Chapman, et al., "The melanocortin 4 receptor: Oligomer formation, interaction sites and functional significance.", Biochim Biophys Acta 1828, 535-542 (2013).
Chen, et al., "A Colorimetric Assay for Measuring Activation of Gs- and Gq-Coupled Signaling Pathways", Anal. Biochem. 226(2), 349-354 (1995).
Chen, et al., "Calcium phosphate-mediated gene transfer: a highly efficient transfection system for stably transforming cells with plasmid DNA.", BioTechniques 6(7), 632-638 (1988).
Chen, et al., "Exocrine Gland Dysfunction in MC5-R-Deficient Mice: Evidence for Coordinated Regulation of Exocrine Gland Function by Melanocortin Peptides.", Cell 91(6), 789-798 (1997).
Chen, et al., "Functional characterization of the modified melanocortin peptides responsible for ligand selectivity at the human melanocortin receptors.", Peptides 27, 2836-2845 (2006).
Chen, et al., "Inactivation of the mouse melanocortin-3 receptor results in increased fat mass and reduced lean body mass.", Nat Genet 26, 97-102 (2000).
Cheung, et al., "Structure-Activity relationship of linear peptide Bu-His-DPhe-Arg-Trp-Gly-NH2 at the human melanocortin-1 and -4 receptors: arginine substitution", Bioorg. Med. Chem. Lett. 12(17), 2407-2410 (2002).
Chhajlani, et al., "Molecular cloning and expression of the human melanocyte stimulating hormone receptor cDNA.", FEBS Lett 309(3), 417-420 (1992).
Chhajlani, et al., "Molecular cloning of a novel human melanocortin receptor.", Biochem Biophys Res Commun 195, 866-873 (1993).
Chorev, et al., "A dozen years of retro-inverso peptidomimetics", Acc. Chem. Res. 26(5), 266-273 (1993).
Chorev, et al., "Partially modified retro-inverso-enkephalinamides: topochemical long-acting analogs in vitro and in vivo", Science 204(4398), 1210-1212 (1979).
Christensen, "A Qualitative Test for Monitoring Coupling Completeness in Solid Phase Peptide Synthesis Using Chloranil.", Acta Chemica Scandinavica B 33, 763-766 (1979).
Clayton, et al., "Bremelanotide for female sexual dysfunctions in premenopausal women: a randomized, placebo-controlled dose-finding trial.", Women's Health 12, 325-337 (2016).
Comps-Agrar, et al., "The oligomeric state sets GABAB receptor signalling efficacy.", EMBO J 30, 2336-2349 (2011).
Corpet, et al., "Multiple sequence alignment with hierarchical clustering.", Nucl Acids Res 16, 10881-10890 (1988).
Cottet, et al., "BRET and time-resolved FRET strategy to study GPCR oligomerization: from cell lines toward native tissues.", Front Endocrinol 3, 92 (2012).
Damian, et al., "Asymmetric conformational changes in a GPCR dimer controlled by G-proteins.", EMBO J 25(24), 5693-5702 (2006).
Danho, "Highly Selective Cyclic Peptides for Human Melanocortin-4 Receptor (MC-4 R): Design, Synthesis, Bioactive Conformation, and Pharmacological Evaluation as an Anti-Obesity Agent", Peptides: The Wave of the Future, 701-703 (2001).
Danho, et al., "Structure-Activity relationship of linear peptide Bu-His6-DPhe7-Arg8-Trp9-Gly10-NH2 at the human melanocortin-1 and -4 receptors: DPhe7 and Trp9 substitution", Bioorg. Med. Chem. Lett. 13(4), 649-652 (2003).

(56) References Cited

OTHER PUBLICATIONS

Daniels, et al., "Opioid-induced tolerance and dependence in mice is modulated by the distance between pharmacophores in a bivalent ligand series.", Proc Natl Acad Sci 102(52), 19208-19213 (2005).
Day, et al., "A new glucagon and GIP-1 co-agonist eliminates obesity in rodents", Nat Chem Biol 5(10), 749-757 (2009).
Deboer, et al., "Cachexia: lessons from melanocortin antagonism.", Trends Endocrinol Metab 17, 199-204 (2006).
Haskell-Luevano, et al., "Discovery of Prototype Peptidomimetic Agonists at the Human Melanocortin Receptors MC1R and MC4R.", J Med Chem 40(14), 2133-2139 (1997).
Haskell-Luevano, et al., "Structure Activity Studies of the Melanocortin-4 Receptor by in Vitro Mutagenesis: Identification of Agouti-Related Protein (AGRP), Melanocortin Agonist and Synthetic Peptide Antagonist Interaction Determinants", Biochemistry 40(20), 6164-6179 (2001).
Haskell-Luevano, et al., "Truncation studies of alpha-melanotropin peptides identify tripeptide analogues exhibiting prolonged agonist bioactivity.", Peptides 17(6), 995-1002 (1996).
Haslach, et al., "Identification of Tetrapeptides from a Mixture Based Positional Scanning Library That Can Restore nM Full Agonist Function of the L106P, I69T, I102S, A219V, C271Y, and C271R Human Melanocortin-4 Polymorphic Receptors (hMC4Rs)", J. Med. Chem. 57(11), 4615-4628 (2014).
Haynes, et al., "Studies on the mechanism of action of the adrenocorticotropic hormone.", J Biol Chem 225, 115-124 (1957).
Haynes, "The activation of adrenal phosphorylase by the adrenocorticotropic hormone", J. Biol. Chem 233(5), 1220-1222 (1958).
Hess, et al., "Backbone cyclic peptidomimetic melanocortin-4 receptor agonist as a novel orally administrated drug lead for treating obesity", J Med Chem 51(4), 1026-1034 (2008).
Higgins, et al., "CLUSTAL: a package for performing multiple sequence alignment on a microcomputer.", Gene 73(1), 237-244 (1988).
Higgins, et al., "Fast and sensitive multiple sequence alignments on a microcomputer.", CABIOS 5(2), 151-153 (1989).
Hiller, et al., "Class A G-Protein-Coupled Receptor (GPCR) Dimers and Bivalent Ligands.", J Med Chem 56, 6542-6559 (2013).
Hlavackova, et al., "Evidence for a single heptahelical domain being turned on upon activation of a dimeric GPCR.", EMBO J 24, 499-509 (2005).
Holder, et al., "Design and pharmacology of peptoids and peptide-peptoid hybrids based on the melanocortin agonists core tetrapeptide sequence", Bioorg. Med. Chem. Lett. 13(24), 4505-4509 (2003).
Holder, et al., "Structure-Activity Relationships of the Melanocortin Tetrapeptide Ac-His-DPhe-Arg-Trp-NH2 at the Mouse Melanocortin Receptors. 1. Modifications at the His Position", J. Med. Chem. 45(13), 2801-2810 (2002).
Holder, et al., "Structure-Activity Relationships of the Melanocortin Tetrapeptide Ac-His-d-Phe-Arg-Trp-NH2 at the Mouse Melanocortin Receptors. 4. Modifications at the Trp Position", J. Med. Chem. 45(26), 5736-5744 (2002).
Holder, et al., "Structure-Activity Relationships of the Melanocortin Tetrapeptide Ac-His-DPhe-Arg-Trp-NH2 at the Mouse Melanocortin Receptors: Part 2 Modifications at the Phe Position.", J Med Chem 45(14), 3073-3081 (2002).
Holder, et al., "Structure-activity relationships of the melanocortin tetrapeptide Ac-His-DPhe-Arg-Trp-NH2 at the mouse melanocortin receptors. Part 3: modifications at the Arg position", Peptides 24(1), 73-82 (2003).
Houghten, "General method for the rapid solid-phase synthesis of large numbers of peptides: specificity of antigen-antibody interaction at the level of individual amino acids", Proc. Natl. Acad. Sci. U.S.A 82(15), 5131-5135 (1985).
Houghten, et al., "Mixture-Based Synthetic Combinatorial Libraries", J. Med. Chem. 42(19), 3743-3778 (1999).
Houghten, et al., "Simplified procedure for carrying out simultaneous multiple hydrogen fluoride cleavages of protected peptide resins", Int. J. Pept. Protein Res. 27(6), 673-678 (1986).
Houghten, et al., "Strategies for the Use of Mixture-Based Synthetic Combinatorial Libraries: Scaffold Ranking, Direct Testing In Vivo, and Enhanced Deconvolution by Computational Methods", J. Comb. Chem. 10(1), 3-19 (2008).
Hruby, et al., "Cyclic lactam .alpha.-melanotropin analogs of Ac-Nle4-cyclo[Asp5,D-Phe7,Lys10]-.alpha.-melanocyte-stimulating hormone-(4-10)-NH2 with bulky aromatic amino acids at position 7 show high antagonist potency and selectivity at specific melanocortin receptors", J. Med. Chem. 38(18), 3454-3461 (1995).
Hruby, et al., "α-Melanotropin: the minimal active sequence in the frog skin bioassay", J. Med. Chem. 30(11), 2126-2130 (1987).
Huang, et al., "Parallelization of a local similarity algorithm.", CABIOS 8(2), 155-165 (1992).
Hunter, et al., "Preparation of Iodine-131 Labelled Human Growth Hormone of High Specific Activity", Nature 194 (4827), 495-496 (1962).
Huszar, et al., "Targeted disruption of the melanocortin-4 receptor results in obesity in mice.", Cell 88(1), 131-141 (1997).
Iglesias, et al., "Serotonin-2A homodimers are needed for signalling via both phospholipase A2 and phospholipase C in transfected CHO cells.", Eur J Pharmacol 800, 63-69 (2017).
Irani, et al., "Implication of the melanocortin-3 receptor in the regulation of food intake.", Eur J Pharmacol 660(1), 80-87 (2011).
Irani, et al., "Progress in the development of melanocortin receptor selective ligands", Current Pharmaceutical Design 10(28), 3443-3479 (2004).
Jackson, et al., "Chimeras of the agouti-related protein: Insights into agonist and antagonist selectivity of melanocortin receptors.", Peptides 26, 1978-1987 (2005).
Jackson, et al., "Design, Pharmacology, and NMR Structure of a Minimized Cystine Knot with Agouti-Related Protein Activity.", Biochemistry 41, 7565-7572 (2002).
Jagadish, et al., "Squalene-derived Flexible Linkers for Bioactive Peptides.", Bioorg Med Chem Lett 17(12), 3310-3313 (2007).
Joppa, et al., "Central administration of peptide and small molecule MC4 receptor antagonists induce hyperphagia in mice and attenuate cytokine-induced anorexia.", Peptides 26, 2294-2301 (2005).
Josan, et al., "Cell-Specific Targeting by Heterobivalent Ligands.", Bioconjugate Chem 22(7), 1270-1278 (2011).
Josan, et al., "Solid-Phase Synthesis of Heterobivalent Ligands Targeted to Melanocortin and Cholecystokinin Receptors.", Int J Pept Res Ther 14, 293-300 (2008).
Joseph, et al., "Chimeric NDP-MSH and MTII melanocortin peptides with agouti-related protein (AGRP) Arg-Phe-Phe amino acids possess agonist melanocortin receptor activity.", Peptides 24(12), 1899-1908 (2003).
Joseph, et al., "Modified melanocortin tetrapeptide Ac-His-dPhe-Arg-Trp-NH at the arginine side chain with ureas and thioureas", J Pept Res 66(5), 297-307 (2005).
Joseph, et al., "Stereochemical Studies of the Monocyclic Agouti-Related Protein (103-122) Arg-Phe-Phe Residues: Conversion of a Melanocortin-4 Receptor Antagonist into an Agonist and Results in the Discovery of a Potent and Selective Melanocortin-1 Agonist", J. Med. Chem. 47(27), 6702-6710 (2004).
Joseph, et al., "γ2-Melanocyte stimulation hormone (γ2-MSH) truncation studies results in the cautionary note that γ2-MSH is not selective for the mouse MC3R over the mouse MC5R", Peptides 31(12), 2304-2313 (2010).
Journe, et al., "N1-linked melatonin dimers as bivalent ligands targeting dimeric melatonin receptors.", Medchemcomm 5, 792-796 (2014).
Kaiser, et al., "Color test for detection of free terminal amino groups in the solid-phase synthesis of peptides.", Anal Biochem 34(2), 595-598 (1970).
Karlin, et al., "Applications and statistics for multiple high-scoring segments in molecular sequences.", Proc Natl Acad Sci 90, 5873-5877 (1993).
Karlin, et al., "Methods for assessing the statistical significance of molecular sequence features by using general scoring schemes.", Proc Natl Acad Sci 87(6), 2264-2268 (1990).
Kavarana, et al., "Novel Cyclic Templates of α-MSH Give Highly Selective and Potent Antagonists/Agonists for Human Melanocortin-3/4 Receptors", J. Med. Chem. 45(12), 2644-2650 (2002).

(56) References Cited

OTHER PUBLICATIONS

Kiefer, et al., "Melanocortin Receptor Binding Determinants in the Agouti Protein", Biochemistry 37(4), 991-997 (1998).

Kingsberg, "Bremelanotide for Hypoactive Sexual Desire Disorder: Analyses from a Phase 2B Does-Ranging Study", 4th International Consultation on Sexual Medicine, J Sex Med 12(suppl 6), 389 (2015).

Kniazeff, et al., "Closed state of both binding domains of homodimeric mGlu receptors is required for full activity.", Nat Struct Mol Biol 11, 706-713 (2004).

Kniazeff, et al., "Locking the Dimeric GABAB G-Protein-Coupled Receptor in Its Active State.", J Neurosci 24, 370-377 (2004).

Koikov, et al., "Sub-nanomolar hMC1R agonists by end-capping of the melanocortin tetrapeptide His-D-Phe-Arg-Trp-NH(2)", Bioorg. Med. Chem. Lett. 13(16), 2647-2650 (2003).

Kopanchuk, et al., "Co-operative regulation of ligand binding to melanocortin receptor subtypes: evidence for interacting binding sites", Eur J Pharmacol 512, 85-95 (2005).

Kopanchuk, et al., "Kinetic evidence for tandemly arranged ligand binding sites in melanocortin 4 receptor complexes.", Neurochem Int 49, 533-542 (2006).

Holder, J , et al., "Characterization of aliphatic, cyclic, and aromatic N-terminally "capped" His-d-Phe-Arg-Trp-NH2 tetrapeptides at the melanocortin receptors", European Journal fo Pharmacology 462, 41-52 (2003).

Joseph, C , et al., "Elongation studies of the human agouti-related protein (AGRP) core decapeptide (Yc[CRFFNAFC]Y) results in antagonism at the mouse melanocortin-3 receptor", Peptides 24, 263-270 (2003).

Topiol, S , "A Surprising Recipe for Designing Biased Ligands", J Med Chem 62, 141-143 (2019).

U.S. Appl. No. 16/542,006, 2020-0115416.

U.S. Appl. No. 17/113,887.

Betts, M , et al., "Amino Acid Properties and Consequences of Substitutions", Bioinformatics for Geneticits, Chapter 14, 289-316 (2003).

Feng, Z , et al., "Inspiration from the mirror: D-amino acid containing peptides in biomedical approaches", BioMol Concepts 7(3), 179-187 (2016).

Friedman, M , "Origin, Microbiology, Nutrition, and Pharmacology of D-Amino Acids", Chemistry and Biodiversity 7, 1491-1530 (2010).

Sela, M , et al., "Different roles of D-amino acids in immune phenomena", The FASEB Journal 11, 449-456 (1997).

Ericson, M , et al., "Arg-Phe-Phe D-Amino Acid Stereochemistry Scan in the Macrocyclic Agouti-Related Protein Antagonist Scaffold c[Pro-Arg-Phe-Phe-Xaa-Ala-Phe-DPro] Results in Unanticipated Melanocortin-1 Receptor Agonist Profiles", ACS Chem Neurosci 9(12), 3015-3023 (2018).

Ericson, M , et al., "Structure-Activity Relationship Studies on a Macrocyclic Agouti-Related Protein (AGRP) Scaffoli Reveal Agouti Signaling Protein (ASP) Residue Substitutions Maintain Melanocortin-4 Receptor Antagonist Potency and Result in Inverse Agonist Pharmacology at . . . ", J Med Chem 60, 8103-8114 (2017).

Fleming, K , et al., "Structure-Activity Relationship Studies of a Macrocyclic AGRP-Mimetic Scaffold c[Pro-Arg-Phe-Phe-Asn-Ala-Phe-DPro] Yield Potent and Selective Melanocortin-4 Receptor Antagonists and Melanocortin-5 Receptor Inverse Agonists that Increase Food Intake in Mice", ACS Chem Neurosci 9(5), 1141-1151 (2018).

Fleming, K , et al., "Synergistic Multi-Residue Substitutions of a Macrocyclic c[Pro-Arg-Phe-Phe-Asn-Ala-Phe-DPro] Agouti-Related Protein (AGRP) Scaffold Yield Potent and >600-Fold MC4R versus MC3R Selective Melanocortin Receptor Antagonists", J Med Chem 61(17), 7729-7740 (2018).

Bednarek, M , et al., "Potent and Selective Agonist of Human Melanocortin Receptor 5: Cyclic Analogues of r-Melanocyte-Stimulating Hormone", J Med Chem 50, 2520-2526 (2007).

Ericson, M, et al., "Discovery of Molecular Interactions of the Human Melanocortin-4 Receptor (hMC4R) Asp189 (D189) Amino Acid with the Endogenous G-Protein-Coupled Receptor (GPCR) Antagonist Agouti-Related Protein (AGRP) Provides Insights to AGRP's Inverse Agonist . . .", ACS Neurosci 12, 542-556 (2021).

Ericson, M, et al., "Peptoid NPhe 4 in AGRP-Based c [Pro 1-Arg 2-Phe 3-Phe 4-Xxx 5-Ala 6-Phe 7-DPro 8] Scaffolds Maintain Mouse MC4R Antagonist Potency", ACS Med Chem Lett 11(10), 1942-1948 (2020).

Koerperich, Z, "Incorporation of Agouti-Related Protein (AgRP) Human Single Nucleotide Polymorphisms (SNPs) in the AgRP-Derived Macrocyclic Scaffold c [Pro-Arg-Phe-Phe-Asn-Ala-Phe-dPro] Decreases Melanocortin-4 Receptor Antagonist Potency and Results in the Discovery . . .", J Med Chem 63(5), 2194-2208 (2020).

\* cited by examiner

CHIMERIC MELANOCORTIN LIGANDS AND METHODS OF USE THEREOF

RELATED APPLICATION

This application claims the benefit of priority of U.S. Provisional Application Ser. No. 62/409,620 filed on Oct. 18, 2016, which application is incorporated by reference herein.

SEQUENCE LISTING

The instant application contains a Sequence Listing which has been submitted in ASCII format via EFS-Web and is hereby incorporated by reference in its entirety. Said ASCII copy, created on Dec. 1, 2017, is named 09531_425US1 SL.txt and is 17,736 bytes in size.

GOVERNMENT FUNDING

This invention was made with government support under R01 DK091906 and R01 DK064250 awarded by the National Institutes of Health. The government has certain rights in the invention.

BACKGROUND OF THE INVENTION

The melanocortin system consists of five receptors, discovered to date, that are members of the family of G protein-coupled receptors (GPCRs) (Chhajlani, V., et al. *Biochem. Biophys. Res. Commun.* 1993, 195, 866-873; Chhajlani, V., et al. *FEBS Lett.* 1992, 309, 417-420; Gantz, I., et al. *J. Biol. Chem.* 1993, 268, 8246-8250; Gantz, I., et al. *J. Biol. Chem.* 1993, 268, 15174-15179; Gantz, I., et al. *Biochem. Biophys. Res. Commun.* 1994, 200, 1214-1220; Griffon, N., et al. *Biochem. Biophys. Res. Commun.* 1994, 200, 1007-1014; Mountjoy, K. G., et al. *Science* 1992, 257, 1248-1251; and Roselli-Rehfuss, L., et al. *Proc. Natl. Acad. Sci. U.S.A.* 1993, 90, 8856-8860), endogenous agonists including the α-melanocyte stimulating hormone (MSH), β-MSH, γ-MSH, and adrenocorticotropic hormone (ACTH) derived from the proopiomelanocortin (POMC) gene transcript (Nakanishi, S., et al. *Nature* 1979, 278, 423-427), and the naturally occurring antagonists agouti and agouti-related protein (AGRP) (Lu, D., et al. *Nature* 1994, 371, 799-802; Ollmann, M. M., et al. *Science* 1997, 278, 135-138; and Yang, Y. K., et al. *Mol. Endocrinol.* 1999, 13, 148-155). These receptors and ligands are purported to be important in numerous biological pathways, including pigmentation (Allen, B. M. *Science* 1916, 44, 755-758; and Smith, P. E. *Science* 1916, 44, 280-282), steroidogenesis (Haynes, R. C., Jr., et al. *J. Biol. Chem.* 1957, 225, 115-124), and energy homeostasis (Huszar, D., et al. *Cell* 1997, 88, 131-141). In particular, knock-out of the melanocortin 3- and 4-receptors (MC3R, MC4R) in mice alters metabolic phenotypes, with MC3R deficient mice possessing normal body weight accompanied by an increase in fat mass, while disrupting the MC4R results in hyperphagia and obesity in mice (Huszar, D., et al. *Cell* 1997, 88, 131-141; Butler, A. A., et al. *Endocrinol.* 2000, 141, 3518-3521; and Chen, A. S., et al. *Nat. Genet.* 2000, 26, 97-102). Mutations in the MC4R in humans have also been shown to result in obesity; in one study, 5.8% of individuals with severe childhood obesity were found to have mutations in the MC4R (Farooqi, I. S., et al. *N. Engl. J. Med.* 2003, 348, 1085-1095). Mice may therefore serve as a translation model for MC4R-related obesity in humans due to the similar hyperphagic, over-weight phenotype observed. Central administration of the nonselective melanocortin agonists α-MSH (Poggioli, R., et al. *Peptides* 1986, 7, 843-848), NDP-MSH (Brown, K. S., et al. *Regul. Peptides* 1998, 78, 89-94), and MT-II (Fan, W., et al. *Nature* 1997, 385, 165-168; and Irani, B. G., et al. *Eur. J. Pharmacol.* 2011, 660, 80-87) through an intracerebroventricular (i.c.v.) injection decrease food intake in rodents, while injection of the synthetic SHU9119 (Fan, W., et al. *Nature* 1997, 385, 165-168) and endogenous AGRP (Irani, B. G., et al. *Eur. J. Pharmacol.* 2011, 660, 80-87; and Ebihara, K., et al. *Diabetes* 1999, 48, 2028-2033) MC3R/MC4R antagonists increase food consumption. With estimated global obesity rates more than doubling from 1980 to 2014 (World Health Organization (2016) Obesity and overweight fact sheet), the development of novel probes to investigate the etiology of obesity and serve as potential therapeutic leads may be important in efforts to decrease this trend. While MC4R-selective agonists based upon the endogenous melanocortin agonists have previously been investigated, off-target effects including increased blood pressure and increased erectile activity have limited their clinical utility (Greenfield, J. R., et al. *New Engl. J. Med.* 2009, 360, 44-52). Therefore, there is a need for new melanocortin ligands. Specifically, there is a need for MC4-R ligands (e.g., selective MC4-R ligands) with less undesired side effects.

SUMMARY OF THE INVENTION

This invention provides new melanocortin ligands. Accordingly, certain embodiments of the invention provide a cyclic compound of formula I:

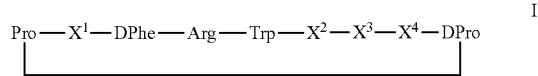

wherein:
Pro is a residue of L-proline, wherein the pyrrolidinyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

DPhe is a residue of D-phenylalanine, wherein the phenyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

Arg is a residue of L-arginine;

Trp is a residue of L-tryptophan, wherein the indolyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

DPro is a residue of D-proline, wherein the pyrrolidinyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

$X^1$ is a direct bond or a residue of an amino acid, dipeptide or tripeptide;

$X^2$ is a direct bond or a residue of an amino acid;

$X^3$ is a direct bond or a residue of an amino acid;

$X^4$ is a direct bond or a residue of an amino acid, dipeptide or tripeptide; wherein when $X^1$, $X^2$, $X^3$ or $X^4$ is a residue of a lysine or comprises a residue of a lysine, the side-chain amine of the lysine is optionally linked through an amide bond to the carboxy terminus of an amino acid or the carboxy terminus of a peptide that is 2, 3, or 4 amino acids in length, and wherein the amino acid or peptide linked to the lysine is optionally acylated;

or a salt thereof.

The invention also provides a pharmaceutical composition comprising a compound of formula I or a pharmaceutically acceptable salt thereof, and a pharmaceutically acceptable carrier.

The invention also provides a method of modulating the activity of a melanocortin receptor in vitro or in vivo comprising contacting the receptor with an effective amount of a compound of formula I, or a pharmaceutically acceptable salt thereof.

The invention also provides method of modulating metabolic activity and/or modulating appetite in an animal in need thereof, comprising administering an effective amount of a compound of formula I, or a pharmaceutically acceptable salt thereof, to the animal.

The invention also provides a method for treating obesity or a disease associated with obesity in an animal (e.g., a mammal, such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of obesity or a disease associated with obesity.

The invention also provides the use of a compound of formula I or a pharmaceutically acceptable salt thereof to prepare a medicament for treating obesity or a disease associated with obesity.

The invention also provides processes and intermediates disclosed herein that are useful for preparing a compound of formula I or a salt thereof.

DETAILED DESCRIPTION

Figure 1A:
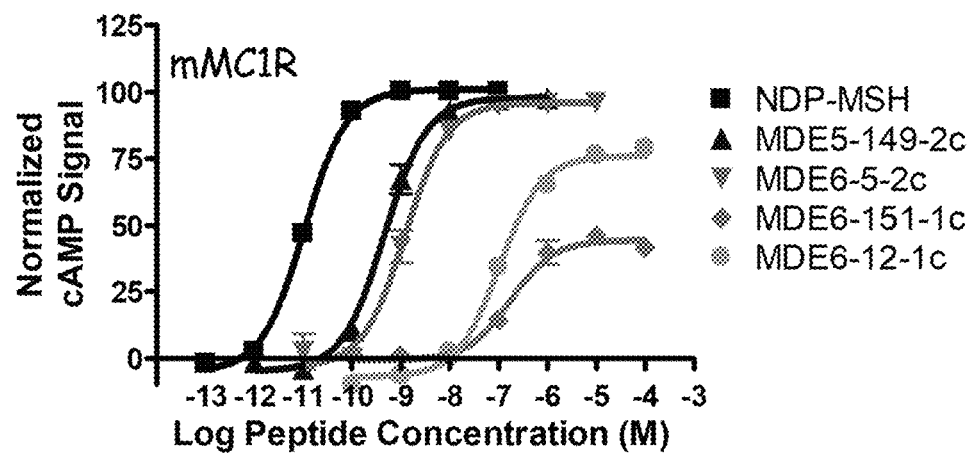
FIGS. 1A-1D illustrate the in vitro pharmacology of NDP-MSH, MDE5-149-2c, MDE6-5-2c, MDE5-151-1c, and MDE6-12-1c at mMC1R (FIG. 1A), mMC3R (FIG. 1B), mMC4R (FIG. 1C), and mMC5R (FIG. 1D).
Figure 1B:
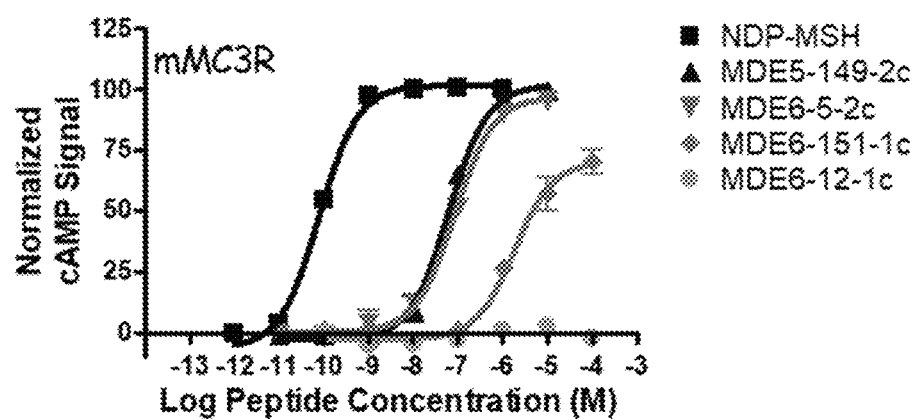
Figure 1C:
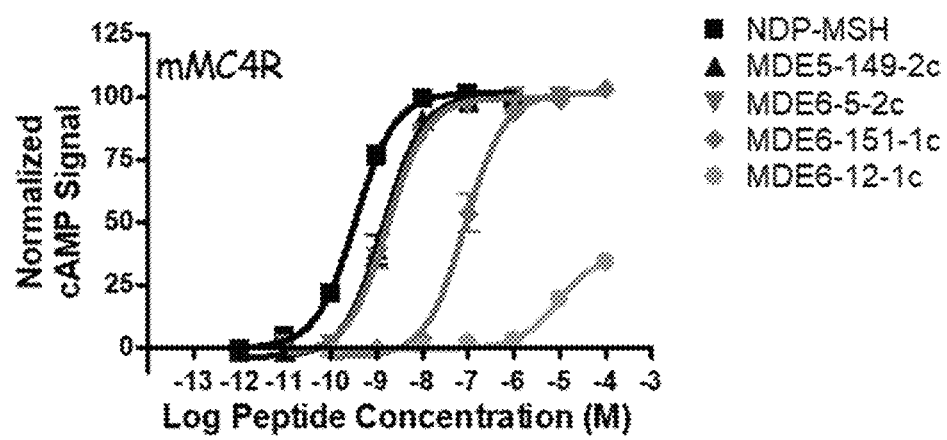
Figure 1D:
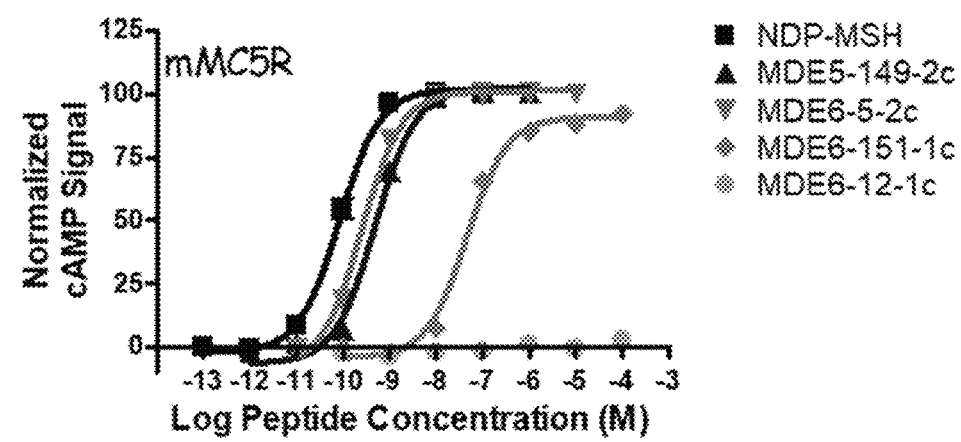

Certain embodiments of the invention provide a cyclic compound of formula I:

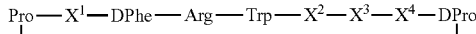

I wherein:

Pro is a residue of L-proline, wherein the pyrrolidinyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

DPhe is a residue of D-phenylalanine, wherein the phenyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

Arg is a residue of L-arginine;

Trp is a residue of L-tryptophan, wherein the indolyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

DPro is a residue of D-proline, wherein the pyrrolidinyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

$X^1$ is a direct bond or a residue of an amino acid, dipeptide or tripeptide;

$X^2$ is a direct bond or a residue of an amino acid;

$X^3$ is a direct bond or a residue of an amino acid;

$X^4$ is a direct bond or a residue of an amino acid, dipeptide or tripeptide;

wherein when $X^1$, $X^2$, $X^3$ or $X^4$ is a residue of a lysine or comprises a residue of a lysine, the side-chain amine of the lysine is optionally linked through an amide bond to the carboxy terminus of an amino acid or the carboxy terminus of a peptide that is 2, 3, or 4 amino acids in length, and wherein the amino acid or peptide linked to the lysine is optionally acylated;

or a salt thereof.

Certain embodiments of the invention provide a cyclic compound of formula I:

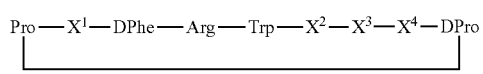

I wherein:

Pro is a residue of L-proline, wherein the pyrrolidinyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

DPhe is a residue of D-phenylalanine, wherein the phenyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

Arg is a residue of L-arginine;

Trp is a residue of L-tryptophan, wherein the indolyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

DPro is a residue of D-proline, wherein the pyrrolidinyl ring is optionally substituted with one or more halo groups, $(C_1\text{-}C_4)$alkyl, $-O(C_1\text{-}C_4)$alkyl, $(C_1\text{-}C_4)$haloalkyl, or $-O(C_1\text{-}C_4)$haloalkyl;

$X^1$ is a direct bond or a residue of an amino acid, dipeptide or tripeptide;

$X^2$ is a direct bond or a residue of an amino acid;

$X^3$ is a direct bond or a residue of an amino acid;

$X^4$ is a direct bond or a residue of an amino acid, dipeptide or tripeptide; or a salt thereof.

In one embodiment, Pro is a residue of L-proline. In one embodiment, Pro is a residue of L-proline, wherein the pyrrolidinyl ring is substituted with one or more halo groups, $(C_1-C_4)$alkyl, —O$(C_1-C_4)$alkyl, $(C_1-C_4)$haloalkyl, or —O$(C_1-C_4)$haloalkyl.

In one embodiment, DPro is a residue of D-proline. In one embodiment, DPro is a residue of D-proline, wherein the pyrrolidinyl ring is substituted with one or more halo groups, $(C_1-C_4)$alkyl, —O$(C_1-C_4)$alkyl, $(C_1-C_4)$haloalkyl, or —O$(C_1-C_4)$haloalkyl.

In one embodiment, Pro is a residue of L-proline and DPro is a residue of D-proline.

In one embodiment, DPhe is a residue of D-phenylalanine. In one embodiment, DPhe is a residue of D-phenylalanine, wherein the phenyl ring is substituted with one or more halo groups, $(C_1-C_4)$alkyl, —O$(C_1-C_4)$alkyl, $(C_1-C_4)$haloalkyl, or —O$(C_1-C_4)$haloalkyl.

In one embodiment, Trp is a residue of L-tryptophan. In one embodiment, Trp is a residue of L-tryptophan, wherein the indolyl ring is substituted with one or more halo groups, $(C_1-C_4)$alkyl, —O$(C_1-C_4)$alkyl, $(C_1-C_4)$haloalkyl, or —O$(C_1-C_4)$haloalkyl.

In one embodiment, Arg is a residue of L-arginine.

In one embodiment, Pro is a residue of L-proline; DPro is a residue of D-proline; DPhe is a residue of D-phenylalanine; Trp is a residue of L-tryptophan; and/or Arg is a residue of L-arginine.

In one embodiment, $X^1$ is a direct bond.

In one embodiment, $X^1$ is a residue of an amino acid, dipeptide or tripeptide. In one embodiment, $X^1$ is a residue of an amino acid. In one embodiment, $X^1$ is a residue of a dipeptide. In one embodiment, $X^1$ is a residue of a tripeptide. In one embodiment, $X^1$ is a residue of a D amino acid. In one embodiment, $X^1$ comprises at least one residue of a D amino acid. In one embodiment, $X^1$ is a residue of an L amino acid. In one embodiment, $X^1$ comprises at least one residue of an L amino acid. In one embodiment, $X^1$ is a residue of a natural amino acid. In one embodiment, $X^1$ comprises at least one residue of a natural amino acid. In one embodiment, $X^1$ comprises at least one residue of a non-natural amino acid.

In one embodiment, $X^1$ is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr. In one embodiment, $X^1$ comprises at least one residue of an amino acid selected from the group consisting L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^1$ is a residue of L-histidine.

In one embodiment, $X^1$ is a residue of lysine (e.g., L-lysine). In one embodiment, $X^1$ is a residue of a dipeptide or a tripeptide which comprises a residue of lysine (e.g., L-lysine). In one embodiment, the side-chain of the lysine is linked through an amide bond to the carboxy terminus of an amino acid or the carboxy terminus of a peptide that is 2, 3, or 4 amino acids in length. In one embodiment, the side-chain of the lysine is linked through an amide bond to the carboxy terminus of an amino acid. In one embodiment, the side-chain of the lysine is linked through an amide bond to the carboxy terminus of a peptide that is 2, 3, or 4 amino acids in length. In one embodiment, the side-chain of the lysine is linked through an amide bond to the carboxy terminus of a peptide that is 2 amino acids in length. In one embodiment, the side-chain of the lysine is linked through an amide bond to the carboxy terminus of a peptide that is 3 amino acids in length. In one embodiment, the side-chain of the lysine is linked through an amide bond to the carboxy terminus of a peptide that is 4 amino acids in length. In one embodiment, the amine terminus of the amino acid or peptide linked to the lysine is acylated.

In one embodiment, the side-chain of the lysine is linked through an amide bond to the carboxy terminus of an arginine (e.g., L-arginine). In one embodiment, the amine terminus of the arginine is acylated.

In one embodiment, the side-chain of the lysine is linked through an amide bond to the carboxy terminus of an Arg-Arg dipeptide. In one embodiment, the amine terminus of the dipeptide is acylated.

In one embodiment, the side-chain of the lysine is linked through an amide bond to the carboxy terminus of an Arg-Arg-Arg tripeptide. In one embodiment, the amine terminus of the tripeptide is acylated.

In one embodiment, $X^2$ is a direct bond.

In one embodiment, $X^2$ is a residue of an amino acid. In one embodiment, $X^2$ is a residue of a D amino acid. In one embodiment, $X^2$ is a residue of an L amino acid. In one embodiment, $X^2$ is a residue of a natural amino acid. In one embodiment, $X^2$ is a residue of a non-natural amino acid.

In one embodiment, $X^2$ is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^2$ is a residue of L-lysine, L-asparagine or L-diaminopropionic acid. In one embodiment, $X^2$ is a residue of L-asparagine or L-diaminopropionic acid. In one embodiment, $X^2$ is a residue of L-asparagine. In one embodiment, $X^2$ is a residue of L-diaminopropionic acid.

In one embodiment, $X^2$ is a residue of lysine (e.g., L-lysine). In one embodiment, the side-chain of the lysine is linked through an amide bond to the carboxy terminus of an amino acid or the carboxy terminus of a peptide that is 2, 3, or 4 amino acids in length. In one embodiment, the side-chain of the lysine is linked through an amide bond to the carboxy terminus of an amino acid. In one embodiment, the side-chain of the lysine is linked through an amide bond to the carboxy terminus of a peptide that is 2, 3, or 4 amino acids in length. In one embodiment, the side-chain of the lysine is linked through an amide bond to the carboxy terminus of a peptide that is 2 amino acids in length. In one embodiment, the side-chain of the lysine is linked through an amide bond to the carboxy terminus of a peptide that is 3 amino acids in length. In one embodiment, the side-chain of the lysine is linked through an amide bond to the carboxy terminus of a peptide that is 4 amino acids in length. In one embodiment, the amine terminus of the amino acid or peptide linked to the lysine is acylated.

In one embodiment, the side-chain of the lysine is linked through an amide bond to the carboxy terminus of an arginine (e.g., L-arginine). In one embodiment, the amine terminus of the arginine is acylated.

In one embodiment, the side-chain of the lysine is linked through an amide bond to the carboxy terminus of an Arg-Arg dipeptide. In one embodiment, the amine terminus of the dipeptide is acylated.

In one embodiment, the side-chain of the lysine is linked through an amide bond to the carboxy terminus of an Arg-Arg-Arg tripeptide. In one embodiment, the amine terminus of the tripeptide is acylated.

In one embodiment, $X^3$ is a direct bond.

In one embodiment, $X^3$ is a residue of an amino acid. In one embodiment, $X^3$ is a residue of a D amino acid. In one embodiment, $X^3$ is a residue of an L amino acid. In one embodiment, $X^3$ is a residue of a natural amino acid. In one embodiment, $X^3$ is a residue of a non-natural amino acid.

In one embodiment, $X^3$ is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^3$ is a residue of L-alanine, L-lysine, L-asparagine or L-diaminopropionic acid. In one embodiment, wherein $X^3$ is a residue of L-asparagine. In one embodiment, wherein $X^3$ is a residue of L-diaminopropionic acid.

In one embodiment, $X^3$ is a residue of L-alanine or L-lysine.

In one embodiment, $X^3$ is a residue of L-alanine.

In one embodiment, $X^3$ is a residue of lysine (e.g., L-lysine). In one embodiment, the side-chain of the lysine is linked through an amide bond to the carboxy terminus of an amino acid or the carboxy terminus of a peptide that is 2, 3, or 4 amino acids in length. In one embodiment, the side-chain of the lysine is linked through an amide bond to the carboxy terminus of an amino acid. In one embodiment, the side-chain of the lysine is linked through an amide bond to the carboxy terminus of a peptide that is 2, 3, or 4 amino acids in length. In one embodiment, the side-chain of the lysine is linked through an amide bond to the carboxy terminus of a peptide that is 2 amino acids in length. In one embodiment, the side-chain of the lysine is linked through an amide bond to the carboxy terminus of a peptide that is 3 amino acids in length. In one embodiment, the side-chain of the lysine is linked through an amide bond to the carboxy terminus of a peptide that is 4 amino acids in length. In one embodiment, the amine terminus of the amino acid or peptide linked to the lysine is acylated.

In one embodiment, the side-chain of the lysine is linked through an amide bond to the carboxy terminus of an arginine (e.g., L-arginine). In one embodiment, the amine terminus of the arginine is acylated.

In one embodiment, the side-chain of the lysine is linked through an amide bond to the carboxy terminus of an Arg-Arg dipeptide. In one embodiment, the amine terminus of the dipeptide is acylated.

In one embodiment, the side-chain of the lysine is linked through an amide bond to the carboxy terminus of an Arg-Arg-Arg tripeptide. In one embodiment, the amine terminus of the tripeptide is acylated.

In one embodiment, $X^4$ is a direct bond.

In one embodiment, $X^4$ is a residue of an amino acid, dipeptide or tripeptide. In one embodiment, $X^4$ is a residue of an amino acid. In one embodiment, $X^4$ is a residue of a dipeptide. In one embodiment, $X^4$ is a residue of a tripeptide. In one embodiment, $X^4$ is a residue of a D amino acid. In one embodiment, $X^4$ comprises at least one residue of a D amino acid. In one embodiment, $X^4$ is a residue of an L amino acid. In one embodiment, $X^4$ comprises at least one residue of an L amino acid. In one embodiment, $X^4$ is a residue of a natural amino acid. In one embodiment, $X^4$ comprises at least one residue of a natural amino acid. In one embodiment, $X^4$ is a residue of a non-natural amino acid. In one embodiment, $X^4$ comprises at least one residue of a non-natural amino acid.

In one embodiment, $X^4$ is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr. In one embodiment, $X^4$ comprises at least one residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^4$ is a residue of L-phenylalanine, L-alanine, L-lysine, L-asparagine or L-diaminopropionic acid. In one embodiment, $X^4$ is a residue of L-phenylalanine. In one embodiment, $X^4$ is a residue of L-alanine. In one embodiment, $X^4$ is a residue of L-lysine. In one embodiment, $X^4$ is a residue of L-asparagine. In one embodiment, $X^4$ is a residue of L-diaminopropionic acid.

In one embodiment, $X^4$ is a residue of lysine (e.g., L-lysine). In one embodiment, $X^4$ is a residue of a dipeptide or a tripeptide which comprises a residue of lysine (e.g., L-lysine). In one embodiment, the side-chain of the lysine is linked through an amide bond to the carboxy terminus of an amino acid or the carboxy terminus of a peptide that is 2, 3, or 4 amino acids in length. In one embodiment, the side-chain of the lysine is linked through an amide bond to the carboxy terminus of an amino acid. In one embodiment, the side-chain of the lysine is linked through an amide bond to the carboxy terminus of a peptide that is 2, 3, or 4 amino acids in length. In one embodiment, the side-chain of the lysine is linked through an amide bond to the carboxy terminus of a peptide that is 2 amino acids in length. In one embodiment, the side-chain of the lysine is linked through an amide bond to the carboxy terminus of a peptide that is 3 amino acids in length. In one embodiment, the side-chain of the lysine is linked through an amide bond to the carboxy terminus of a peptide that is 4 amino acids in length. In one embodiment, the amine terminus of the amino acid or peptide linked to the lysine is acylated.

In one embodiment, the side-chain of the lysine is linked through an amide bond to the carboxy terminus of an arginine (e.g., L-arginine). In one embodiment, the amine terminus of the arginine is acylated.

In one embodiment, the side-chain of the lysine is linked through an amide bond to the carboxy terminus of an Arg-Arg dipeptide. In one embodiment, the amine terminus of the dipeptide is acylated.

In one embodiment, the side-chain of the lysine is linked through an amide bond to the carboxy terminus of an Arg-Arg-Arg tripeptide. In one embodiment, the amine terminus of the tripeptide is acylated.

In one embodiment, $X^2$, $X^3$ and $X^4$ are direct bonds and $X^1$ is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^3$ and $X^4$ are direct bonds, $X^1$ and $X^2$ are residues of an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^4$ is a direct bond, $X^1$, $X^2$ and $X^3$ are residues of an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^1$, $X^2$, $X^3$ and $X^4$ are residues of an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^1$, $X^2$, $X^3$ and $X^4$ are direct bonds.

In one embodiment, $X^1$, $X^3$ and $X^4$ are direct bonds, and $X^2$ is a residue of an amino acid selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^1$ and $X^4$ are direct bonds and $X^2$ and $X^3$ are residues of an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

In one embodiment, $X^1$ is a direct bond and $X^2$, $X^3$ and $X^4$ are residues of an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2) D-Phe, 2-L-Nal, 2-D-Nal, β-Ala, ε-Aminocaproic acid, Met [O2], dehydPro, and (3I)Tyr.

In one embodiment, $X^3$ is a residue of L-lysine and $X^1$, $X^2$, and $X^4$ are residues of an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr. In one embodiment, the side-chain of the lysine is linked through an amide bond to the carboxy terminus of an amino acid or the carboxy terminus of a peptide that is 2, 3, or 4 amino acids in length. In one embodiment, the amine terminus of the amino acid or peptide linked to the lysine is acylated. In one embodiment, the amino acid linked to the lysine is L-arginine or the peptide linked to the lysine comprises one, two, three or four L-arginines.

In one embodiment, $X^3$ is a residue of L-lysine, $X^4$ is a direct bond and $X^1$ and $X^2$ are residues of an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I) Tyr. In one embodiment, the side-chain of the lysine is linked through an amide bond to the carboxy terminus of an amino acid or the carboxy terminus of a peptide that is 2, 3, or 4 amino acids in length. In one embodiment, the amine terminus of the amino acid or peptide linked to the lysine is acylated. In one embodiment, the amino acid linked to the lysine is L-arginine or the peptide linked to the lysine comprises one, two, three or four L-arginines.

In one embodiment, Pro is a residue of L-proline; $X^1$ is a residue of L-Histidine; DPhe is a residue of D-phenylalanine; Arg is a residue of L-arginine; Trp is a residue of L-tryptophan; $X^2$ is a residue of L-asparagine or L-diaminopropionic acid; $X^3$ is a residue of an amino acid; $X^4$ is a direct bond or a residue of an amino acid, dipeptide or tripeptide; and DPro is a residue of D-proline.

In one embodiment, Pro is a residue of L-proline; $X^1$ is a residue of L-Histidine; DPhe is a residue of D-phenylalanine; Arg is a residue of L-arginine; Trp is a residue of L-tryptophan; $X^2$ is a residue of L-asparagine or L-diaminopropionic acid; $X^3$ is a residue of a residue of L-alanine or L-lysine; $X^4$ is a direct bond or a residue of an amino acid, dipeptide or tripeptide; and DPro is a residue of D-proline.

In one embodiment, Pro is a residue of L-proline; $X^1$ is a residue of L-Histidine; DPhe is a residue of D-phenylalanine; Arg is a residue of L-arginine; Trp is a residue of L-tryptophan; $X^2$ is a residue of L-asparagine or L-diaminopropionic acid; $X^3$ is a residue of L-alanine; $X^4$ is a direct bond or a residue of phenylalanine; and DPro is a residue of D-proline.

In one embodiment, Pro is a residue of L-proline; $X^1$ is a residue of L-Histidine; DPhe is a residue of D-phenylalanine; Arg is a residue of L-arginine; Trp is a residue of L-tryptophan; $X^2$ is a residue of L-asparagine or L-diaminopropionic acid; $X^3$ is a residue of L-lysine; $X^4$ is a direct bond or a residue of phenylalanine; and DPro is a residue of D-proline. In one embodiment, the side-chain of the lysine is linked through an amide bond to the carboxy terminus of an amino acid or the carboxy terminus of a peptide that is 2, 3, or 4 amino acids in length. In one embodiment, the amine terminus of the amino acid or peptide linked to the lysine is acylated. In one embodiment, the amino acid linked to the lysine is L-arginine or the peptide linked to the lysine comprises one, two, three or four L-arginines.

In one embodiment, the compound of invention is selected from the group consisting of:

```
                                              (SEQ ID NO: 1)
c[Pro-His-DPhe-Arg-Trp-Asn-Ala-Phe-DPro];

(SEQ ID NO: 2)
c[Pro-His-DPhe-Arg-Trp-Dap-Ala-Phe-DPro];

(SEQ ID NO: 3)
c[Pro-His-DPhe-Arg-Trp-Asn-Ala-DPro];

(SEQ ID NO: 4)
c[Pro-His-DPhe-Arg-Trp-Dap-Ala-DPro];

(SEQ ID NO: 5)
c[Pro-His-DPhe-Arg-Trp-Asn-DPro];

(SEQ ID NO: 6)
c[Pro-His-DPhe-Arg-Trp-Dap-DPro];

(SEQ ID NO: 7)
c[Pro-His-DPhe-Arg-Trp-DPro];

(SEQ ID NO: 8)
c[Pro-DPhe-Arg-Trp-Asn-Ala-Phe-DPro];

(SEQ ID NO: 9)
c[Pro-DPhe-Arg-Trp-Dap-Ala-Phe-DPro];

(SEQ ID NO: 10)
c[Pro-DPhe-Arg-Trp-Asn-Ala-DPro];

(SEQ ID NO: 11)
c[Pro-DPhe-Arg-Trp-Dap-Ala-DPro];

(SEQ ID NO: 12)
c[Pro-DPhe-Arg-Trp-Asn-DPro];

(SEQ ID NO: 13)
c[Pro-DPhe-Arg-Trp-Dap-DPro];

(SEQ ID NO: 14)
c[Pro-DPhe-Arg-Trp-DPro];

(SEQ ID NO: 34)
c[Pro-His-DPhe-Arg-Trp-Asn-Lys-Phe-DPro];

(SEQ ID NO: 35)
c[Pro-His-DPhe-Arg-Trp-Asn-Lys(Ac-Arg)-Phe-DPro];

(SEQ ID NO: 36)
c[Pro-His-DPhe-Arg-Trp-Asn-Lys(Ac-Arg-Arg)-Phe-
DPro];

(SEQ ID NO: 37)
c[Pro-His-DPhe-Arg-Trp-Asn-Lys(Ac-Arg-Arg-Arg)-
Phe-DPro];

(SEQ ID NO: 38)
c[Pro-His-DPhe-Arg-Trp-Dap-Lys-DPro];
```

```
                                              (SEQ ID NO: 39)
c[Pro-His-DPhe-Arg-Trp-Dap-Lys(Ac-Arg)-DPro];

(SEQ ID NO: 40)
c[Pro-His-DPhe-Arg-Trp-Dap-Lys(Ac-Arg-Arg)-DPro];

(SEQ ID NO: 41)
c]Pro-His-DPhe-Arg-Trp-Dap-Lys(Ac-Arg-Arg-Arg)-
DPro];
``` and salts thereof. Within the peptide sequences shown above, certain amino acids are shown within parentheses following a lysine residue. As used herein, this nomenclature indicates that the side-chain of the lysine is linked through an amide bond to the carboxy terminus of the amino acid shown in parentheses or to the carboxy terminus of the peptide shown in parentheses. "Ac" indicates that the amine terminus of the amino acid or peptide linked to the lysine is acylated.

In one embodiment, the compound of invention is selected from the group consisting of:

```
                                              (SEQ ID NO: 1)
c[Pro-His-DPhe-Arg-Trp-Asn-Ala-Phe-DPro];

(SEQ ID NO: 2)
c[Pro-His-DPhe-Arg-Trp-Dap-Ala-Phe-DPro];

(SEQ ID NO: 3)
c[Pro-His-DPhe-Arg-Trp-Asn-Ala-DPro];

(SEQ ID NO: 4)
c[Pro-His-DPhe-Arg-Trp-Dap-Ala-DPro];

(SEQ ID NO: 5)
c[Pro-His-DPhe-Arg-Trp-Asn-DPro];

(SEQ ID NO: 6)
c[Pro-His-DPhe-Arg-Trp-Dap-DPro];

(SEQ ID NO: 7)
c[Pro-His-DPhe-Arg-Trp-DPro];

(SEQ ID NO: 8)
c[Pro-DPhe-Arg-Trp-Asn-Ala-Phe-DPro];

(SEQ ID NO: 9)
c[Pro-DPhe-Arg-Trp-Dap-Ala-Phe-DPro];

(SEQ ID NO: 10)
c[Pro-DPhe-Arg-Trp-Asn-Ala-DPro];

(SEQ ID NO: 11)
c[Pro-DPhe-Arg-Trp-Dap-Ala-DPro];

(SEQ ID NO: 12)
c[Pro-DPhe-Arg-Trp-Asn-DPro];

(SEQ ID NO: 13)
c[Pro-DPhe-Arg-Trp-Dap-DPro];
and (SEQ ID NO: 14)
c[Pro-DPhe-Arg-Trp-DPro];
``` and salts thereof.

In one embodiment, a compound of the invention is selected from the group consisting of

```
                                              (SEQ ID NO: 34)
c[Pro-His-DPhe-Arg-Trp-Asn-Lys-Phe-DPro];

(SEQ ID NO: 35)
c[Pro-His-DPhe-Arg-Trp-Asn-Lys(Ac-Arg)-Phe-DPro];

(SEQ ID NO: 36)
c[Pro-His-DPhe-Arg-Trp-Asn-Lys(Ac-Arg-Arg)-Phe-
DPro];

(SEQ ID NO: 37)
c[Pro-His-DPhe-Arg-Trp-Asn-Lys(Ac-Arg-Arg-Arg)-
Phe-DPro];

(SEQ ID NO: 38)
c[Pro-His-DPhe-Arg-Trp-Dap-Lys-DPro];

(SEQ ID NO: 39)
c[Pro-His-DPhe-Arg-Trp-Dap-Lys(Ac-Arg)-DPro];

(SEQ ID NO: 40)
c[Pro-His-DPhe-Arg-Trp-Dap-Lys(Ac-Arg-Arg)-DPro];

(SEQ ID NO: 41)
c[Pro-His-DPhe-Arg-Trp-Dap-Lys(Ac-Arg-Arg-Arg)-
DPro];
``` and salts thereof.

In one embodiment, a compound of the invention is selected from the group consisting of:

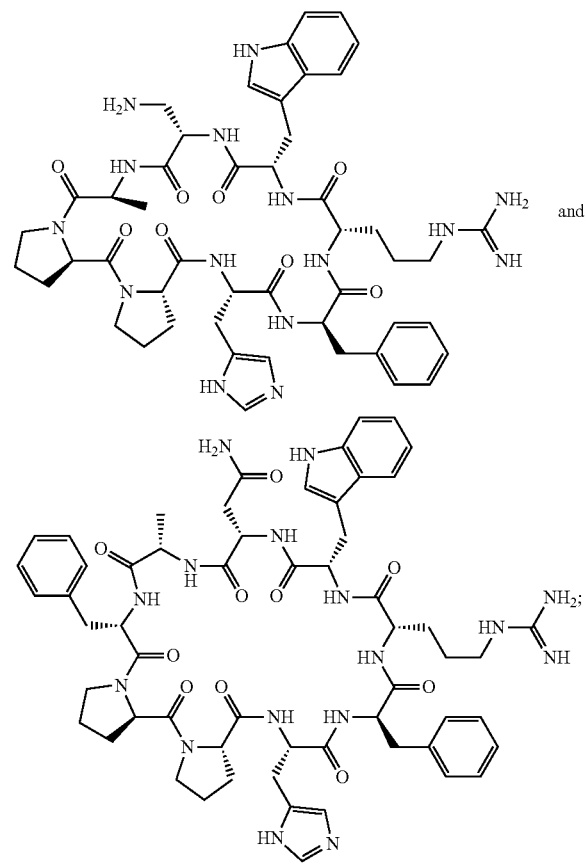

and salts thereof.

In one embodiment, a compound of the invention is selected from the group consisting of (SEQ ID NOS 34-37, respectively, in order of appearance):

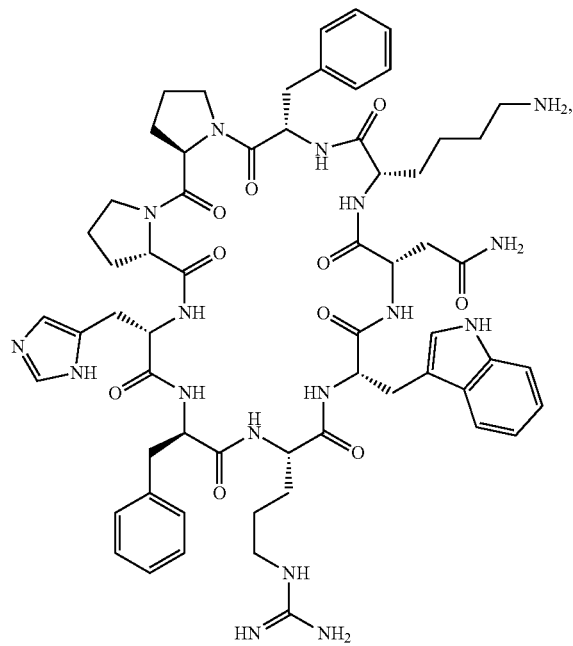
c[Pro-His-DPhe-Arg-Trp-Asn-Lys-Phe-DPro]
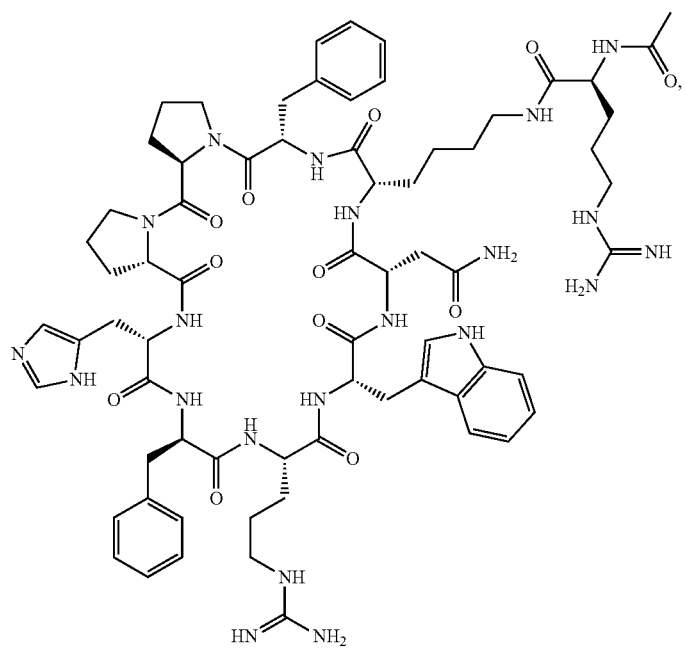
c[Pro-His-DPhe-Arg-Trp-Asn-Lys(Ac-Arg)-Phe-DPro]

-continued
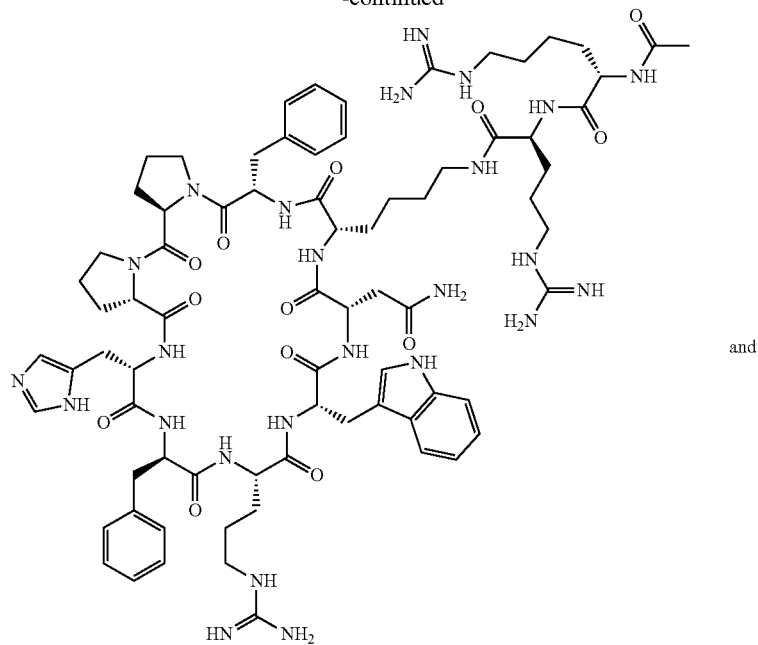
c[Pro-His-DPhe-Arg-Trp-Asn-Lys(Ac-Arg-Arg)-Phe-DPro]
and
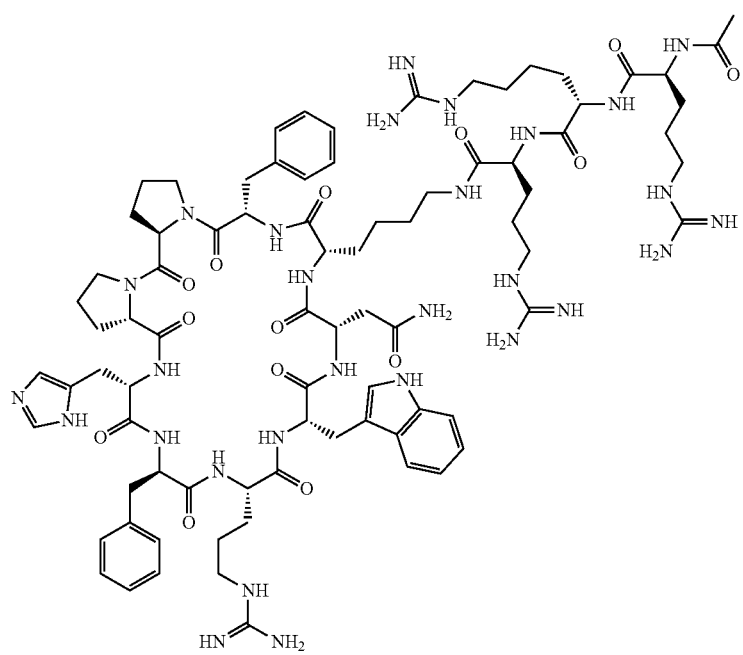
c[Pro-His-DPhe-Arg-Trp-Asn-Lys(Ac-Arg-Arg-Arg)-Phe-DPro]
and salts thereof.

In one embodiment, a compound of the invention is selected from the group consisting of (SEQ ID NOS 38-41, respectively, in order of appearance):
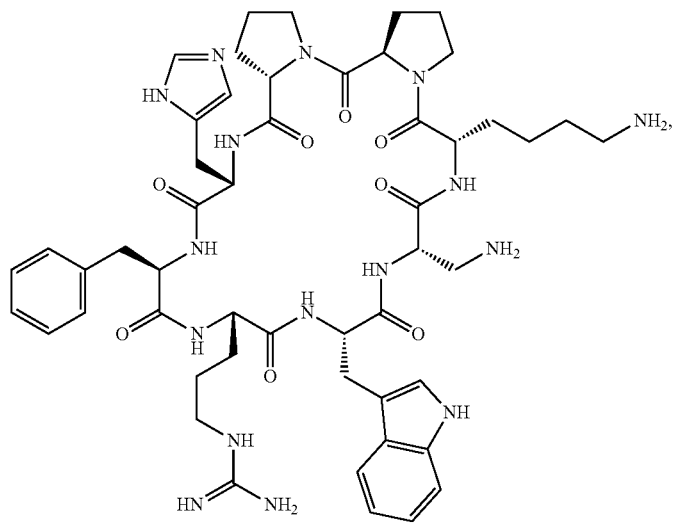
c[Pro-His-DPhe-Arg-Trp-Dap-Lys-DPro]
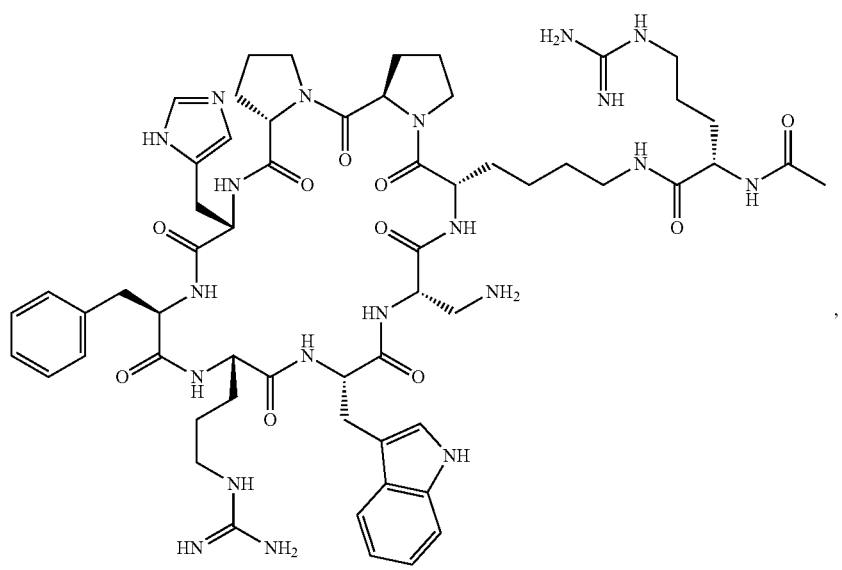
c[Pro-His-DPhe-Arg-Trp-Dap-Lys(Ac-Arg)-DPro]

-continued

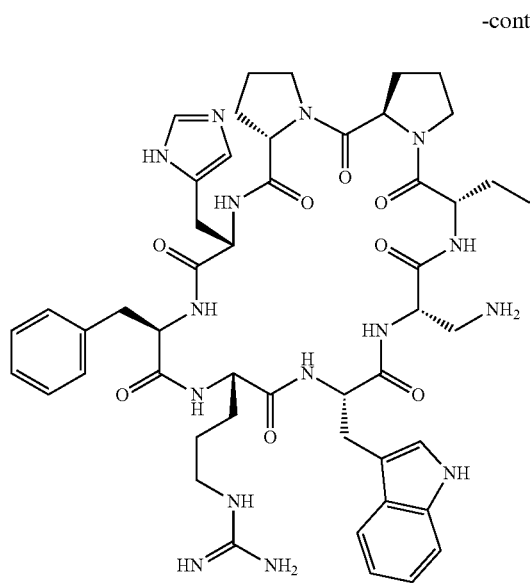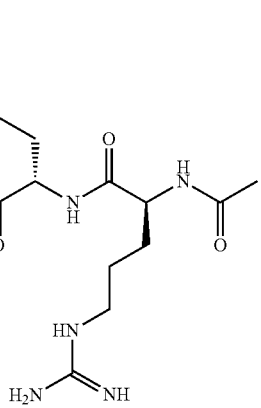

c[Pro-His-DPhe-Arg-Trp-Dap-Lys(Ac-Arg-Arg)-DPro]

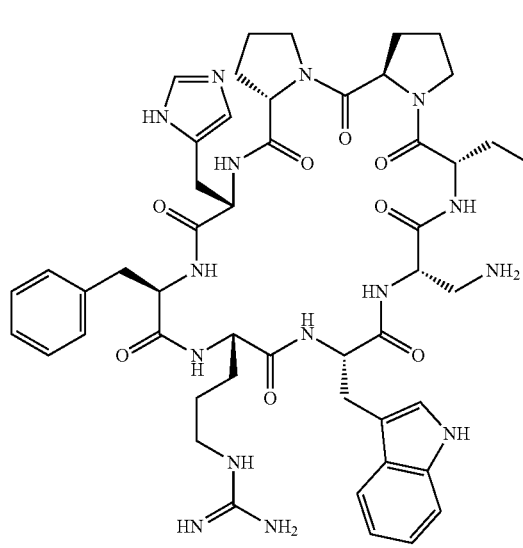

c[Pro-His-DPhe-Arg-Trp-Dap-Lys(Ac-Arg-Arg-Arg)-DPro]

and salts thereof.

In one embodiment, the compound of invention is a cyclic peptide, comprising an amino acid sequence having at least 80% sequence identity to:

```
                                    (SEQ ID NO: 15)
His-DPhe-Arg-Trp-Asn, (SEQ ID NO: 16)
His-DPhe-Arg-Trp-Dap, (SEQ ID NO: 17)
DPhe-Arg-Trp-Asn, (SEQ ID NO: 18)
DPhe-Arg-Trp-Dap, (SEQ ID NO: 19)
DPhe-Arg-Trp,
```

```
                                    (SEQ ID NO: 20)
Pro-His-DPhe-Arg-Trp-Asn-Ala-Phe-DPro;

(SEQ ID NO: 21)
Pro-His-DPhe-Arg-Trp-Dap-Ala-Phe-DPro;

(SEQ ID NO: 22)
Pro-His-DPhe-Arg-Trp-Asn-Ala-DPro;

(SEQ ID NO: 23)
Pro-His-DPhe-Arg-Trp-Dap-Ala-DPro;

(SEQ ID NO: 24)
Pro-His-DPhe-Arg-Trp-Asn-DPro;

(SEQ ID NO: 25)
Pro-His-DPhe-Arg-Trp-Dap-DPro];
```

```
                                            (SEQ ID NO: 26)
Pro-His-DPhe-Arg-Trp-DPro;

(SEQ ID NO: 27)
Pro-DPhe-Arg-Trp-Asn-Ala-Phe-DPro;

(SEQ ID NO: 28)
Pro-DPhe-Arg-Trp-Dap-Ala-Phe-DPro;

(SEQ ID NO: 29)
Pro-DPhe-Arg-Trp-Asn-Ala-DPro;

(SEQ ID NO: 30)
Pro-DPhe-Arg-Trp-Dap-Ala-DPro;

(SEQ ID NO: 31)
Pro-DPhe-Arg-Trp-Asn-DPro;

(SEQ ID NO: 32)
Pro-DPhe-Arg-Trp-Dap-DPro;
or (SEQ ID NO: 33)
Pro-DPhe-Arg-Trp-DPro.
```

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

In one embodiment, the compound of invention is a cyclic peptide, comprising an amino acid sequence having at least 90% sequence identity to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

In one embodiment, the compound of invention is a cyclic peptide, comprising an amino acid sequence having at least 99% sequence identity to SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, or SEQ ID NO:33.

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:20. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:20.

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:23. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:23.

In one embodiment, the compound of invention is a cyclic peptide, comprising an amino acid sequence having at least 80% sequence identity to:

```
                                            (SEQ ID NO: 42)
Pro-His-DPhe-Arg-Trp-Asn-Lys-Phe-DPro;

(SEQ ID NO: 43)
Pro-His-DPhe-Arg-Trp-Asn-Lys(Ac-Arg)-Phe-DPro;

(SEQ ID NO: 44)
Pro-His-DPhe-Arg-Trp-Asn-Lys(Ac-Arg-Arg)-Phe-DPro;

(SEQ ID NO: 45)
Pro-His-DPhe-Arg-Trp-Asn-Lys(Ac-Arg-Arg-Arg)-Phe-
DPro;

(SEQ ID NO: 46)
Pro-His-DPhe-Arg-Trp-Dap-Lys-DPro;

(SEQ ID NO: 47)
Pro-His-DPhe-Arg-Trp-Dap-Lys(Ac-Arg)-DPro;

(SEQ ID NO: 48)
Pro-His-DPhe-Arg-Trp-Dap-Lys(Ac-Arg-Arg)-DPro;
or (SEQ ID NO: 49)
Pro-His-DPhe-Arg-Trp-Dap-Lys(Ac-Arg-Arg-Arg)-DPro.
```

In one embodiment, the compound of invention is a cyclic peptide, comprising an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:42, SEQ ID NO:43, SEQ ID NO:44, SEQ ID NO:45, SEQ ID NO:46, SEQ ID NO:47, SEQ ID NO:48 or SEQ ID NO:49. In one embodiment, the compound of invention is a cyclic peptide, consisting of an amino acid sequence having at least 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:42, SEQ ID NO:43, SEQ ID NO:44, SEQ ID NO:45, SEQ ID NO:46, SEQ ID NO:47, SEQ ID NO:48 or SEQ ID NO:49.

In one embodiment, the compound of invention is a cyclic peptide, comprising SEQ ID NO:15 or SEQ ID NO:16.

In certain embodiments, the cyclic peptide is between about 5 to about 13 amino acids in length. In certain embodiments, the cyclic peptide is about 5, 6, 7, 8, 9, 10, 11, 12 or 13 amino acids in length. In certain embodiments, $X^1$, $X^2$, $X^3$ and/or $X^4$ is a residue of a lysine or comprises a residue of a lysine and the side-chain amine of the lysine is optionally linked through an amide bond to the carboxy terminus of an amino acid or the carboxy terminus of a peptide that is 2, 3, or 4 amino acids in length. Thus, in certain embodiments, the cyclic peptide includes additional amino acids, which are linked through a lysine at the $X^1$, $X^2$, $X^3$ and/or $X^4$ position.

In one embodiment, the compound of invention is an agonist for MC1R, MC3R, MC4R or MC5R. As described herein, agonist activity is the ability of a compound of the invention to stimulate a melanocortin receptor. The activity may be measured using an assay described in the Examples and may be reported as an $EC_{50}$ value (i.e., the concentration of compound needed to achieve 50% stimulation).

In one embodiment, the compound of invention is an agonist for MC4R.

In one embodiment, the compound of invention is a selective agonist for MC1R, MC3R, MC4R or MC5R. For example, a compound of the invention may be at least 5, at least 10, at least 50, at least 100, at least 500, or at least 1,000 fold selective for a given melanocortin receptor (e.g., MC1R, MC3R, MC4R and/or MC5R) over another melanocortin receptor(s) in a selected assay (e.g., an assay described in the Examples herein). In one embodiment, the compound of invention is a selective agonist for MC4R. In one embodiment the compound may be at least 5, at least 10, at least 50, at least 100, at least 500, or at least 1,000 fold selective for MC4R over another melanocortin receptor(s).

One embodiment of the invention provides a composition (e.g., a pharmaceutical composition) comprising a compound of formula I, or a pharmaceutically acceptable salt thereof, and a pharmaceutically acceptable carrier.

One embodiment of the invention provides a dietary supplement comprising a compound of formula I, or a salt thereof.

Another embodiment of the invention provides a prodrug of a compound of formula I or a salt thereof. As used herein the term "prodrug" refers to a biologically inactive compound that can be metabolized in the body to produce a biologically active form of the compound.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

When a bond in a compound of formula I herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

In cases where compounds are sufficiently basic or acidic, a salt of a compound of formula (I) can be useful as an intermediate for isolating or purifying a compound of formula (I). Additionally, administration of a compound of formula (I) as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Certain Methods of the Invention

The invention also provides a method for treating obesity or a disease associated with obesity in an animal (e.g., a mammal, such as a human) comprising administering a compound of formula I or a pharmaceutically acceptable salt thereof to the animal.

The invention also provides a compound of formula I or a pharmaceutically acceptable salt thereof for the prophylactic or therapeutic treatment of obesity or a disease associated with obesity.

The invention also provides the use of a compound of formula I or a pharmaceutically acceptable salt thereof to prepare a medicament for treating obesity or a disease associated with obesity.

In one embodiment, the disease associated with obesity is diabetes, cardiovascular disease or hypertension.

The invention also provides a compound of formula I or a pharmaceutically acceptable salt thereof for use in medical therapy.

One embodiment of the invention provides a method of modulating (e.g., increasing or decreasing) the activity of a melanocortin receptor in vitro or in vivo comprising contacting the receptor with an effective amount of a compound of formula I, or a pharmaceutically acceptable salt thereof. In certain embodiments, such a method comprises contacting a cell comprising the melanocortin receptor. In certain embodiments, the cell is in a mammal. In certain embodiments, the cell is contacted by administering the compound of formula (I) or a salt thereof (e.g., a pharmaceutically acceptable salt thereof) to the mammal. In certain embodiments, the compound of formula (I) or a salt thereof, increases the activity of the melanocortin receptor (e.g., as compared to a control). In certain embodiments, the compound of formula (I) or a salt thereof, decreases the activity of the melanocortin receptor (e.g., as compared to a control).

One embodiment of the invention provides a compound of formula I, or a pharmaceutically acceptable salt thereof for use in modulating (e.g., increasing or decreasing) the activity of a melanocortin receptor in vitro or in vivo.

One embodiment of the invention provides the use of a compound of formula I, or a pharmaceutically acceptable salt thereof for the manufacture of a medicament for modulating (e.g., increasing or decreasing) the activity of a melanocortin receptor in vitro or in vivo.

In one embodiment, the melanocortin receptor is MC1R, MC3R, MC4R or MC5R.

In one embodiment, the melanocortin receptor is MC4R.

Another embodiment of the invention provides a method of modulating (e.g., increasing or decreasing) metabolic activity in an animal in need thereof, comprising administering an effective amount of a compound of formula I, or a pharmaceutically acceptable salt thereof, to the animal.

Another embodiment of the invention provides a compound of formula I, or a pharmaceutically acceptable salt thereof for use in modulating (e.g., increasing or decreasing) metabolic activity.

Another embodiment of the invention provides the use of a compound of formula I, or a pharmaceutically acceptable salt thereof for the manufacture of a medicament for modulating (e.g., increasing or decreasing) metabolic activity in an animal in need thereof.

Another embodiment of the invention provides a method of modulating (e.g., increasing or decreasing) appetite in an animal in need thereof, comprising administering an effective amount of a compound of formula I, or a pharmaceutically acceptable salt thereof, to the animal.

Another embodiment of the invention provides a compound of formula I, or a pharmaceutically acceptable salt thereof for use in modulating (e.g., increasing or decreasing) appetite.

Another embodiment of the invention provides the use of a compound of formula I, or a pharmaceutically acceptable salt thereof for the manufacture of a medicament for modulating (e.g., increasing or decreasing) appetite in an animal in need thereof.

The ability of a compound of formula (I) to, e.g., modulate appetite, modulate metabolic activity or to treat obesity or diseases associated with obesity (e.g., diabetes, cardiovascular disease or hypertension) may be tested using an assay known in the art or described in the Examples.

In certain embodiments, the animal is a mammal. In certain embodiments, the mammal is a human.

Administration

Compounds of formula (I) (including salts and prodrugs thereof) can be formulated as pharmaceutical compositions and administered to a mammalian host, such as a human patient in a variety of forms adapted to the chosen route of administration, i.e., orally or parenterally, by intravenous, intramuscular, intrathecal, topical, nasal, inhalation, suppository, sub dermal osmotic pump, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously, intrathecally or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents. For example, compounds of formula (I), or salts thereof, may be administered with other agents that are useful for modulating appetite (i.e., increasing or decreasing), modulating metabolic activity, treating obesity or diseases associated with obesity (e.g., diabetes, cardiovascular disease or hypertension), inducing weight loss, increasing or decreasing weight gain. Accordingly, in one embodiment the invention also provides a composition comprising a compound of formula (I), or a pharmaceutically acceptable salt thereof, at least one other therapeutic agent, and a pharmaceutically acceptable diluent or carrier. The invention also provides a kit comprising compound of formula (I), or a pharmaceutically acceptable salt thereof, at least one other therapeutic agent, packaging material, and instructions for administering the compound of formula (I) or the pharmaceutically acceptable salt thereof and the other therapeutic agent or agents to an animal to modulate appetite, modulate metabolic activity, treat obesity or diseases associated with obesity (e.g., diabetes, cardiovascular disease or hypertension), induce weight loss, increase weight gain, or decrease weight gain.

Certain Definitions

The term "alkyl", by itself or as part of another substituent, means, unless otherwise stated, a straight or branched chain hydrocarbon radical, having the number of carbon atoms designated (i.e., $C_{1-4}$ means one to four carbons). Non limiting examples of "alkyl" include methyl, ethyl, propyl, isopropyl, butyl, iso-butyl, sec-butyl.

The term "halo" means fluoro, chloro, bromo, or iodo.

The term "haloalkyl" means an alkyl that is optionally substituted with one or more (e.g., 1, 2, 3, 4, or 5) halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. Dap, PyrAla, ThiAla, (pCl)Phe, (pNO$_2$)Phe, ε-Aminocaproic acid, Met[O2], dehydPro, (3I)Tyr, norleucine (Nle), para-I-phenylalanine ((pI)Phe), 2-napthylalanine (2-Nal), β-cyclohexylalanine (Cha), β-alanine (β-Ala), phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid (Tic), penicillamine, ornithine, citruline, α-methyl-alanine, para-benzoylphenylalanine, phenylglycine, propargylglycine, sarcosine, and tert-butylglycine) in D or L form. The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "peptide" describes a sequence of 2 to 25 amino acids (e.g. as defined hereinabove) or peptidyl residues. The sequence may be linear or cyclic. For example, a cyclic peptide can be prepared or may result from the formation of amide bonds or disulfide bridges between two cysteine residues in a sequence. When a peptide is cyclic, it can be illustrated as "c[peptide sequence]". A peptide can be linked to the remainder of a compound of formula I through the carboxy terminus, the amino terminus, or through any other convenient point of attachment, such as, for example, through the sulfur of a cysteine. In certain embodiments, a peptide comprises 3 to 10, or 4 to 8 amino acids. In certain embodiments, a peptide comprises 5 to 13 amino acids, or 5 to 9 amino acids. In certain embodiments, a compound of formula I comprises between about 5 to about 29 amino acid residues. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right. The term "dipeptide" refers to a peptide comprising two amino acids joined through an amide bond. The term "tripeptide" means a peptide comprising three amino acids joined through two amide bonds. The terms "protein," "peptide" and "polypeptide" are used interchangeably herein.

As used herein, the term "residue of an amino acid, dipeptide or tripeptide" means a portion of an amino acid, dipeptide or tripeptide. For example, variables $X^1$, $X^2$, $X^3$ and $X^4$ may be residues of an amino acid, dipeptide or tripeptide, wherein certain atoms (e.g., H or OH) have been removed to link the amino acids via a peptide bond.

The following terms are used to describe the sequence relationships between two or more sequences (e.g., polypeptides): (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length peptide sequence or the complete peptide sequence.

(b) As used herein, "comparison window" makes reference to a contiguous and specified segment of a sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) CABIOS, 4:11; the local homology algorithm of Smith et al. (1981) Adv. Appl. Math. 2:482; the homology alignment algorithm of Needleman and Wunsch, (1970) JMB, 48:443; the search-for-similarity-method of Pearson and Lipman, (1988) Proc. Natl. Acad. Sci. USA, 85:2444; the algorithm of Karlin and Altschul, (1990) Proc. Natl. Acad. Sci. USA, 87:2264, modified as in Karlin and Altschul, (1993) Proc. Natl. Acad. Sci. USA, 90:5873.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237; Higgins et al. (1989) CABIOS 5:151; Corpet et al. (1988) Nucl. Acids Res. 16:10881; Huang et al. (1992) CABIOS 8:155; and Pearson et al. (1994) Meth. Mol. Biol. 24:307. The ALIGN program is based on the algorithm of Myers and Miller, supra. The BLAST programs of Altschul et al. (1990) JMB, 215:403; Nucl. Acids Res., 25:3389 (1990), are based on the algorithm of Karlin and Altschul supra.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The terms "treat" and "treatment" refer to both therapeutic treatment and prophylactic or preventative measures, wherein the object is to prevent or decrease an undesired physiological change or disorder, such as a metabolic disorder (e.g., obesity) or a disease associated with the metabolic disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to, e.g., humans, higher non-human primates, rodents, domestic, cows, horses, pigs, sheep, dogs and cats. In one embodiment, the mammal is a human.

The invention will now be illustrated by the following non-limiting Examples.

Example 1

Design of Melanocortin Receptor Modulators

It has previously been demonstrated that the endogenous melanocortin antagonist AGRP may be converted into an agonist by select modifications. The full-length AGRP is 132 amino acids, though the highly structured C-terminal domain has been shown to be equipotent to the full-length protein (Ollmann, M. M., et al. *Science* 1997, 278, 135-138; and Yang, Y. K., et al. *Mol. Endocrinol.* 1999, 13, 148-155). An Arg-Phe-Phe tripeptide sequence critical for activity is located on an exposed β-hairpin loop within the 46-residue C-terminal domain (Bolin, K. A., et al. *FEBS Lett.* 1999, 451, 125-131; McNulty, J. C., et al. *Biochemistry* 2001, 40, 15520-15527; and Tota, M. R., et al. *Biochemistry* 1999, 38, 897-904). Further truncation of the C-terminal 12 amino acids and a Cys to Ala substitution has been shown to retain the β-hairpin loop with minimal loss in antagonist potency, resulting in "mini-AGRP" (Jackson, P. J., et al. *Biochemistry* 2002, 41, 7565-7572). Substitution of the potent melanocortin agonist His-DPhe-Arg-Trp tetrapeptide sequence into the Arg-Phe-Phe residues of mini-AGRP resulted in the formation of a potent, nonselective melanocortin agonist, possessing nanomolar agonist potency at the MC4R (Jackson, P. J., et al. *Peptides* 2005, 26, 1978-1987; and Wilczynski, A., et al. *J. Med. Chem.* 2004, 47, 2194-2207). The length, structural complexity, and relatively high synthetic cost of this chimeric peptide hindered additional structure-activity relationship (SAR) studies. While further truncations beyond mini-AGRP traditionally result in diminished antagonist potencies, substitution of the His-DPhe-Arg-Trp tetrapeptide into the Tyr-flanked, lactam-cyclized β-hairpin active loop of AGRP (Tyr-c[Asp-His-DPhe-Arg-Trp-Asn-Ala-Phe-Dap]-Tyr-NH$_2$) resulted in a nonselective sub-nanomolar potent agonist at the MC1R, MC3R, MC4R, and MC5R (Wilczynski, A., et al. *J. Med. Chem.* 2004, 47, 2194-2207; and Wilczynski, A., et al. *J. Med. Chem.* 2005, 48, 3060-3075). Similar nanomolar to sub-nanomolar potencies were observed when a Tyr-flanked disulfide bridge was used to cyclize the active loop of AGRP (Tyr-c[Cys-His-DPhe-Arg-Trp-Asn-Ala-Phe-Cys]-Tyr-NH$_2$) (Singh, A., et al. *J. Med. Chem.* 2011, 54, 1379-1390). Substitution of the Arg-Phe-Phe tripeptide into the DPhe-Arg-Trp sequence of NDP-MSH resulted in sub-micromolar agonist potencies, while the same replacement in MTII only resulted in partial receptor stimulation at the MC1R at concentrations up to 100 µM (Joseph, C. G., et al. *Peptides* 2003, 24, 1899-1908).

While truncation of AGRP classically results in diminished antagonist potency, one report demonstrated that the peptide c[Pro-Arg-Phe-Phe-Asn-Ala-Phe-DPro], the active loop of AGRP cyclized through a DPro-Pro motif, was only 50-fold less potent than AGRP(87-132) at the mMC4R despite the removal of 38 amino acids (Ericson, M. D., et al. *J. Med. Chem.* 2015, 58, 4638-4647). Further SAR studies demonstrated that replacement of the Asn with a Dap residue resulted in a cyclic octapeptide that was as potent an antagonist as AGRP at the MC4R, 160-fold selective for the MC4R over the MC3R, possessed minimal activity at the MC1R, and was unable to stimulate the MC5R at up to 100 µM concentrations (Ericson, M. D., et al. *J. Med. Chem.* 2015, 58, 4638-4647). Due to the prior reported activity of AGRP chimeric peptides, and the potency and selectivity of the Dap-containing octapeptide, it was hypothesized that incorporating the melanocortin agonist His-DPhe-Arg-Trp sequence into the octapeptide scaffold may result in a potent and MC4R-selective agonist. Furthermore, since this molecular scaffold is based upon the active loop of AGRP, it may be postulated that the resulting ligands may bypass the negative side effects of previously reported MC4R-selective compounds. In attempts to generate new potent, selective melanocortin agonists, a series of 14 cyclic peptides was synthesized and characterized at the mouse melanocortin receptors. The His-DPhe-Arg-Trp tetrapeptide and DPhe-Arg-Trp tripeptide sequences were substituted for the Arg-Phe-Phe tripeptide in the DPro-Pro cyclized antagonist scaffold. Peptides containing either the native Asn residue or the more potent MC4R Dap substitution were examined for differences in potency and/or selectivity. Additionally, truncations of the non-pharmacophore Phe, Ala, and Asn/Dap amino acids were examined to explore the optimal size of the cyclic agonists and the importance of these residues.

Example 2

Peptide Synthesis of Characterization

All peptides were synthesized using standard Fmoc chemistry (Carpino, L. A., et al. *J. Am. Chem. Soc.* 1970, 92, 5748-5749). Amino acids Fmoc-DPro, Fmoc-Phe, Fmoc-Ala, Fmoc-Asn(Trt), Fmoc-Trp(Boc), Fmoc-Arg(Pbf), Fmoc-DPhe, and Fmoc-His(Trt), H-Pro-2-chlorotrityl resin, and coupling reagents 2-(1-H-benzotriazol-1-yl)-1,1,3,3-tetramethyluronium hexafluorophosphate (HBTU), 1-hydroxybenzotriazole (HOBt), and benzotriazol-1-yl-oxy-tris(dimethylamino) phosphonium hexafluorophosphate (BOP) were purchased from Peptides International (Louisville, Ky.). Fmoc-Dap(Boc) was purchased from Peptides International and Bachem (Torrance, Calif.). Dichloromethane (DCM), methanol (MeOH), acetonitrile (ACN), dimethylformamide (DMF), triflouroethanol (TFE), acetic acid, and anhydrous ethyl ether were purchased from Fisher (Fair Lawn, N.J.). Trifluoroacetic acid (TFA), dimethyl sulfoxide (DMSO), piperidine, triisopropylsilane (TIS), and N,N-diisopropylethylamine (DIEA) were purchased from Sigma-Aldrich (St. Louis, Mo.). All reagents and chemicals were ACS grade or better and were used without further purification.

Peptides were synthesized on a 0.10 mmol scale using a H-Pro-2-Chlorotrityl resin (0.76 meq/g) with a manual microwave synthesizer (CEM Discover SPS). Syntheses consisted of two repeated steps: (i) removal of the Fmoc group with 20% piperidine (1x at rt for 2 min, 1× using microwave irradiation for 4 min at 75° C. with 30 W), and (ii) single coupling of the incoming Fmoc-protected amino acid (3 eq) with HBTU (3 eq) and DIPEA (5 eq) in DMF using microwave irradiation (75° C., 5 min, 30 W). A lower temperature was utilized for His (50° C.) to avoid epimerization. The Arg coupling utilized more Arg (5 eq), HBTU (5 eq), and DIPEA (7 eq), and a longer irradiation time (10 min). After completion of the syntheses, peptides were cleaved with either a 99:1 DCM:TFA solution or 1:1:8 acetic acid:TFE:DCM solution. The cleavage solutions were then concentrated and side-chain protected peptides were precipitated using ice-cold ethyl ether. Peptides were cyclized in DCM with BOP (3 eq) and HOBt (3 eq) overnight, and the DCM was removed under vacuum. Without further purification, the cyclized peptides were side-chain deprotected using a 95:2.5:2.5 TFA:TIS:H$_2$O solution for 2 hrs, the solution was then concentrated, and peptides precipitated using ice-cold ethyl ether.

Crude peptides were purified by reverse-phase HPLC using a Shimadzu system with a photodiode array detector and a semi-preparative RP-HPLC C18 bonded silica column (Vydac 218TP1010, 1.0×2.5 cm). The peptides were at least 95% pure as assessed by analytical RP-HPLC in two diverse solvent systems and had the correct molecular weight by MALDI-MS (University of Minnesota Mass Spectrometry Lab) (Table 1).

Peptides were synthesized on a chlorotrityl resin to permit cleavage from the resin while retaining the side-chain protecting groups, necessary for the cyclization of the peptides without any terminal to side-chain cyclized byproducts. The syntheses were aided by microwave irradiation, which has previously been shown to prematurely cleave peptides from chlorotrityl resins (Echalier, C., et al. *Amino Acids* 2013, 45, 1395-1403). This was postulated to be due to direct thermal hydrolysis of the peptide from resin and was dependent on the amount of time the resin-bound peptide was exposed to elevated temperatures (Echalier, C., et al. *Amino Acids* 2013, 45, 1395-1403). The reported crude yields of 47.5-71.3% were similar to previous syntheses from the same H-Pro-chlorotrityl resin at room temperature (51.6-98.6%). It may be speculated that the relatively consistent yields may be a result of minimal time the peptide-resin was exposed to elevated temperatures (<10 min per coupling cycle) or the first amino acid (Pro) afforded some protection from premature cleavage.

Example 3

Biological Evaluation (1) cAMP AlphaScreen® Bioassay

Peptide ligands were dissolved in DMSO at a stock concentration of 10$^{-1}$ M and were pharmacological characterized using HEK293 cells stably expressing the mouse MC1R, MC3-5R by the cAMP AlphaScreen® assay (PerkinElmer) according to the manufacturer's instructions and as previously described (Ericson, M. D., et al. *Bioorg. Med. Chem. Lett.* 2015, 25, 5306-5308; Singh, A., et al. *ACS Med. Chem. Lett.* 2015, 6, 568-572; and Tala, S. R., et al. *Bioorg. Med. Chem. Lett.* 2015, 25, 5708-5711).

Briefly, cells 70-90% confluent were dislodged with Versene (Gibco®) at 37° C. and plated 10,000 cells/well in a 384-well plate (Optiplate™) with 10 μL freshly prepared stimulation buffer (1× HBSS, 5 mM HEPES, 0.5 mM IBMX, 0.1% BSA, pH=7.4) with 0.5 μg anti-cAMP acceptor beads per well. The cells were stimulated with the addition of 5 μL stimulation buffer containing peptide (a seven point dose-response curve was used starting at $10^{-4}$ to $10^{-7}$ M, determined by ligand potency) or forskolin ($10^{-4}$ M) and incubated in the dark at room temperature for 2 hr.

Following stimulation, streptavidin donor beads (0.5 μg) and biotinylated-cAMP (0.62 μmol) were added to the wells in a subdued light environment with 10 μL lysis buffer (5 mM HEPES, 0.3% Tween-20, 0.1% BSA, pH=7.4) and the plates were incubated in the dark at room temperature for an additional 2 hr. Plates were read on a Enspire (PerkinElmer) Alpha-plate reader using a pre-normalized assay protocol (set by the manufacturer).

(2) Data Analysis

The $EC_{50}$ values represent the mean of duplicate replicates performed in at least three independent experiments. The $EC_{50}$ estimates and associated standard errors (SEM) were determined by fitting the data to a nonlinear least-squares analysis using the PRISM program (v4.0, GraphPad Inc.). The ligands were assayed as TFA salts and not corrected for peptide context.

(3) Results

The compounds were assayed for agonist activity using the AlphaScreen® cAMP assay using HEK293 cells stably transfected with the mouse melanocortin 1, 3, 4, and 5 receptors according to the manufacturer's instructions and as previously reported (Ericson, M. D., et al. *Bioorg. Med. Chem. Lett.* 2015, 25, 5306-5308; Singh, A., et al. *ACS Med. Chem. Lett.* 2015, 6, 568-572; and Tala, S. R., et al. *Bioorg. Med. Chem. Lett.* 2015, 25, 5708-5711). The MC2R is only stimulated by ACTH and was therefore excluded from this study. The potent, nonselective melanocortin ligand NDP-MSH was used as a positive control (Sawyer, T. K., et al. *Proc. Natl. Acad. Sci. U.S.A.* 1980, 77, 5754-5758). Since the AlphaScreen® cAMP assay is a competition assay resulting in a lower signal at higher concentrations of ligand, concentration-activity curves were normalized to baseline and maximal NDP-MSH signal for illustrative purposes as previously described (Ericson, M. D., et al. *Bioorg. Med. Chem. Lett.* 2015, 25, 5306-5308; and Elster, L., et al. *J. Biomol. Screen.* 2007, 12, 41-49). Due to the inherent error of the assay, compounds that were within a three-fold potency range were considered equipotent. Compounds that resulted in greater than 80% maximal NDP-MSH stimulation were considered to possess full agonist efficacy.

Table 2 summarizes the functional agonist pharmacology of the synthesized ligands. Substitution of the agonist His-DPhe-Arg-Trp sequence in the native antagonist loop in place of Arg-Phe-Phe resulted in compound MDES-149-2c, possessing 0.35, 32, 1.4, and 0.45 nM agonist potencies at the mMC1R, mMC3R, mMC4R, and mMC5R, respectively (Table 2, FIG. 1). Truncation of the Phe residue resulted in compound MDE6-3-2c and decreased agonist potency relative to MDE5-149-2c, with potency losses of 34-, 9-, 21-, and 5-fold at the mMC1R, mMC3R, mMC4R, and mMC5R. Removal of the Asn amino acid (MDE6-10-2c) further decreased agonist potency 143-, 121-, and 37-fold at the mMC1R, mMC4R and mMC5R, relative to MDE5-149-2c. Compound MDE6-10-2c was a partial agonist at the mMC3R and possessed 65% the maximal efficacy of NDP-MSH with an $EC_{50}$ value of 510 nM.

Previously, it was shown that substitution of the Asn with a Dap residue could increase the antagonist potency of the resulting AGRP-derived octapeptide and resulted in a greater than 160-fold selectivity for the mMC4R over the mMC3R (Ericson, M. D., et al. *J. Med. Chem.* 2015, 58, 4638-4647). It was hypothesized that the same substitution with the agonist tetrapeptide His-DPhe-Arg-Trp sequence may create a potent and selective mMC4R agonist. This substitution was incorporated into peptide MDE5-151-2c, which possessed 24, 260, and 18 nM agonist potency at the mMC1R, mMC3R, and mMC5R. Compound MDE5-151-2c was a partial agonist at the mMC4R, possessed 70% of the maximal NDP-MSH response and 23 nM $EC_{50}$ value at this receptor. In contrast to the Asn-containing MDE5-149-2c, removal of the Phe residue increased agonist potency (Table 2, FIGS. 1A-1D). Compound MDE6-5-2c was able to full stimulate the mMC4R ($EC_{50}$=1.6 nM), and possessed 1.1, 40, and 0.3 nM agonist potency at the mMC1R, mMC3R, and mMC5R. At all receptors assayed, MDE6-5-2c was equipotent to MDES-149-2c (Table 2, FIGS. 1A-1D). Further truncation of the Ala residue (MDE6-12-2c) decreased agonist potency 418-, 593-, and 1,100-fold at the mMC1R, mMC4R, and mMC5R relative to MDE6-5-2c, and was able to stimulate the mMC3R to 65% of the maximal NDP-MSH response at concentrations up to 100 μM. Removal of the Asn/Dap position, resulting in the His-DPhe-Arg-Trp tetrapeptide sequence cyclized through a DPro-Pro motif in hexapeptide MDES-147-2c, was able to partially stimulate the mMC3R and mMC4R relative to NDP-MSH (60% and 65% at 100 μM). This peptide also possessed 900 and 6,000 nM agonist $EC_{50}$ values at the mMC1R and mMC5R, respectively.

It has previously been shown that the tripeptide Ac-DPhe-Arg-Trp-NH$_2$ possesses micromolar agonist potency at the mMC1R, mMC4R, and mMC5R (Haskell-Luevano, C., et al. *J. Med. Chem.* 2001, 44, 2247-2252), and was the minimal fragment of NDP-MSH to possess agonist activity using the classic frog skin bioassay (Haskell-Luevano, C., et al. *Peptides* 1996, 17, 995-1002). In the native loop sequence of AGRP, an Arg-Phe-Phe tripeptide is postulated to be the active pharmacophore. It was hypothesized that insertion of the DPhe-Arg-Trp tripeptide into the DPro-Pro cyclized loop mimetics of AGRP may result in increased potency and/or selectivity in the resulting chimeric peptides, since this agonist sequence is the same length as the postulated antagonist active sequence and would not alter peptide length. Insertion of the DPhe-Arg-Trp tripeptide into the native, Asn-containing, loop sequence cyclized through DPro-Pro residues resulted in peptide MDE5-149-1c, which was unable to fully stimulate the mMC3R (45% of maximal NDP-MSH at 100 μM concentrations). This peptide was a weaker agonist relative to MDE5-149-2c, and possessed 400, 130, and 40 nM agonist potency at the mMC1R, mMC4R, and mMC5R, respectively (1140-, 90-, and 90-fold decreased potency relative to MDE5-149-2c). Similar potency was observed at all the melanocortin receptors when the Phe amino acid was removed, generating MDE6-3-1c. The removal of the Ala residue (MDE6-10-1c) resulted in increased agonist potency at the mMC1R (40 nM, 10-fold increase over MDE5-149-1c), and modest decreased signal at the mMC4R (1,100 nM, 8-fold decrease). Peptide MDE6-10-1c partially stimulated the mMC5R (25% of NDP-MSH) and showed no agonist activity at the mMC3R at concentrations up to 100 µM.

A similar trend of decreased agonist potency was observed when the DPhe-Arg-Trp was inserted into an AGRP active loop sequence where Asn was substituted with Dap (MDE5-151-1c). This compound was a partial agonist at the mMC1R and mMC3R (45% and 70% NDP-MSH maximum signal with $EC_{50}$ values of 190 and 3,000 nM, respectively), and possessed 100 nM and 46 nM potency with full agonist efficacy at the mMC4R and mMC5R (FIGS. 1A-1D). Truncation of the Phe residue to generate MDE6-5-1c resulted in similar potency at the mMC4R (150 nM) and mMC5R (48 nM), full agonist efficacy at the mMC1R (600 nM), and partially stimulated the mMC3R (70% at 100 µM concentrations). Further removal of the Ala residue to generate the hexapeptide MDE6-12-1c decreased agonist potency at all receptors assayed, with no observable activity at the mMC3R or mMC5R at 100 µM concentrations (FIG. 1), 35% partial stimulation of the mMC4R (relative to NDP-MSH), and possessed partial agonist efficacy at the mMC1R (75% NDP-MSH, $EC_{50}$=110 nM). Peptide MDE5-147-1c, the result of cyclizing the agonist tripeptide DPhe-Arg-Trp with a DPro-Pro motif, possessed the lowest potency at the mMC1R (1,800 nM), no activity at the mMC3R or mMC5R with concentrations up to 100 µM, and stimulated the mMC4R to 50% of the maximal level of NDP-MSH at 100 µM.

(4) Discussion

Melanocortin 1 Receptor Pharmacology

Prior chimeric ligands derived from the active loop of AGRP and the His-DPhe-Arg-Trp melanocortin agonist sequence result in sub-nanomolar agonist potency at the mMC1R, a receptor postulated to be involved in pigmentation (Chhajlani, V., et al. *FEBS Lett.* 1992, 309, 417-420; and Mountjoy, K. G., et al. *Science* 1992, 257, 1248-1251). The disulfide bridged Tyr-c[Cys-His-DPhe-Arg-Trp-Asn-Ala-Phe-Cys]-Tyr-NH2 was reported to possess 0.35 nM agonist potency at the mMC1R (Singh, A., et al. *J. Med. Chem.* 2011, 54, 1379-1390). Replacing the disulfide bridge with a lactam bridge, Tyr-c[Asp-His-DPhe-Arg-Trp-Asn-Ala-Phe-Dap]-Tyr-NH$_2$, resulted in a peptide ligand with 0.2 nM agonist potency (Wilczynski, A., et al. *J. Med. Chem.* 2004, 47, 2194-2207; and Wilczynski, A., et al. *J. Med. Chem.* 2005, 48, 3060-3075). Insertion of the His-DPhe-Arg-Trp-Gly-Lys hexapeptide of the potent synthetic melanocortin agonist NDP-MSH into the active loop of the truncated mini-AGRP template resulted in cAMP stimulation when administered at 1 µM concentrations to cells expressing the hMC1R; similar cAMP accumulation was observed when His-Phe-Arg-Trp (SEQ ID NO: 50) was inserted in the same template (Jackson, P. J., et al. *Peptides* 2005, 26, 1978-1987). A dose-response evalutation of this His-DPhe-Arg-Trp tetrapeptide inserted into the Arg-Phe-Phe sequence of mini-AGRP [Ac-mini-(His-DPhe-Arg-Trp)hAGRP-NH$_2$] demonstrated this peptide to possess 0.16 nM agonist potency at the mMC1R (Wilczynski, A., et al. *J. Med. Chem.* 2004, 47, 2194-2207). Both compounds MDES-149-2c and MDE6-5-2c from the present study possessed similar nanomolar or less potency at the mMC1R, with $EC_{50}$ values of 0.35 nM and 1.1 nM, respectively. It may be speculated that the MC1R agonist potency of MDES-149-2c and Ac-mini-(His-DPhe-Arg-Trp)hAGRP-NH2 may be due to a similar presentation of the His-DPhe-Arg-Trp on a loop structure. Conversion of MDES-149-2c to MDE6-5-2c, which possesses similar potency, included removal of a Phe residue and Asn to Dap substitution. Either modification alone did not improve potency: truncation of the Phe (MDE6-3-2c) decreased agonist potency 34-fold relative to MDES-149-2c; 70-fold decreased potency was observed for the Asn to Dap substitution (MDES-151-2c). Unexpectedly, compounds MDE5-151-1c and MDE6-12-1c were observed to be partial agonists at the mMC1R (FIGS. 1A-1D), stimulating the mMC1R 45% and 75% of the maximal NDP-MSH response, with EC50 values of 190 and 110 nM, respectively. Both peptides possessed an Asp to Dap substitution and lacked a His residue in the agonist sequence, though peptide MDE6-5-1c possessed these same modifications and was a full agonist at the mMC1R.

Melanocortin 3 Receptor Pharmacology

The melanocortin 3 receptor has been reported to be expressed in many different tissues; expression in the central nervous system has been linked to pathways involving energy homeostasis and food intake (Butler, A. A., et al. *Endocrinol.* 2000, 141, 3518-3521; and Irani, B. G., et al. *Eur. J. Pharmacol.* 2011, 660, 80-87). Previously reported AGRP/NDP-MSH chimeric ligands Tyr-c[Cys-His-DPhe-Arg-Trp-Asn-Ala-Phe-Cys]-Tyr-NH$_2$, Tyr-c[Asp-His-DPhe-Arg-Trp-Asn-Ala-Phe-Dap]-Tyr-NH$_2$, and Ac-mini-(His-DPhe-Arg-Trp)hAGRP-NH$_2$ have been reported to possess 2.0 nM, 1.0 nM, and 30 nM potencies, respectively, at the mMC3R (Wilczynski, A., et al. *J. Med. Chem.* 2004, 47, 2194-2207; Wilczynski, A., et al. *J. Med. Chem.* 2005, 48, 3060-3075; and Singh, A., et al. *J. Med. Chem.* 2011, 54, 1379-1390). The most potent compounds from the present study, MDES-149-2c and MDE6-5-2c, possessed agonist potencies of 32 and 40 nM respectively, most similar to the reported value for Ac-mini-(His-DPhe-Arg-Trp)hAGRP-NH$_2$. An additional two compounds were full agonists at the mMC3R (MDE6-3-2c and MDE5-151-2c; $EC_{50}$=300 and 260 nM). Three compounds did not possess agonist activity at the mMC3R (MDE6-10-1c, MDE6-12-1c, and MDE5-147-1c) and five ligands partially stimulated the mMC3R at concentrations up to 100 µM (MDE6-12-2c, MDE5-147-2c, MDE5-149-1c, MDE6-3-1c, and MDE6-5-1c). Two peptides displayed partial agonist efficacy (MDE6-10-2c and MDE5-151-1c), stimulating cAMP to 65% and 70% of maximal NDP-MSH response and $EC_{50}$ values of 510 and 3000 nM, respectively. The decreased potencies and activities at the mMC3R may indicate that this scaffold is not well situated for this receptor, perhaps due to intrinsic lower potency of AGRP at the mMC3R versus the mMC4R (~10-fold) or by the addition of the Dap amino acid which previously was shown to impart some selectivity for the mMC4R over the mMC3R when the antagonist Arg-Phe-Phe tripeptide sequence was examined in this scaffold (Ericson, M. D., et al. *J. Med. Chem.* 2015, 58, 4638-4647).

Melanocortin 4 Receptor Pharmacology

The MC4R is expressed in numerous tissues; mice lacking this receptor possess an obese phenotype that is also observed in many mutations of the human form of the MC4R (Huszar, D., et al. *Cell* 1997, 88, 131-141; and Farooqi, I. S., et al. *N. Engl. J. Med.* 2003, 348, 1085-1095). Chimeric AGRP/NDP-MSH ligands Tyr-c[Cys-His-DPhe-Arg-Trp-Asn-Ala-Phe-Cys]-Tyr-NH$_2$, Tyr-c[Asp-His-DPhe-Arg-Trp-Asn-Ala-Phe-Dap]-Tyr-NH$_2$, and Ac-mini- (His-DPhe-Arg-Trp)hAGRP-NH$_2$ have been reported to possess 0.3 nM, 0.2 nM, and 1.4 nM potencies at the mMC4R (Wilczynski, A., et al. *J. Med. Chem.* 2004, 47, 2194-2207; Wilczynski, A., et al. *J. Med. Chem.* 2005, 48, 3060-3075; Singh, A., et al. *J. Med. Chem.* 2011, 54, 1379-1390; and Xiang, Z. M., et al. *Biochemistry* 2007, 46, 8273-8287). Two ligands (MDE5-149-2c and MDE6-5-2c) possessed similar 1.4 nM and 1.6 nM potencies, respectively. Unlike the mMC3R, all ligands were able to stimulate the mMC4R, though three compounds (MDE5-147-2c, MDE6-12-1c, and MDE5-147-1c) stimulated a fraction of the maximal NDP-MSH response at 100 μM concentrations and peptide MDE5-151-2c was a partial agonist (70% maximal NDP-MSH stimulation, EC$_{50}$=23).

Melanocortin 5 Receptor Pharmacology

The MC5R is expressed ubiquitously in the periphery and has been hypothesized to be involved in exocrine gland function (Chen, W. B., et al. *Cell* 1997, 91, 789-798). The previously reported ligands Tyr-c[Cys-His-DPhe-Arg-Trp-Asn-Ala-Phe-Cys]-Tyr-NH$_2$, Tyr-c[Asp-His-DPhe-Arg-Trp-Asn-Ala-Phe-Dap]-Tyr-NH$_2$, and Ac-mini-(His-DPhe-Arg-Trp)hAGRP-NH$_2$ possessed agonist potencies of 2 nM, 0.5 nM, and 0.6 nM at the mMC5R (Wilczynski, A., et al. *J. Med. Chem.* 2004, 47, 2194-2207; Wilczynski, A., et al. *J. Med. Chem.* 2005, 48, 3060-3075; and Singh, A., et al. *J. Med. Chem.* 2011, 54, 1379-1390). The two most potent compounds, MDE5-149-2c and MDE6-5-2c possessed similar 0.45 nM and 0.3 nM agonist potencies at the mMC5R. One peptide (MDE6-12-1c) was unable to stimulate the mMC5R at concentrations up to 100 μM, while two ligands (MDE6-10-1c and MDE5-147-1c) partially stimulated the receptor at 100 μM concentrations. The remainder of the synthesized ligands possessed nanomolar to micromolar agonist potencies at this receptor.

Unlike the antagonist pharmacology previously reported which showed a beneficial antagonist potency and selectivity increase with a Dap residue (Ericson, M. D., et al. *J. Med. Chem.* 2015, 58, 4638-4647), there is not a clear trend for the Asn or Dap residue following the Trp amino acid for increased agonist potency or selectivity. Of the two most potent ligands that had similar activities at the MCRs, one possessed an Asn amino acid (MDES-149-2c) and one a Dap residue (MDE6-5-2). These peptides were also different lengths, with a heptapeptide sequence cyclized through a DPro-Pro motif in MDES-149-2c (His-DPhe-Arg-Trp-Asn-Ala-Phe) and a hexapeptide in MDE6-5-2c (His-DPhe-Arg-Trp-Dap-Ala). The sequential removal of the Phe and then Ala from MDES-149-2c resulted in decreased potencies at the receptor subtypes, indicating the heptapeptide sequence may be ideal for this sequence. Comparatively, the addition of the Phe residue or subtraction of the Ala from MDE6-5-2c both decreased potency. It appears as if both the Asn and the Dap substitutions are tolerable for an agonist ligand, and the size of the resulting cyclic peptides influences potency. Interestingly, MDES-149-2c possess the same purported active loop sequence as Ac-mini-(His-DPhe-Arg-Trp) hAGRP-NH$_2$ and possesses nearly identical pharmacology at all four receptors (0.35, 32, 1.4, and 0.45 nM for MDES-149-2c at the mMC1R, mMC3R, mMC4R, and mMC5R versus 0.16, 30, 1.4, and 0.56 nM for Ac-mini-(His-DPhe-Arg-Trp)hAGRP-NH$_2$) (Wilczynski, A., et al. *J. Med. Chem.* 2004, 47, 2194-2207), though these were measured using different cAMP assays and direct comparisons may not be valid. Overall, MDES-149-2c is 26 residues shorter compared to Ac-mini-(His-DPhe-Arg-Trp)hAGRP-NH$_2$ and possesses similar pharmacology, and may represent a better lead molecule since it is more quickly synthesized, less expensive to make, and does not possess disulfide bonds that could scramble to unfavorable positions. The MDES-149-2c and MDE6-5-2c peptides also possess modest selectivity for the mMC4R over the mMC3R (23- and 25-fold, respectively), more favorable than the 7- and 5-fold reported for the Tyr-c[Cys-His-DPhe-Arg-Trp-Asn-Ala-Phe-Cys]-Tyr-NH$_2$ and Tyr-c[Asp-His-DPhe-Arg-Trp-Asn-Ala-Phe-Dap]-Tyr-NH$_2$ AGRP/NDP-MSH chimeric ligands (Wilczynski, A., et al. *J. Med. Chem.* 2005, 48, 3060-3075; and Singh, A., et al. *J. Med. Chem.* 2011, 54, 1379-1390). This inherent scaffold selectivity for the MC4R may be beneficial for leads in generating MC4R selective probes.

The DPhe-Arg-Trp tripeptide sequence has previously been shown to be the minimal sequence with activity at the MCRs, with the addition of His increasing ligand potency (Haskell-Luevano, C., et al. *Peptides* 1996, 17, 995-1002). This trend was also observed with this set of AGRP/NDP-MSH chimeric ligands, where removal of the His resulted in ligands with similar or decreased agonist potencies. An exception was MDE5-151-1c, which possessed full agonist efficacy at the mMC4R with an EC$_{50}$ of 100 nM compared to MDE5-151-2c possessing a His residue, which was a partial agonist at the mMC4R (70% maximal NDP-MSH stimulation, EC$_{50}$=23 nM). These two compounds also presented a unique pharmacology at the mMC1R, mMC3R and mMC4R. Peptide MDE5-151-1c, lacking a His residue, was a partial agonist at the mMC1R and mMC3R and a full agonist at the mMC4R. The opposite pattern was observed in MDE5-151-2c, which possessed a His residue and was a full agonist at the mMC1R and mMC3R and was a partial agonist at the mMC4R. The presence of the His residue dictated whether the ligand was a full or partial agonist for this sequence at receptor subtypes.

The control peptide NDP-MSH is a synthetic analogue of α-MSH that is potent at the mMC1R, mMC3R, mMC4R, and mMC5R, and possesses modest selectivity (6 to 26-fold) for the mMC1R over the other receptors (Sawyer, T. K., et al. *Proc. Natl. Acad. Sci. U.S.A.* 1980, 77, 5754-5758). Select ligands from this study did possess significant selectivity (>100-fold) for one receptor subtype, often due to low potency of this ligand series at the mMC3R. Three compounds were >100-fold selective for the mMC1R over the mMC3R (MDE6-12-2c, MDE5-149-1c, MDE6-3-1c), while MDE6-10-1c was >2500-fold selective for the mMC1R over the mMC3R. Three of these compounds (MDE5-149-1c, MDE6-3-1c, and MDE6-10-1c) were derived from the serial truncation of Phe and Ala residues lacking a His, indicating a possible series effect for selectivity. For the mMC4R over the mMC3R, MDE6-3-1c was >100-fold selective and MDE5-149-1c and MDE6-5-1c were greater than 300-fold selective. Six compounds were selective for the mMC5R over the mMC3R, with MDE6-3-2c, MDE6-5-2c, and MDE6-12-2c possessing >100-fold selectivity, and MDE6-3-1c, MDE5-149-1c and MDE6-5-1c possessing >1000-fold selectivity for the mMC5R over the mMC3R. The ligand MDE6-10-1c was also >1000-fold selective for the mMC1R over the mMC5R. One compound (MDE6-12-1c) was a partial agonist at the mMC1R (75% NDP-MSH stimulation, EC$_{50}$=110 nM) and possessed no agonist activity at the mMC3R or mMC5R and partially stimulated the mMC4R at concentrations up to 100 μM (FIGS. 1A-1D), and possessed >500-fold selectivity for the mMC1R over the other receptor subtypes. No compounds were selective for the mMC3R, and there was no selectivity observed between the mMC4R and mMC5R.

The present structure-activity relationships study involved the conversion of potent, AGRP antagonist-derived ligands into agonists at the melanocortin receptors. Two compounds, MDE5-149-2c and MDE6-5-2c were nanomolar agonists at the mMC4R, previously indicated to be involved with energy homeostasis and food intake, and possessed some modest selectivity for the mMC4R over the mMC3R (23- and 25-fold). The uniqueness of this chimeric scaffold may allow these derivatives to bypass the detrimental side-effects associated with previously described MC4R agonists and potentially be developed into anti-obesity probes and therapeutics with further studies. Two compounds were identified that were >1000-fold selective for the mMC5R over the mMC3R (MDE5-149-1c and MDE6-5-1c) and an additional ligand was found selective for the mMC1R over other receptor subtypes (MDE6-12-1c). Further development of these compounds may generate useful probes for investigating the different physiological roles of the melanocortin receptors in vivo.

Example 4

In Vivo Murine Studies

The ability of the compounds of the invention to affect metabolic activity and/or food intake may be tested using in vivo feeding studies in mice. Specially developed mice (e.g., wild-type, melanocortin-3 receptor knockout, melanocortin-4 receptor knockout, and melanocortin-3/4 receptor double knockout) may be injected with a compound of the invention and any possible effects on food intake and metabolic activity may be assessed

Tables

TABLE 1

Analytical Data for the Peptides Synthesized in this Study.[a]

| Peptide | Structture | HPLC k' (system 1) | HPLC k' (system 2) | M + 1 (calcd) | M + 1 (obs), purity % |
|---|---|---|---|---|---|
| MDE5-149-2c | c[Pro-His-DPhe-Arg-Trp-Asn-Ala-Phe-DPro] (SEQ ID NO: 1) | 7.0 | 11.2 | 1153.6 | 1153.5% (>99%) |
| MDE5-151-2c | c[Pro-His-DPhe-Arg-Trp-Dap-Ala-Phe-DPro] (SEQ ID NO: 2) | 6.6 | 11.2 | 1125.6 | 1125.4 (>99%) |
| MDE6-3-2c | c[Pro-His-DPhe-Arg-Trp-Asn-Ala-DPro] (SEQ ID NO: 3) | 5.1 | 8.6 | 1006.5 | 1006.2 (>95%) |
| MDE6-5-2c | c[Pro-His-DPhe-Arg-Trp-Dap-Ala-DPro] (SEQ ID NO: 4) | 5.0 | 7.9 | 978.5 | 978.1 (>95%) |
| MDE6-10-2c | c[Pro-His-DPhe-Arg-Trp-Asn-DPro] (SEQ ID NO: 5) | 5.1 | 8.2 | 935.5 | 935.2 (>96%) |
| MDE6-12-2c | c[Pro-His-DPhe-Arg-Trp-Dap-DPro] (SEQ ID NO: 6) | 5.5 | 8.0 | 907.5 | 907.5 (>96%) |
| MDE5-147-2c | c[Pro-His-DPhe-Arg-Trp-DPro] (SEQ ID NO: 7) | 5.2 | 8.0 | 821.4 | 821.2 (>98%) |
| MDE5-149-1c | c[Pro-DPhe-Arg-Trp-Asn-Ala-Phe-DPro] (SEQ ID NO: 8) | 7.7 | 12.2 | 1016.5 | 1016.5 (>99%) |
| MDE5-151-1c | c[Pro-DPhe-Arg-Trp-Dap-Ala-Phe-DPro] (SEQ ID NO: 9) | 7.2 | 11.5 | 988.5 | 988.4 (>99%) |
| MDE6-3-1c | c[Pro-DPhe-Arg-Trp-Asn-Ala-DPro] (SEQ ID NO: 10) | 6.6 | 10.0 | 869.4 | 869.1 (>97%) |
| MDE6-5-1c | c[Pro-DPhe-Arg-Trp-Dap-Ala-DPro] (SEQ ID NO: 11) | 5.9 | 9.3 | 841.4 | 841.2 (>98%) |
| MDE6-10-1c | c[Pro-DPhe-Arg-Trp-Asn-DPro] (SEQ ID NO: 12) | 5.0 | 9.0 | 798.4 | 798.0 (>95%) |
| MDE6-12-1c | c[Pro-DPhe-Arg-Trp-Dap-DPro] (SEQ ID NO: 13) | 5.7 | 8.4 | 770.4 | 770.4 (>96%) |
| MDE5-147-1c | c[Pro-DPhe-Arg-Trp-DPro] (SEQ ID NO: 14) | 6.9 | 10.5 | 684.4 | 684.2 (>96%) |

[a] HPLC k' = [(peptide retention time-solvent retention time)/solvent retention time] in solvent system 1 (10% acetonitrile in 0.1% trifluoroacetic acid/water and a gradient to 90% acetonitrile over 35 min) or solvent system 2 (10% methanol in 0.1% trifluoroacetic acid/water and a gradient to 90% methanol over 35 min). An analytical Vydac C18 column (Vydac 218TP104) was used with a flow rate of 1.5 mL/min. The peptide purity was determined by HPLC at a wavelength of 214 nm.

TABLE 2

Pharmacology of Chimeric NDP-MSH/AGRP β-Hairpin Loop Analogues at the Mouse Melanocortin Receptors.[a]

| Peptide | Structure | mMC1R | mMC3R | mMC4R | mMC5R |
|---|---|---|---|---|---|
| | | | $EC_{50}$ (nM) | | |
| NDP-MSH | | 0.015 ± 0.005 | 0.09 ± 0.02 | 0.39 ± 0.07 | 0.11 ± 0.02 |
| MDE5-149-2c | c[Pro-His-DPhe-Arg-Trp-Asn-Ala-Phe-DPro] (SEQ ID NO: 1) | 0.35 ± 0.05 | 32 ± 8 | 1.4 ± 0.4 | 0.45 ± 0.07 |
| MDE6-3-2c | c[[Pro-His-DPhe-Arg-Trp-Asn-Ala-DPro] (SEQ ID NO: 3) | 12 ± 2 | 300 ± 100 | 29 ± 2 | 2.1 ± 0.2 |
| MDE6-10-2c | c[Pro-His-DPhe-Arg-Trp-Asn-DPro] (SEQ ID NO: 5) | 50 ± 20 | PA, 65% NDP (510 ± 50) | 170 ± 20 | 16.8 ± 0.8 |
| MDE5-151-2c | c[Pro-His-DPhe-Arg-Trp-Dap-Ala-Phe-DPro] (SEQ ID NO: 2) | 24 ± 4 | 260 ± 90 | PA, 70% NDP (23 ±8) | 18 ± 2 |
| MDE6-5-2c | c[Pro-His-DPhe-Arg-Trp-Dap-Ala-DPro] (SEQ ID NO: 4) | 1.1 ± 0.4 | 40 ± 10 | 1.6 ± 0.2 | 0.3 ± 0.1 |
| MDE6-12-2c | c[Pro-His-DPhe-Arg-Trp-Dap-DPro] (SEQ ID NO: 6) | 460 ± 60 | 65% @ 100 μM | 950 ± 80 | 330 ± 30 |
| MDE5-147-2c | c[Pro-His-DPhe-Arg-Trp-DPro] (SEQ ID NO: 7) | 900 ± 200 | 60% @ 100 μM | 65% @ 100 μM | 6,000 ± 2,000 |
| MDE5-149-1c | c[Pro-DPhe-Arg-Trp-Asn-Ala-Phe-DPro] (SEQ ID NO: 8) | 400 ± 200 | 45% @ 100 μM | 130 ± 70 | 40 ± 10 |
| MDE6-3-1c | c[Pro-DPhe-Arg-Trp-Asn-Ala-DPro] (SEQ ID NO: 10) | 500 ± 60 | 55% @ 100 μM | 420 ± 40 | 70 ± 10 |
| MDE6-10-1c | c[Pro-DPhe-Arg-Trp-Asn-DPro] (SEQ ID NO: 12) | 40 ± 20 | >100,000 | 1,100 ± 100 | 25% @ 100 μM |
| MDE5-151-1c | c[Pro-DPhe-Arg-Trp-DAP-Ala-Phe-DPro] (SEQ ID NO: 9) | PA, 45% NDP (190 ± 90) | PA, 70% NDP (3,000 ± 1,000) | 100 ± 40 | 46 ± 6 |
| MDE6-5-1c | c[Pro-DPhe-Arg-Trp-Dap-Ala-DPro] (SEQ ID NO: 11) | 600 ± 200 | 70% @ 100 μM | 150 ± 10 | 48 ± 5 |
| MDE6-5-1c | c[Pro-DPhe-Arg-Trp-Dap-DPro] (SEQ ID NO: 13) | PA, 75% NDP (110 ± 20) | >100,000 | 35% @ 100 μM | >100,000 |
| MDE5-147-1c | c[Pro-DPhe-Arg-Trp-DPro] (SEQ ID NO: 14) | 1,800 ± 500 | >100,000 | 50% @ 100 μM | 75% @ 100 μM |

[a] The indicated errors represent the standard error of the mean determined from at least three independent experiments. >100,000 indicates that the compound was examined but lacked agonist activity at up to 100 μM concentrations. A percentage denotes the percent maximal stimulatory response observed at 100 μM concentrations but not enough stimulation was observed to determine an $EC_{50}$ value. PA denotes a partial agonist with the percent maximal NDP stimulation and apparent $EC_{50}$ value (compounds showing >80% maximal NDP response were considered full agonists.

Example 5

As described herein, compound 2 (c[Pro-His-DPhe-Arg-Trp-Dap-Ala-DPro] (SEQ ID NO:4)) has been administered in male mice. This compound has been administered via a cannula directly into the brain (ICV administration) or through an injection into the spinal cord (IT administration), at three different doses each administration route (2 nmol, 5 nmol, and 10 nmol). After compound administration, the mice were monitored in TSE metabolic cages, which record food intake, water intake, ambulatory activity (how many times a mouse breaks a light beam, which can give an indication of toxicity), respiratory-exchange ratio (RER, ratio between amount of $CO_2$ produced in metabolism and $O_2$ consumed, giving an indication if fat [RER value closer to 0.7] or carbohydrates [RER value closer to 1] is the energy source being utilized), and energy expenditure.

Figure 2A:
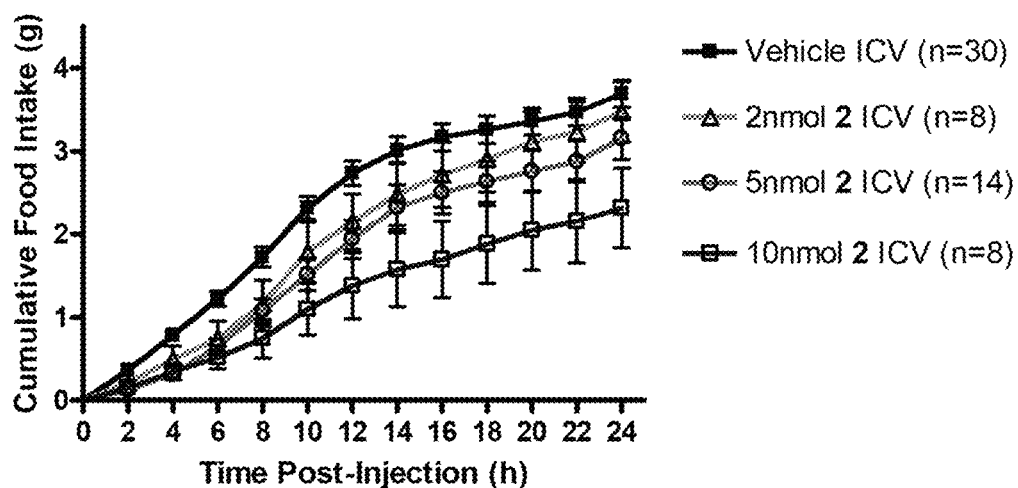
FIGS. 2A-2B show cumulative food intake following ICV administration at 24 h (FIG. 2A) and 72 h (FIG. 2B) time points.
Figure 2B:
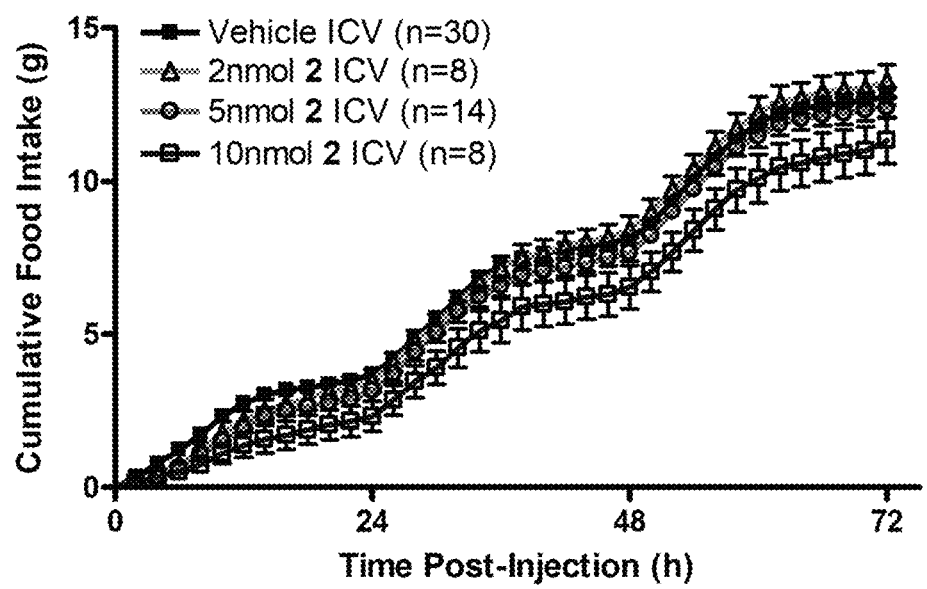
Figure 3A:
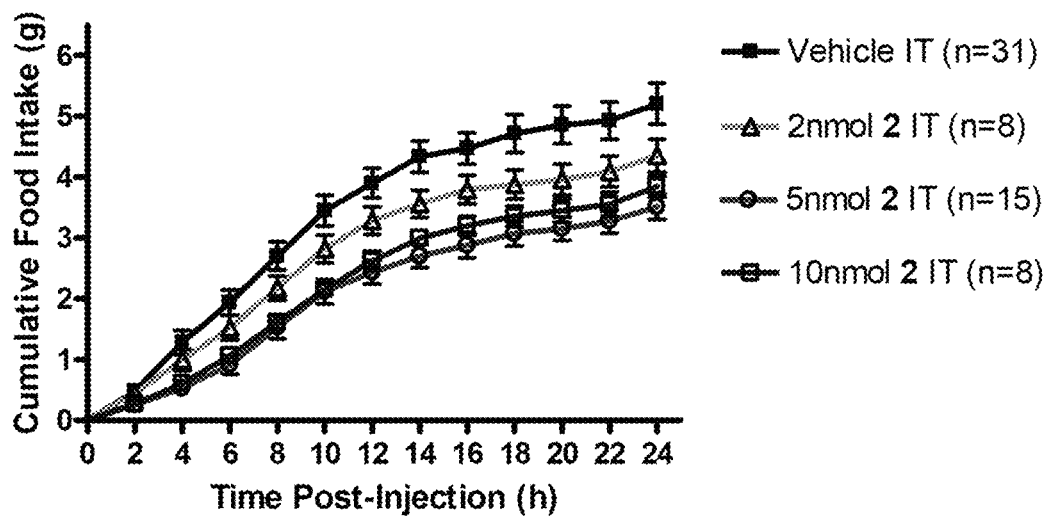
FIGS. 3A-3B show cumulative food intake following IT administration at 24 h (FIG. 3A) and 72 h (FIG. 3B) time points.
Figure 3B:
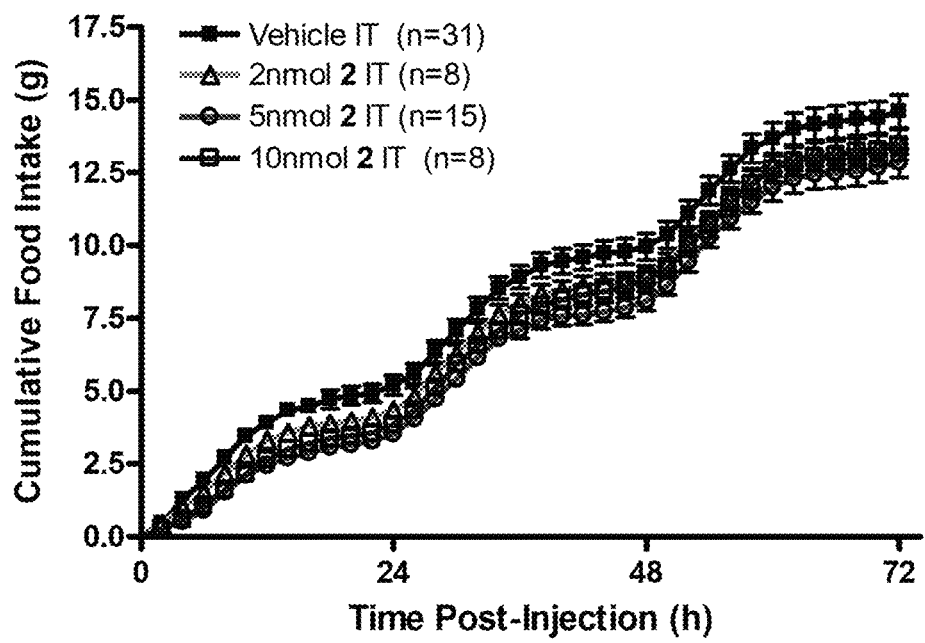

FIGS. 2A-2B show cumulative food intake following ICV administration (24 and 72 h time points). A dose response was observed for the first 24 h, such that increasing amounts of the compound (2) resulted in a further decreased food intake. The 10 nmol dose resulted in a decreased food intake through 72 h. Following IT administration, decreased food intake was observed, but was not in a dose-response manner such as the ICV administered compound (FIGS. 3A-3B).

Figure 4A:
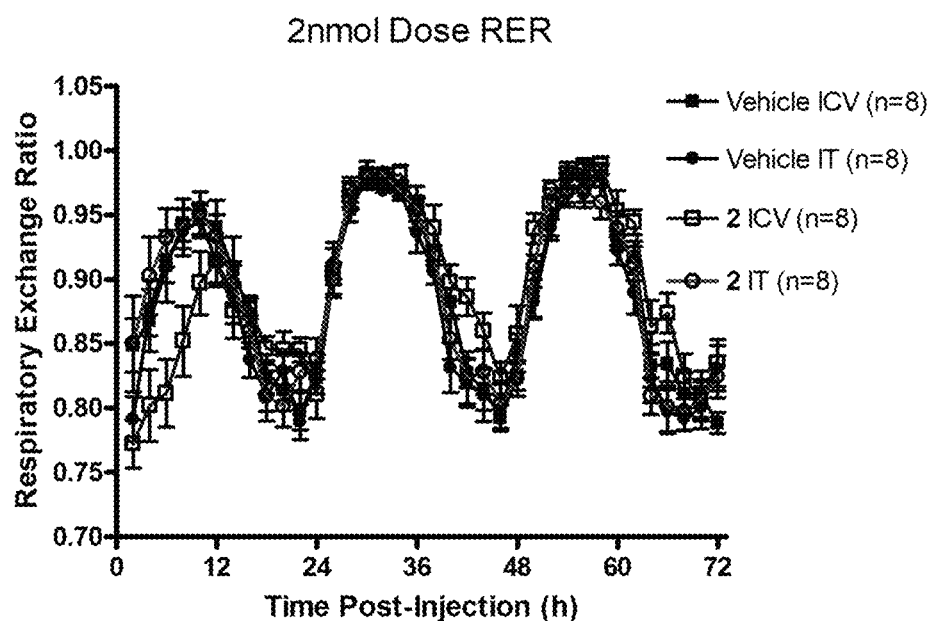
FIGS. 4A-4C show the Respiratory Exchange Ratio (RER) following ICV administration of 2 nmol (FIG. 4A), 5 nmol (FIG. 4B) and 10 nmol (FIG. 4C) doses.
Figure 4B:
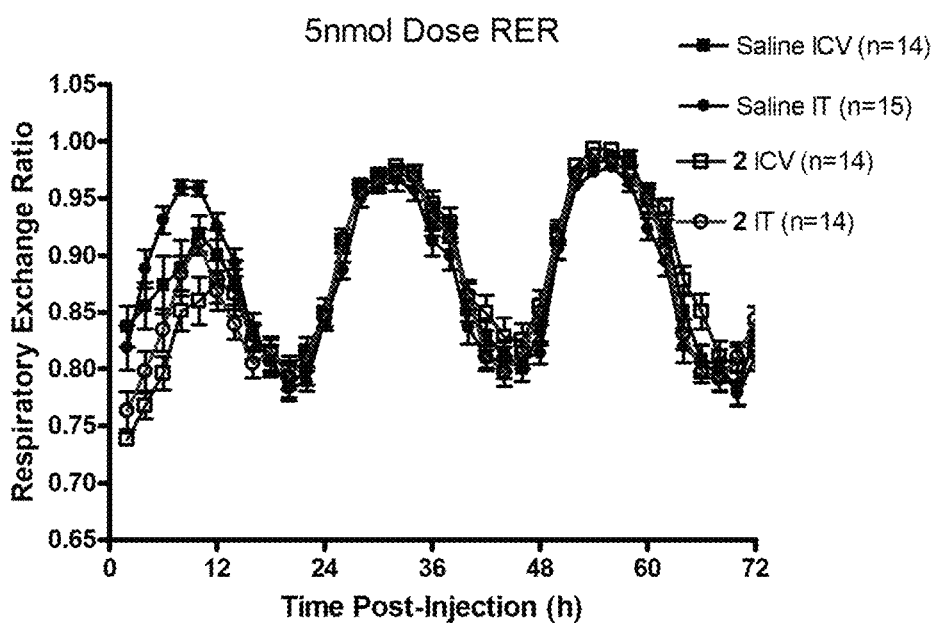
Figure 4C:
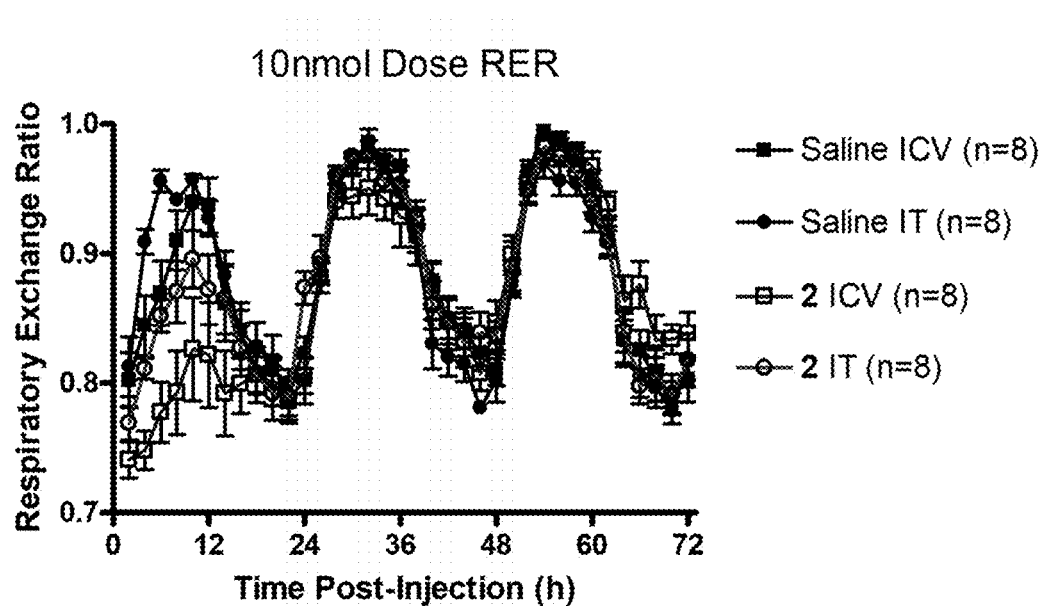

The RER also indicated a dose effect following ICV administration (FIGS. 4A-4C). Graphed by dose (2 nmol, 5 nmol, 10 nmol), the 2 and 5 nmol dose indicated a decreased RER compared to vehicle control in the first 24 h (FIGS. 4A-4B). This indicates that the mice were utilizing more fats for energy; coupled with the decreased food intake, which would provide carbohydrates, this indicates the mice were beginning to utilize fat stores. The effect was more robust in the 10 nmol dose, where the RER for the first 24 h maintained a level indicative of fat utilization, suggesting the mice were eating less while utilizing fat stores (FIG. 4C). A more modest effect was observed following IT administration. In all cases, the curves overlap with the vehicle controls at 24 h, indicating that following a single dose, the effects on RER lasted 24 h.

The ambulatory activity, water intake, and energy expenditure were not different from compound to vehicle treated animals.

Example 6

As described herein, c[Pro-His-DPhe-Arg-Trp-Asn-Ala-Phe-DPro] (SEQ ID NO:1) and c[Pro-His-DPhe-Arg-Trp-Dap-Ala-DPro] (SEQ ID NO:4) have been further modified in an effort to enhance their blood brain barrier penetrance. Specifically, the Ala residue has been replaced with a Lys residue, through which 0, 1, 2, or 3 Arg residues have been incorporated as described herein (see, Table 3). These modifications may allow alternative administration routes to be employed (e.g., routes not involving direct administration into the CNS). The activity of these compounds may be evaluated using assays known in the art or as described in the Examples.

TABLE 3

Modified Compounds

| Compounds | Sequence Identifier |
| --- | --- |
| c[Pro-His-DPhe-Arg-Trp-Asn-Lys-Phe-DPro] | SEQ ID NO: 34 |
| c[Pro-His-DPhe-Arg-Trp-Asn-Lys(Ac-Arg)-Phe-DPro] | SEQ ID NO: 35 |
| c[Pro-His-DPhe-Arg-Trp-Asn-Lys(Ac-Arg-Arg)-Phe-DPro] | SEQ ID NO: 36 |
| c[Pro-His-DPhe-Arg-Trp-Asn-Lys(Ac-Arg-Arg-Arg)-Phe-DPro] | SEQ ID NO: 37 |
| c[Pro-His-DPhe-Arg-Trp-Dap-Lys-DPro] | SEQ ID NO: 38 |
| c[Pro-His-DPhe-Arg-Trp-Dap-Lys(Ac-Arg)-DPro] | SEQ ID NO: 39 |
| c[Pro-His-DPhe-Arg-Trp-Dap-Lys(Ac-Arg-Arg)-DPro] | SEQ ID NO: 40 |
| c[Pro-His-DPhe-Arg-Trp-Dap-Lys(Ac-Arg-Arg-Arg)-DPro] | SEQ ID NO: 41 |

The following abbreviations are used:
ACTH, Adrenocorticotropin Hormone;
Fmoc, 9-fluorenylmethoxycarbonyl;
AGRP, Agouti-Related Protein;
GPCR, G Protein-Coupled Receptor;
cAMP, cyclic 5'-adenosine monophosphate;
MC1R, Melanocortin-1 Receptor;
MC2R, Melanocortin-2 Receptor;
MC3R, Melanocortin-3 Receptor;
MC4R, Melanocortin-4 Receptor;
MC5R, Melanocortin-5 Receptor;
MCR, Melanocortin Receptor;
MSH, Melanocyte Stimulating Hormone;
POMC, Proopiomelanocortin;
α-MSH, Alpha-Melanocyte Stimulating Hormone;
β-MSH, Beta-Melanocyte Stimulating Hormone;
γ-MSH, Gamma-Melanocyte Stimulating Hormone;
NDP-MSH (4-Norleucine-7-D-Phenylalanine), Ac-Ser-Tyr-Ser-Nle-Glu-His-DPhe-Arg-Trp-Gly-Lys-Pro-Val-$NH_2$;
Nle, norleucine;
RP-HPLC, reverse-phase high-pressure liquid chromatography;
HBSS, Hanks' Balanced Salt Solution;
HEPES, 4-(2-hydroxyethyl)-1-piperazineethanesulfonic acid;
IBMX, 3-isobutyl-1-methylxanthine;
BSA, bovine serum albumin.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A cyclic compound of formula I:

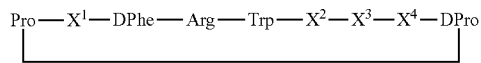

wherein:
Pro is L-proline, wherein the pyrrolidinyl ring is optionally substituted with one or more halo groups, $(C_1-C_4)$alkyl, $-O(C_1-C_4)$alkyl, $(C_1-C_4)$haloalkyl, or $-O(C_1-C_4)$haloalkyl;
DPhe is D-phenylalanine, wherein the phenyl ring is optionally substituted with one or more halo groups, $(C_1-C_4)$alkyl, $-O(C_1-C_4)$alkyl, $(C_1-C_4)$haloalkyl, or $-O(C_1-C_4)$haloalkyl;
Arg is L-arginine;
Trp is L-tryptophan, wherein the indolyl ring is optionally substituted with one or more halo groups, $(C_1-C_4)$alkyl, $-O(C_1-C_4)$alkyl, $(C_1-C_4)$haloalkyl, or $-O(C_1-C_4)$haloalkyl;
DPro is D-proline, wherein the pyrrolidinyl ring is optionally substituted with one or more halo groups, $(C_1-C_4)$alkyl, $-O(C_1-C_4)$alkyl, $(C_1-C_4)$haloalkyl, or $-O(C_1-C_4)$haloalkyl;
$X^1$ is a direct bond or an amino acid;
$X^2$ is a direct bond or an amino acid;
$X^3$ is a direct bond or an amino acid;
$X^4$ is an amino acid, dipeptide or tripeptide;
wherein when $X^1$, $X^2$, $X^3$ or $X^4$ is a lysine or comprises a lysine, the side-chain amine of the lysine is optionally linked through an amide bond to the carboxy terminus of an amino acid or the carboxy terminus of a peptide that is 2, 3, or 4 amino acids in length, and wherein the amino acid or peptide linked to the lysine is optionally acylated;
or a salt thereof.

2. The compound of claim 1, wherein:

Pro is L-proline, wherein the pyrrolidinyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl;

DPhe is D-phenylalanine, wherein the phenyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl;

Arg is L-arginine;

Trp is L-tryptophan, wherein the indolyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl;

DPro is D-proline, wherein the pyrrolidinyl ring is optionally substituted with one or more halo groups, $(C_1-C_4)$alkyl, $—O(C_1-C_4)$alkyl, $(C_1-C_4)$haloalkyl, or $—O(C_1-C_4)$haloalkyl;

$X^1$ is a direct bond, or an amino acid;

$X^2$ is a direct bond or an amino acid;

$X^3$ is an amino acid;

$X^4$ is an amino acid, dipeptide or tripeptide;

or a salt thereof.

3. The compound of claim 1, wherein Pro is L-proline; DPro is D-proline; DPhe is D-phenylalanine; Trp is L-tryptophan; and Arg is L-arginine.

4. The compound of claim 1, wherein $X^1$, $X^2$, $X^3$ and/or $X^4$ are an amino acid independently selected from the group consisting of L-Ala, L-Asp, L-Glu, L-Phe, L-Gly, L-His, L-Ile, L-Lys, L-Leu, L-Met, L-Asn, L-Pro, L-Gln, L-Arg, L-Ser, L-Thr, L-Val, L-Trp, L-Tyr, L-Dap, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, D-Dap, L-Nle, D-Nle, L-Cha, D-Cha, L-PyrAla, D-PyrAla, L-ThiAla, D-ThiAla, L-Tic, D-Tic, (pCl)L-Phe, (pCl)D-Phe, (pI)L-Phe, (pI)D-Phe, (pNO2)L-Phe, (pNO2)D-Phe, 2-L-Nal, 2-D-Nal, β-Ala, ε-Aminocaproic acid, Met[O2], dehydPro, and (3I)Tyr.

5. The compound of claim 1, wherein $X^1$ is a direct bond.

6. The compound of claim 1, wherein $X^1$ is L-histidine.

7. The compound of claim 1, wherein $X^2$ is a direct bond.

8. The compound of claim 1, wherein $X^2$ is L-asparagine or L-diaminopropionic acid.

9. The compound of claim 1, wherein $X^3$ is a direct bond.

10. The compound of claim 1, wherein $X^3$ is L-alanine or L-lysine.

11. The compound of claim 1, wherein $X^3$ is L-lysine, and wherein the side-chain of the L-lysine is linked through an amide bond to the carboxy terminus of an amino acid or the carboxy terminus of a peptide that is 2, 3, or 4 amino acids in length.

12. The compound of claim 11, wherein the amine terminus of the amino acid or peptide linked to the L-lysine is acylated.

13. The compound of claim 11, wherein the amino acid linked to the lysine is L-arginine or wherein peptide linked the lysine comprises an L-arginine.

14. The compound of claim 1, wherein $X^4$ is L-phenylalanine.

15. The compound of claim 1 which is selected from the group consisting of:

c[Pro-His-DPhe-Arg-Trp-Asn-Ala-Phe-DPro] (SEQ ID NO:1);

c[Pro-His-DPhe-Arg-Trp-Dap-Ala-Phe-DPro] (SEQ ID NO:2);

c[Pro-His-DPhe-Arg-Trp-Asn-Ala-DPro] (SEQ ID NO:3);

c[Pro-His-DPhe-Arg-Trp-Dap-Ala-DPro] (SEQ ID NO:4);

c[Pro-His-DPhe-Arg-Trp-Asn-DPro] (SEQ ID NO:5);

c[Pro-His-DPhe-Arg-Trp-Dap-DPro] (SEQ ID NO:6);

c[Pro-DPhe-Arg-Trp-Asn-Ala-Phe-DPro] (SEQ ID NO:8);

c[Pro-DPhe-Arg-Trp-Dap-Ala-Phe-DPro] (SEQ ID NO:9);

c[Pro-DPhe-Arg-Trp-Asn-Ala-DPro] (SEQ ID NO:10);

c[Pro-DPhe-Arg-Trp-Dap-Ala-DPro] (SEQ ID NO:11);

c[Pro-DPhe-Arg-Trp-Asn-DPro] (SEQ ID NO:12);

c[Pro-DPhe-Arg-Trp-Dap-DPro] (SEQ ID NO:13);

c[Pro-His-DPhe-Arg-Trp-Asn-Lys-Phe-DPro] (SEQ ID NO:34);

c[Pro-His-DPhe-Arg-Trp-Asn-Lys(Ac-Arg)-Phe-DPro] (SEQ ID NO:35);

c[Pro-His-DPhe-Arg-Trp-Asn-Lys(Ac-Arg-Arg)-Phe-DPro] (SEQ ID NO:36);

c[Pro-His-DPhe-Arg-Trp-Asn-Lys(Ac-Arg-Arg-Arg)-Phe-DPro] (SEQ ID NO:37);

c[Pro-His-DPhe-Arg-Trp-Dap-Lys-DPro] (SEQ ID NO:38);

c[Pro-His-DPhe-Arg-Trp-Dap-Lys(Ac-Arg)-DPro] (SEQ ID NO:39);

c[Pro-His-DPhe-Arg-Trp-Dap-Lys(Ac-Arg-Arg)-DPro] (SEQ ID NO:40); and c[Pro-His-DPhe-Arg-Trp-Dap-Lys(Ac-Arg-Arg-Arg)-DPro] (SEQ ID NO:41);

and salts thereof.

16. The compound of claim 1 which is selected from the group consisting of (SEQ ID NOS 34-41, respectively, in order of appearance):

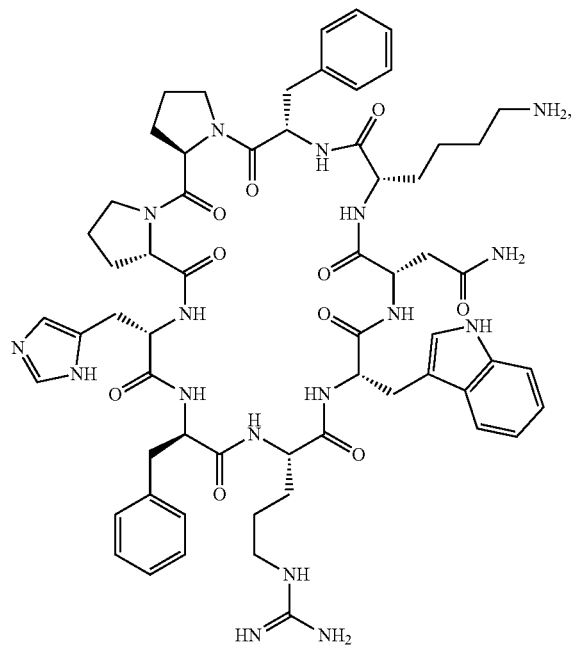
c[Pro-His-DPhe-Arg-Trp-Asn-Lys-Phe-DPro]
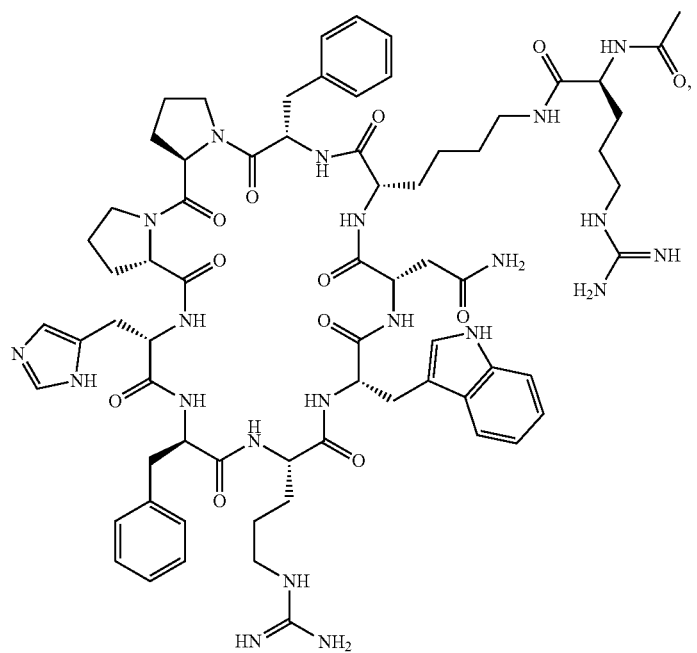
c[Pro-His-DPhe-Arg-Trp-Asn-Lys(Ac-Arg)-Phe-DPro]

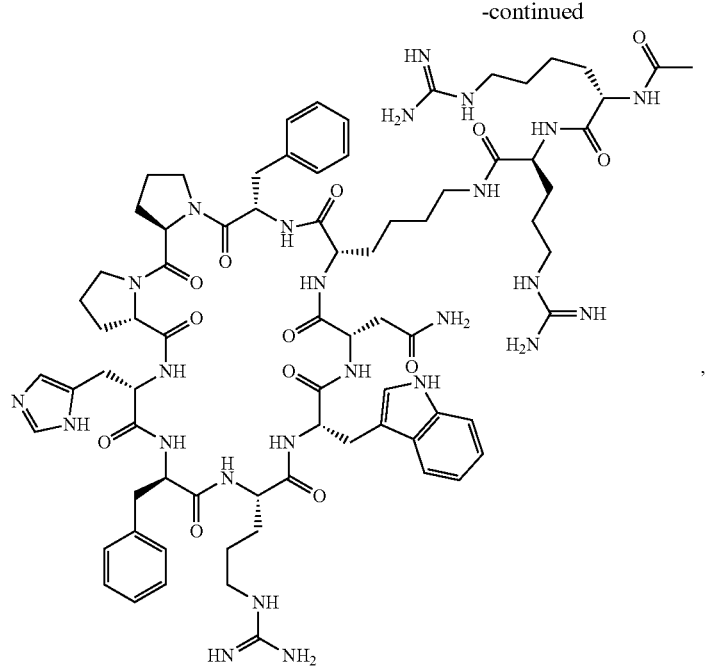
c[Pro-His-DPhe-Arg-Trp-Asn-Lys(Ac-Arg-Arg)-Phe-DPro]
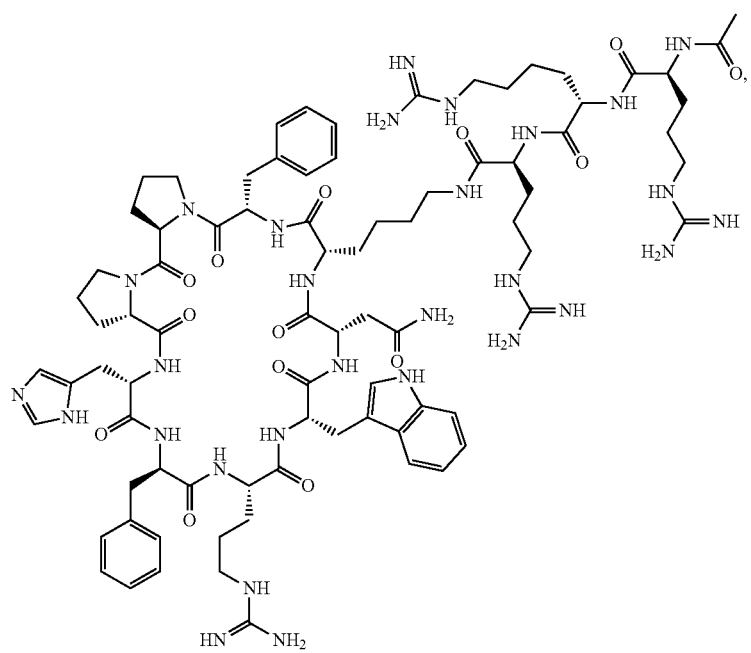
c[Pro-His-DPhe-Arg-Trp-Asn-Lys(Ac-Arg-Arg-Arg)-Phe-DPro]

-continued
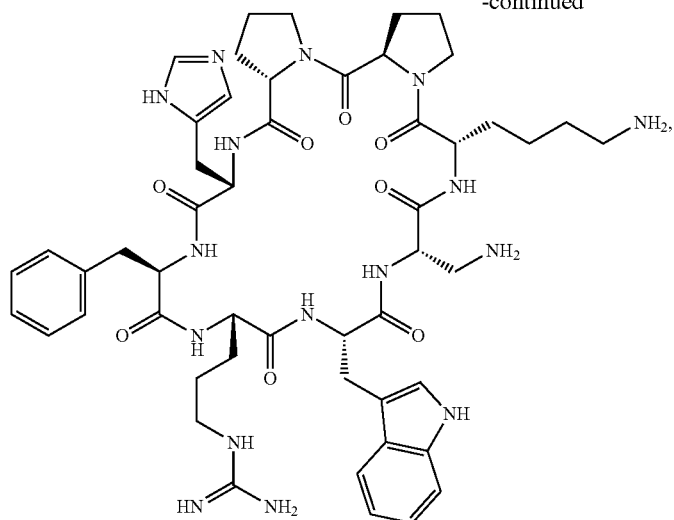
c[Pro-His-DPhe-Arg-Trp-Dap-Lys-DPro]
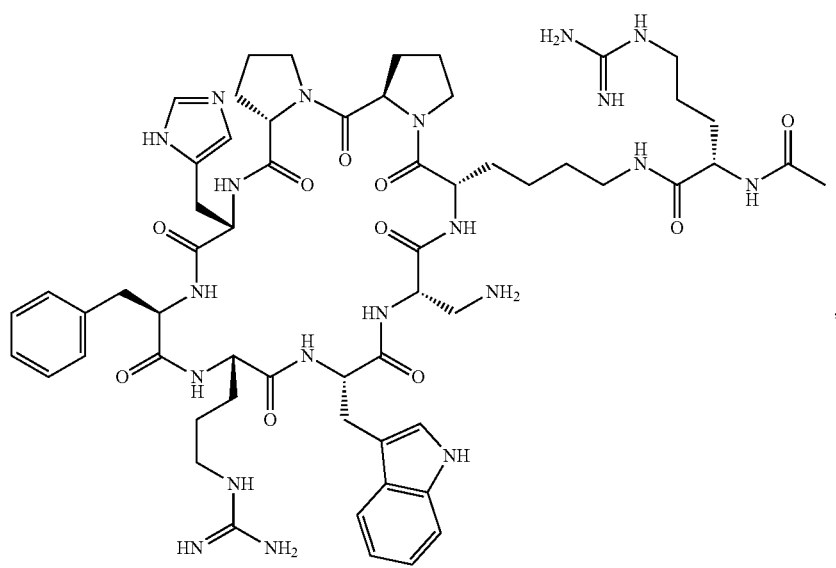
c[Pro-His-DPhe-Arg-Trp-Dap-Lys(Ac-Arg)-DPro]

-continued
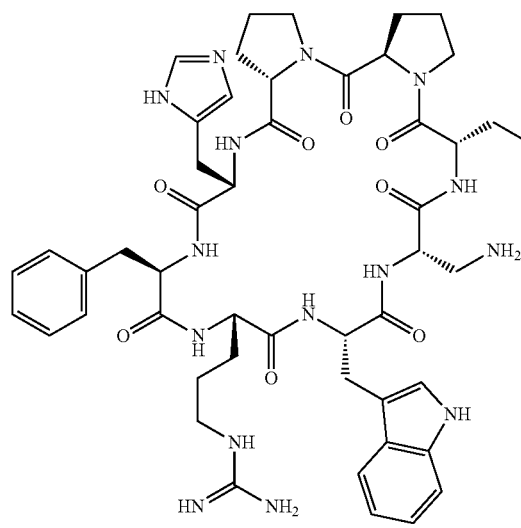
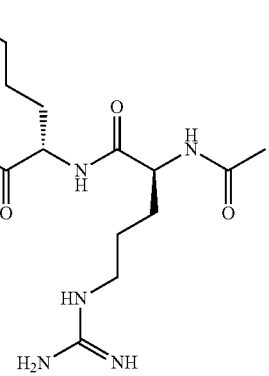
c[Pro-His-DPhe-Arg-Trp-Dap-Lys(Ac-Arg-Arg)-DPro]
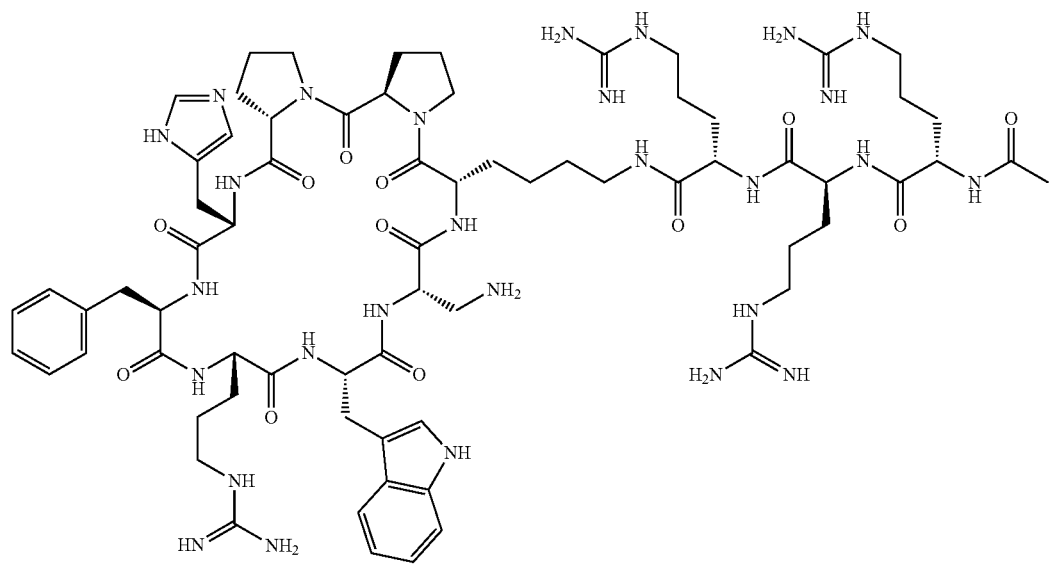
c[Pro-His-DPhe-Arg-Trp-Dap-Lys(Ac-Arg-Arg-Arg)-DPro]
and salts thereof.

17. A composition comprising a compound of formula I as described in claim 1, or a pharmaceutically acceptable salt thereof, and a pharmaceutically acceptable carrier.

18. A compound selected from the group consisting of:

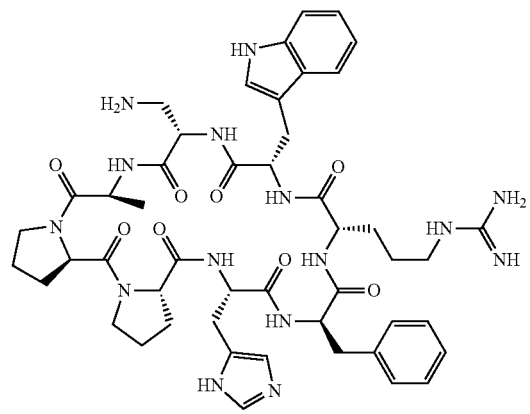

c[Pro-His-DPhe-Arg-Trp-Dap-Ala-DPro] (SEQ ID NO: 4)

and

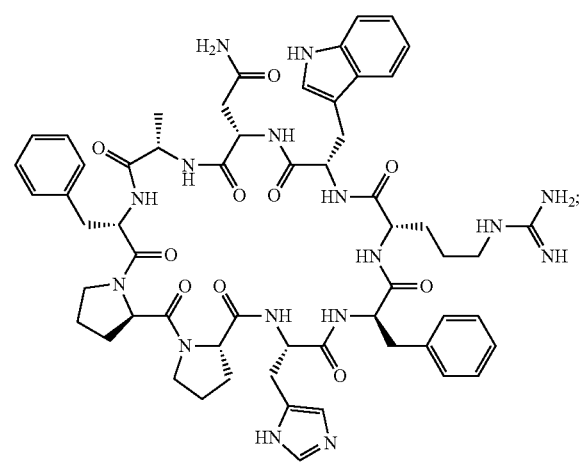

c[Pro-His-DPhe-Arg-Trp-Asn-Ala-Phe-DPro] (SEQ ID NO: 1)

and salts thereof.

19. The compound of claim 18, which is

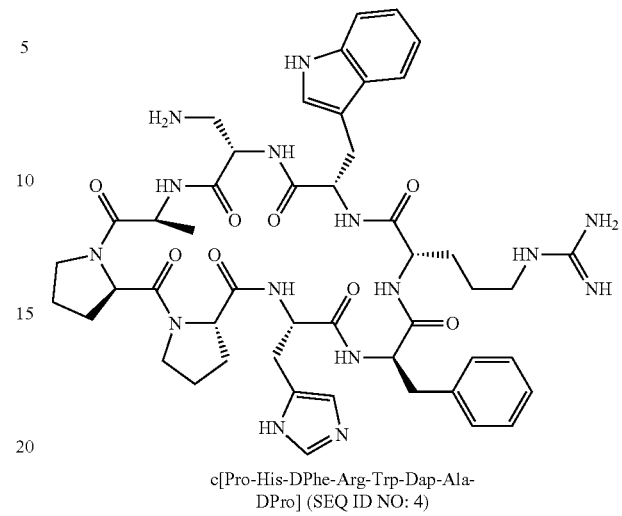

c[Pro-His-DPhe-Arg-Trp-Dap-Ala-DPro] (SEQ ID NO: 4)

or a salt thereof.

20. The compound of claim 18, which is c[Pro-His-DPhe-Arg-Trp-Asn-Ala-Phe-DPro] (SEQ ID NO: 1)

or a salt thereof.

21. A method of modulating the activity of a melanocortin receptor in vitro or in vivo comprising contacting the receptor with an effective amount of a compound of formula I as described in claim 1, or a pharmaceutically acceptable salt thereof.

22. A method of modulating metabolic activity, modulating appetite and/or ameliorating obesity in an animal in need thereof, comprising administering an effective amount of a compound of formula I as described in claim 18, or a pharmaceutically acceptable salt thereof, to the animal.

* * * * *

SEQUENCE LISTING

<160> NUMBER OF SEQ ID NOS: 50

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 1

Pro His Phe Arg Trp Asn Ala Phe Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (9)..(9)
<223> OTHER INFORMATION: D-amino acid

<400> SEQUENCE: 2

Pro His Phe Arg Trp Xaa Ala Phe Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 3

Pro His Phe Arg Trp Asn Ala Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic

```
                peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 4

Pro His Phe Arg Trp Xaa Ala Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 5

Pro His Phe Arg Trp Asn Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (7)..(7)
<223> OTHER INFORMATION: D-amino acid

<400> SEQUENCE: 6

Pro His Phe Arg Trp Xaa Pro
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
```

```
<220> FEATURE:
<221> NAME/KEY: MOD_RES
<222> LOCATION: (6)..(6)
<223> OTHER INFORMATION: D-amino acid

<400> SEQUENCE: 7

Pro His Phe Arg Trp Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 8

Pro Phe Arg Trp Asn Ala Phe Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 9

Pro Phe Arg Trp Xaa Ala Phe Pro
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 10

Pro Phe Arg Trp Asn Ala Pro
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: D-amino acid

<400> SEQUENCE: 11

Pro Phe Arg Trp Xaa Ala Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 12

Pro Phe Arg Trp Asn Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (6)..(6)
<223> OTHER INFORMATION: D-amino acid

<400> SEQUENCE: 13

Pro Phe Arg Trp Xaa Pro
1               5

<210> SEQ ID NO 14
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 14

Pro Phe Arg Trp Pro
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid

<400> SEQUENCE: 15

His Phe Arg Trp Asn
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: Dap

<400> SEQUENCE: 16

His Phe Arg Trp Xaa
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid

<400> SEQUENCE: 17

Phe Arg Trp Asn
1

<210> SEQ ID NO 18
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (4)..(4)
<223> OTHER INFORMATION: Dap

<400> SEQUENCE: 18

Phe Arg Trp Xaa
1

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid

<400> SEQUENCE: 19

Phe Arg Trp
1

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 20

Pro His Phe Arg Trp Asn Ala Phe Pro
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (9)..(9)
<223> OTHER INFORMATION: D-amino acid
```

<400> SEQUENCE: 21

Pro His Phe Arg Trp Xaa Ala Phe Pro
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 22

Pro His Phe Arg Trp Asn Ala Pro
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 23

Pro His Phe Arg Trp Xaa Ala Pro
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 24

Pro His Phe Arg Trp Asn Pro
1               5

<210> SEQ ID NO 25
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (7)..(7)
<223> OTHER INFORMATION: D-amino acid

<400> SEQUENCE: 25

Pro His Phe Arg Trp Xaa Pro
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 26

Pro His Phe Arg Trp Pro
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (8)..(8)
<223> OTHER INFORMATION: D-amino acid

<400> SEQUENCE: 27

Pro Phe Arg Trp Asn Ala Phe Pro
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
```

```
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 28

Pro Phe Arg Trp Xaa Ala Phe Pro
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 29

Pro Phe Arg Trp Asn Ala Pro
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (7)..(7)
<223> OTHER INFORMATION: D-amino acid

<400> SEQUENCE: 30

Pro Phe Arg Trp Xaa Ala Pro
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (6)..(6)
<223> OTHER INFORMATION: D-amino acid
```

```
<400> SEQUENCE: 31

Pro Phe Arg Trp Asn Pro
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: Dap
<220> FEATURE:
<221> NAME/KEY: MOD_RES
<222> LOCATION: (6)..(6)
<223> OTHER INFORMATION: D-amino acid

<400> SEQUENCE: 32

Pro Phe Arg Trp Xaa Pro
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 33

Pro Phe Arg Trp Pro
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 34

Pro His Phe Arg Trp Asn Lys Phe Pro
1               5

<210> SEQ ID NO 35
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 35

Pro His Phe Arg Trp Asn Lys Phe Pro
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 36

Pro His Phe Arg Trp Asn Lys Phe Pro
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 37

Pro His Phe Arg Trp Asn Lys Phe Pro
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
```

```
<221> NAME/KEY: MOD_RES
<222> LOCATION: (8)..(8)
<223> OTHER INFORMATION: D-amino acid

<400> SEQUENCE: 38

Pro His Phe Arg Trp Xaa Lys Pro
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 39

Pro His Phe Arg Trp Xaa Lys Pro
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 40

Pro His Phe Arg Trp Xaa Lys Pro
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
```

```
<222> LOCATION: (8)..(8)
<223> OTHER INFORMATION: D-amino acid

<400> SEQUENCE: 41

Pro His Phe Arg Trp Xaa Lys Pro
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 42

Pro His Phe Arg Trp Asn Lys Phe Pro
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 43

Pro His Phe Arg Trp Asn Lys Phe Pro
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 44

Pro His Phe Arg Trp Asn Lys Phe Pro
1               5

<210> SEQ ID NO 45
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (9)..(9)
<223> OTHER INFORMATION: D-amino acid

<400> SEQUENCE: 45

Pro His Phe Arg Trp Asn Lys Phe Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 46

Pro His Phe Arg Trp Xaa Lys Pro
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 47

Pro His Phe Arg Trp Xaa Lys Pro
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 48

Pro His Phe Arg Trp Xaa Lys Pro
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Dap
<220> FEATURE:
<221> NAME/KEY: MOD_RES
<222> LOCATION: (8)..(8)
<223> OTHER INFORMATION: D-amino acid

<400> SEQUENCE: 49

Pro His Phe Arg Trp Xaa Lys Pro
1               5

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Phe Arg Trp
1
```